US009173963B2

(12) United States Patent
Reya et al.

(10) Patent No.: US 9,173,963 B2

(45) Date of Patent: Nov. 3, 2015

(54) DIAGNOSTIC AND TREATMENT FOR CHRONIC AND ACUTE PHASE MYELOID LEUKEMIA

(75) Inventors: Tannishtha Reya, San Diego, CA (US); Hyog Y. Kwon, La Jolla, CA (US); Takahiro Ito, San Diego, CA (US); Dong-Wook Kim, Seoul (KR); Vivian Oehler, Seattle, WA (US); Jerald Radich, Sammamish, WA (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/320,324

(22) PCT Filed: May 14, 2010

(86) PCT No.: PCT/US2010/035039

§ 371 (c)(1), (2), (4) Date: Apr. 24, 2012

(87) PCT Pub. No.: WO2010/132861

PCT Pub. Date: Nov. 18, 2010

(65) Prior Publication Data

US 2012/0208188 A1 Aug. 16, 2012

Related U.S. Application Data

(60) Provisional application No. 61/178,370, filed on May 14, 2009, provisional application No. 61/332,943, filed on May 10, 2010.

(51) Int. Cl.

| | |
|---|---|
| ***A61K 31/00*** | (2006.01) |
| ***A61K 48/00*** | (2006.01) |
| ***C12N 15/113*** | (2010.01) |
| ***C12N 15/86*** | (2006.01) |
| ***C12Q 1/68*** | (2006.01) |
| ***G01N 33/50*** | (2006.01) |
| ***G01N 33/574*** | (2006.01) |

(52) U.S. Cl.

CPC ............ *A61K 48/005* (2013.01); *C12N 15/113* (2013.01); *C12N 15/86* (2013.01); *C12Q 1/6886* (2013.01); *G01N 33/5011* (2013.01); *G01N 33/57496* (2013.01); *C12N 2310/14* (2013.01); *C12N 2740/10043* (2013.01); *C12N 2740/10071* (2013.01); *C12N 2810/6081* (2013.01); *C12N 2840/203* (2013.01); *C12Q 2600/106* (2013.01); *C12Q 2600/136* (2013.01); *G01N 2800/52* (2013.01); *G01N 2800/56* (2013.01)

(58) Field of Classification Search

None

See application file for complete search history.

(56) References Cited

U.S. PATENT DOCUMENTS

| | | | |
|---|---|---|---|
| 2006/0029944 A1 | 2/2006 | Huang et al. |
| 2008/0188405 A1 | 8/2008 | Di Fiore et al. |
| 2012/0208188 A1 | 8/2012 | Reya et al. |

FOREIGN PATENT DOCUMENTS

WO WO 2006037462 A2 * 4/2006

OTHER PUBLICATIONS

Stylianou et al., Cancer Reasearch, 2006, vol. 66, pp. 1517-1525.*

Giniger et al., 1997, Grant No. DAMD17-94-J-4266; retrieved from http://www.dtic.mil/cgi-bin/GetTRDoc?AD=ADA341369 on Feb. 20, 2013.*

Druker et al., The New England Journal of Medicine, 2001, vol. 344, pp. 1031-1037.*

Ramaswamy et al., PNAS, 2001, vol. 98, pp. 15149-15154.*

Rennstam et al., Breast Cancer Res Treat, 2010, vol. 122, pp. 315-324.*

Battelli, C., et al., "The RNA-binding protein Musashi-1 regulates neural development through the translational repression of p21WAF-1" Mol Cell Neurosci 31, 85-96 (2006).

Calabretta, B., et al., "The biology of CML blast crisis" Blood 103, 4010-4022 (2004).

Carlesso, N., Aster, J.C., Sklar, J. & Scadden, "Notch1-Induced Delay of Human Hematopoietic Progenitor Cell Differentiation is Associated With Altered Cell Cycle Kinetics," D.T. Blood 1999, 93, 838-48.

Colaluca, I. N., et al., "NUMB controls p53 tumour suppressor activity" Nature 451, 76-80 (2008).

Daley, G. Q., et al., "Induction of chronic myelogenous leukemia in mice by the P210bcr/abl gene of the Philadelphia chromosome" Science 247, 824-830 (1990).

Dash, A. B., et al. "A murine model of CML blast crisis induced by cooperation between BCR/ABL and NUP98/HOXA9" Proc Natl Acad Sci USA 99, 7622-7627 (2002).

Duncan, AW. et al. "Integration of Notch and Wnt signaling in hematopoietic stem cell maintenance," Nat Immunol 2005,6,314-22.

Estrach, S., Ambler, C.A, Lo Celso, C., Hozumi, K. & Watt, F.M. "Jagged 1 is a Beta-catenin target gene required for ectopic hair follicle formation in adult epidermis," Development 2006, 133, 4427-38.

Goldman, J. M., et al., "BCR-ABL in chronic myelogenous leukemia—how does it work?" Acta Haematol 119, 212-217 (2008).

Hellstrom, M. et al. "D114 signalling through Notch1 regulates formation of tip cells during angiogenesis," Nature 2007, 445, 776-80.

Huntly, B.J. et al. "MOZ-TIF2, but not BCR-ABL, confers properties of leukemic stem cells to committed murine hematopoietic prognitors," Cancer Cell 2004, 6, 587-96.

(Continued)

*Primary Examiner* — Michele K Joike

*Assistant Examiner* — Mindy G Brown

(74) *Attorney, Agent, or Firm* — Michael Best & Friedrich LLP

(57) ABSTRACT

Disclosed are methods of predicting responsiveness of a cancer cell to a tyrosine kinase inhibitor, and methods of predicting the risk of progression of a cancer cell to a more aggressive form. Also provided are methods of reducing proliferation or promoting differentiation of a cancer cell having reduced level of Numb or increased level of Msi. Further disclosed are methods of treating a mammalian subject having cancer and methods of assessing an agent for chemotherapeutic potential.

5 Claims, 19 Drawing Sheets

(56) References Cited

OTHER PUBLICATIONS

Imai, T., et al., "The neural RNA-binding protein Musashi1 translationally regulates mammalian numb gene expression by interacting with its mRNA" Mol Cell Biol 21, 3888-3900 (2001).
Jegga, A. G., et al., "Detection and visualization of compositionally similar cis-regulatory element clusters in orthologous and coordinately controlled genes" Genome Res 12, 1408-1417 (2002).
Justice, N., et al., "Lethal giant larvae acts together with numb in notch inhibition and cell fate specification in the Drosophila adult sensory organ precursor lineage" Curr Biol 13, 778-783 (2003).
Knoblich, J. A. "Mechanisms of asymmetric cell division during animal development" Curr Opin Cell Biol 9, 833-841 (1997).
Lai, AY. & Kondo, "Identification of a bone marrow precursor of the earliest thymocytes in adult mouse," M. Proc Natl Acad Sci USA 2007, 104, 6311-6.
Liu, G., et al., "Analysis of gene expression and chemoresistance of CD133+ cancer stem cells in glioblastoma" Mol Cancer 5, 67 (2006).
Mayotte, N., et al., "Oncogenic interaction between BCR-ABL and NUP98-HOXA9 demonstrated by the use of an in vitro purging culture system" Blood 100, 4177-4184 (2002).
Melo, J. V., et al., "Chronic myeloid leukaemia as a model of disease evolution in human cancer" Nat Rev Cancer 7, 441-453 (2007).
Mombaerts, P. et al. "RAG-1-Deficient Mice Have No Mature B and T Lymphocytes" Cell 1992, 68, 869-77.
Nakahara, F., et al., "Hes1 immortalizes committed progenitors and plays a role in blast crisis transition in chronic myelogenous leukemia" Blood 115, 2872-2881 (2010).
Nakamura, M., et al., "A neural RNA-binding protein required for Drosophila adult external sensory organ development" Neuron 13, 67-81 (1994).
NCBI Reference Sequence NM_001005743, (2004).
NCBI Reference Sequence NM_138962.2, (2004).
Neering, S. J., et al., "Leukemia stem cells in a genetically defined murine model of blast-crisis CML" Blood 110, 2578-2585 (2007).
Okabe, M., et al., "Translational repression determines a neuronal potential in Drosophila asymmetric cell division" Nature 411, 94-98 (2001).
Okano, H., et al., "Function of RNA-binding protein Musashi-1 in stem cells" Exp Cell Res 306, 349-356 (2005).
Pear, W. S., et al. "Efficient and rapid induction of a chronic myelogenous leukemia-like myeloproliferative disease in mice receiving P210 bcr/abl-transduced bone marrow" Blood 92, 3780-3792 (1998).
Pece, S., et al., "Loss of negative regulation by Numb over Notch is relevant to human breast carcinogenesis" J Cell Biol 167, 215-221 (2004).
Radich, J. P., et al. "Gene expression changes associated with progression and response in chronic myeloid leukemia" Proc Natl Acad Sci USA 103, 2794-2799 (2006).
Ren, R. "Mechanisms of BCR-ABL in the pathogenesis of chronic myelogenous leukaemia" Nat Rev Cancer 5, 172-183 (2005).
Rizzo et al., "Cross-talk between Notch and the Estrogen Receptor in Breast Cancer Suggests Novel Therapeutic Approaches" Caner Res. Jul. 1, 2008, vol. 68, No. 13, p. 5226-5235.
Sakakibara, S., et al., "RNA-binding protein Musashi family: roles for CNS stem cells and a subpopulation of ependymal cells revealed by targeted disruption and antisense ablation" Proc Natl Acad Sci USA 99, 15194-15199 (2002).
Shen, Q., et al., "Asymmetric Numb distribution is critical for asymmetric cell division of mouse cerebral cortical stem cells and neuroblasts" Development 129, 4843-4853 (2002).
Spana, E. P., et al., "Numb antagonizes Notch signaling to specify sibling neuron cell fates" Neuron 17, 21-26 (1996).
Sureban et al., "Knockdown of RNA binding protein musashi-1 leads to tumor regression in vivo" Gastroenterology. May 2008, vol. 134, No. 5, p. 1448-1458.
Taniwaki, T., et al., "Characterization of an exchangeable gene trap using pU-17 carrying a stop codon-beta geo cassette" Dev Growth Differ 47, 163-172 (2005).
Verdi et al., "Mammalian NUMB is an evolutionarily conserved signaling adapter protein that specifies cell fate" Curr Biol. Sep. 1, 1996, vol. 6, No. 9, p. 1134-1145.
Wakamatsu, Y., et al., "NUMB localizes in the basal cortex of mitotic avian neuroepithelial cells and modulates neuronal differentiation by binding to NOTCH-1" Neuron 23, 71-81 (1999).
Wang, H., et al., "Polo inhibits progenitor self-renewal and regulates Numb asymmetry by phosphorylating Pon" Nature 449, 96-100 (2007).
Witte, O. "The role of Bcr-Abl in chronic myeloid leukemia and stem cell biology" Semin Hematol 38, 3-8 (2001).
Wu, M., et al., "Imaging hematopoietic precursor division in real time" Cell Stem Cell 1, 541-554 (2007).
Zhao, C. et al. "Loss of Beta-Catenin Impairs the Renewal of Normal and CML Stem Cells in Vivo," Cancer Cell 2007, 12, 528-41.
PCT/US2010/035039 International Preliminary Report on Patentability and Written Opinion dated Nov. 24, 2011 (9 pages).
PCT/US2010/035039 International Search Report dated Oct. 15, 2010 (3 pages).

* cited by examiner

```
SEQUENCE LISTING

<160> NUMBER OF SEQ ID NOS: 30

<210> SEQ ID NO 1
<211> LENGTH: 23
<212> TYPE: DNA
<213> ORGANISM: Artificial Sequence
<220> FEATURE:
<223> OTHER INFORMATION: Synthetic

<400> SEQUENCE: 1

atgagttgcc ttccactatg cag                                              23


<210> SEQ ID NO 2
<211> LENGTH: 23
<212> TYPE: DNA
<213> ORGANISM: Artificial Sequence
<220> FEATURE:
<223> OTHER INFORMATION: Synthetic

<400> SEQUENCE: 2

tgctgaaggc actggtgatc tgg                                              23


<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3

atggatgcct tcatgctggg t                                                21


<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4

ctccgctcta cacggaattc g                                                21


<210> SEQ ID NO 5
<211> LENGTH: 21
<212> TYPE: DNA
<213> ORGANISM: Artificial Sequence
```

```
<220> FEATURE:
<223> OTHER INFORMATION: Synthetic

<400> SEQUENCE: 5

tgccatacac catggatgcg t                                              21


<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6

gtagcctctg ccataggttg c                                              21


<210> SEQ ID NO 7
<211> LENGTH: 23
<212> TYPE: DNA
<213> ORGANISM: Artificial Sequence
<220> FEATURE:
<223> OTHER INFORMATION: Synthetic

<400> SEQUENCE: 7

accggcctgt atgctatcca gaa                                            23


<210> SEQ ID NO 8
<211> LENGTH: 22
<212> TYPE: DNA
<213> ORGANISM: Artificial Sequence
<220> FEATURE:
<223> OTHER INFORMATION: Synthetic

<400> SEQUENCE: 8

aatgtgaggc gggtggaact gt                                             22


<210> SEQ ID NO 9
<211> LENGTH: 22
<212> TYPE: DNA
<213> ORGANISM: Artificial Sequence
<220> FEATURE:
<223> OTHER INFORMATION: Synthetic

<400> SEQUENCE: 9

cccagatagc cttagagact at                                             22


<210> SEQ ID NO 10
<211> LENGTH: 22
<212> TYPE: DNA
<213> ORGANISM: Artificial Sequence
<220> FEATURE:
<223> OTHER INFORMATION: Synthetic

<400> SEQUENCE: 10

ctgtgccaga gtccttcgat ag                                             22


<210> SEQ ID NO 11
<211> LENGTH: 1956
<212> TYPE: DNA
<213> ORGANISM: Homo sapiens

<400> SEQUENCE: 11

atgaacaaat tacggcaaag ttttaggaga aagaaggatg tttatgttcc agaggccagt     60

cgtccacatc agtggcagac agatgaagaa ggcgttcgca ccggaaaatg tagcttcccg    120
```

```
gttaagtacc ttggccatgt agaagttgat gaatcaagag gaatgcacat ctgtgaagat    180

gctgtaaaaa gattgaaagc tgaaaggaag ttcttcaaag gcttctttgg aaaaactgga    240

aagaaagcag ttaaagcagt tctgtgggtc tcagcagatg gactcagagt tgtggatgaa    300

aaaactaagg acctcatagt tgaccagacg atagagaaag tttctttctg tgccccagac    360

aggaactttg atagagcctt ttcttacata tgccgtgatg gcaccactcg tcgctggatc    420

tgtcactgct tcatggctgt caaggacaca ggtgaaaggt tgagccatgc agtaggctgt    480

gcttttgcag cctgtttaga gcgcaagcag aagcgggaga aggaatgtgg agtgactgct    540

acttttgatg ctagtcggac cacttttaca agagaaggat cattccgtgt cacaacagcc    600

actgaacaag cagaaagaga ggagatcatg aaacaaatgc aagatgccaa gaaagctgaa    660

acagataaga tagtcgttgg ttcatcagtt gcccctggca acactgcccc atccccatcc    720

tctcccacct ctcctacttc tgatgccacg acctctctgg agatgaacaa tcctcatgcc    780

atcccacgcc ggcatgctcc aattgaacag cttgctcgcc aaggctcttt ccgaggtttt    840

cctgctctta gccagaagat gtcacccttt aaacgccaac tatccctacg catcaatgag    900

ttgccttcca ctatgcagag gaagactgat ttccccatta aaaatgcagt gccagaagta    960

gaaggggagg cagagagcat cagctccctg tgctcacaga tcaccaatgc cttcagcaca   1020

cctgaggacc ccttctcatc tgctccgatg accaaaccag tgacagtggt ggcaccacaa   1080

tctcctacct tccaagctaa tggcactgac tcagccttcc atgtgcttgc taagccagcc   1140

catactgctc tagcacccgt agcaatgcct gtgcgtgaaa ccaacccttg ggcccatgcc   1200

cctgatgctg ctaacaagga aattgcagcc acatgttcgg ggaccgagtg gggtcaatct   1260

tctggtgctg cctctccagg tctcttccag gccggtcata gacgtactcc ctctgaggcc   1320

gaccgatggt tagaagaggt gtctaagagc gtccgggctc agcagcccca ggcctcagct   1380

gctcctctgc agccagttct ccagcctcct ccacccactg ccatctccca gccagcatca   1440

cctttccaag ggaatgcatt cctcacctct cagcctgtgc cagtgggtgt ggtcccagcc   1500

ctgcaaccag cctttgtccc tgcccagtcc tatcctgtgg ccaatggaat gccctatcca   1560

gcccctaatg tgcctgtggt gggcatcact ccctcccaga tggtggccaa cgtatttggc   1620

actgcaggcc accctcaggc tgcccatccc catcagtcac ccagcctggt caggcagcag   1680

acattccctc actacgaggc aagcagtgct accaccagtc ccttctttaa gcctcctgct   1740

cagcacctca acggttctgc agctttcaat ggtgtagatg atggcaggtt ggcctcagca   1800

gacaggcata cagaggttcc tacaggcacc tgcccagtgg atccttttga agcccagtgg   1860

gctgcattag aaaataagtc caagcagcgt actaatccct cccctaccaa ccctttctcc   1920

agtgacttac agaagacgtt tgaaattgaa ctttaa                             1956
```

<210> SEQ ID NO 12
<211> LENGTH: 651
<212> TYPE: PRT
<213> ORGANISM: Homo sapiens

<400> SEQUENCE: 12

```
Met Asn Lys Leu Arg Gln Ser Phe Arg Arg Lys Lys Asp Val Tyr Val
1               5                   10                  15

Pro Glu Ala Ser Arg Pro His Gln Trp Gln Thr Asp Glu Glu Gly Val
            20                  25                  30

Arg Thr Gly Lys Cys Ser Phe Pro Val Lys Tyr Leu Gly His Val Glu
        35                  40                  45
```

```
Val Asp Glu Ser Arg Gly Met His Ile Cys Glu Asp Ala Val Lys Arg
    50                  55                  60

Leu Lys Ala Glu Arg Lys Phe Phe Lys Gly Phe Phe Gly Lys Thr Gly
65                  70                  75                  80

Lys Lys Ala Val Lys Ala Val Leu Trp Val Ser Ala Asp Gly Leu Arg
                85                  90                  95

Val Val Asp Glu Lys Thr Lys Asp Leu Ile Val Asp Gln Thr Ile Glu
            100                 105                 110

Lys Val Ser Phe Cys Ala Pro Asp Arg Asn Phe Asp Arg Ala Phe Ser
        115                 120                 125

Tyr Ile Cys Arg Asp Gly Thr Thr Arg Arg Trp Ile Cys His Cys Phe
    130                 135                 140

Met Ala Val Lys Asp Thr Gly Glu Arg Leu Ser His Ala Val Gly Cys
145                 150                 155                 160

Ala Phe Ala Ala Cys Leu Glu Arg Lys Gln Lys Arg Glu Lys Glu Cys
                165                 170                 175

Gly Val Thr Ala Thr Phe Asp Ala Ser Arg Thr Thr Phe Thr Arg Glu
            180                 185                 190

Gly Ser Phe Arg Val Thr Thr Ala Thr Glu Gln Ala Glu Arg Glu Glu
        195                 200                 205

Ile Met Lys Gln Met Gln Asp Ala Lys Lys Ala Glu Thr Asp Lys Ile
    210                 215                 220

Val Val Gly Ser Ser Val Ala Pro Gly Asn Thr Ala Pro Ser Pro Ser
225                 230                 235                 240

Ser Pro Thr Ser Pro Thr Ser Asp Ala Thr Thr Ser Leu Glu Met Asn
                245                 250                 255

Asn Pro His Ala Ile Pro Arg Arg His Ala Pro Ile Glu Gln Leu Ala
            260                 265                 270

Arg Gln Gly Ser Phe Arg Gly Phe Pro Ala Leu Ser Gln Lys Met Ser
        275                 280                 285

Pro Phe Lys Arg Gln Leu Ser Leu Arg Ile Asn Glu Leu Pro Ser Thr
    290                 295                 300

Met Gln Arg Lys Thr Asp Phe Pro Ile Lys Asn Ala Val Pro Glu Val
305                 310                 315                 320

Glu Gly Glu Ala Glu Ser Ile Ser Ser Leu Cys Ser Gln Ile Thr Asn
                325                 330                 335

Ala Phe Ser Thr Pro Glu Asp Pro Phe Ser Ser Ala Pro Met Thr Lys
            340                 345                 350

Pro Val Thr Val Val Ala Pro Gln Ser Pro Thr Phe Gln Ala Asn Gly
        355                 360                 365

Thr Asp Ser Ala Phe His Val Leu Ala Lys Pro Ala His Thr Ala Leu
    370                 375                 380

Ala Pro Val Ala Met Pro Val Arg Glu Thr Asn Pro Trp Ala His Ala
385                 390                 395                 400

Pro Asp Ala Ala Asn Lys Glu Ile Ala Ala Thr Cys Ser Gly Thr Glu
                405                 410                 415

Trp Gly Gln Ser Ser Gly Ala Ala Ser Pro Gly Leu Phe Gln Ala Gly
            420                 425                 430

His Arg Arg Thr Pro Ser Glu Ala Asp Arg Trp Leu Glu Glu Val Ser
        435                 440                 445

Lys Ser Val Arg Ala Gln Gln Pro Gln Ala Ser Ala Ala Pro Leu Gln
    450                 455                 460

Pro Val Leu Gln Pro Pro Pro Pro Thr Ala Ile Ser Gln Pro Ala Ser
```

```
465                 470                 475                 480

Pro Phe Gln Gly Asn Ala Phe Leu Thr Ser Gln Pro Val Pro Val Gly
                485                 490                 495

Val Val Pro Ala Leu Gln Pro Ala Phe Val Pro Ala Gln Ser Tyr Pro
            500                 505                 510

Val Ala Asn Gly Met Pro Tyr Pro Ala Pro Asn Val Pro Val Val Gly
        515                 520                 525

Ile Thr Pro Ser Gln Met Val Ala Asn Val Phe Gly Thr Ala Gly His
    530                 535                 540

Pro Gln Ala Ala His Pro His Gln Ser Pro Ser Leu Val Arg Gln Gln
545                 550                 555                 560

Thr Phe Pro His Tyr Glu Ala Ser Ser Ala Thr Thr Ser Pro Phe Phe
                565                 570                 575

Lys Pro Pro Ala Gln His Leu Asn Gly Ser Ala Ala Phe Asn Gly Val
            580                 585                 590

Asp Asp Gly Arg Leu Ala Ser Ala Asp Arg His Thr Glu Val Pro Thr
        595                 600                 605

Gly Thr Cys Pro Val Asp Pro Phe Glu Ala Gln Trp Ala Ala Leu Glu
    610                 615                 620

Asn Lys Ser Lys Gln Arg Thr Asn Pro Ser Pro Thr Asn Pro Phe Ser
625                 630                 635                 640

Ser Asp Leu Gln Lys Thr Phe Glu Ile Glu Leu
                645                 650


<210> SEQ ID NO 13
<211> LENGTH: 1812
<212> TYPE: DNA
<213> ORGANISM: Homo sapiens

<400> SEQUENCE: 13

atgaacaaat tacggcaaag ttttaggaga aagaaggatg tttatgttcc agaggccagt      60

cgtccacatc agtggcagac agatgaagaa ggcgttcgca ccggaaaatg tagcttcccg     120

gttaagtacc ttggccatgt agaagttgat gaatcaagag gaatgcacat ctgtgaagat     180

gctgtaaaaa gattgaaagc tgaaaggaag ttcttcaaag gcttctttgg aaaaactgga     240

aagaaagcag ttaaagcagt tctgtgggtc tcagcagatg gactcagagt tgtggatgaa     300

aaaactaagg acctcatagt tgaccagacg atagagaaag tttctttctg tgccccagac     360

aggaactttg atagagcctt ttcttacata tgccgtgatg gcaccactcg tcgctggatc     420

tgtcactgct tcatggctgt caaggacaca ggtgaaaggt tgagccatgc agtaggctgt     480

gcttttgcag cctgtttaga gcgcaagcag aagcgggaga aggaatgtgg agtgactgct     540

acttttgatg ctagtcggac cacttttaca agagaaggat cattccgtgt cacaacagcc     600

actgaacaag cagaaagaga ggagatcatg aaacaaatgc aagatgccaa gaaagctgaa     660

acagataaga tagtcgttgg ttcatcagtt gcccctggca acactgcccc atccccatcc     720

tctcccacct ctcctacttc tgatgccacg acctctctgg agatgaacaa tcctcatgcc     780

atcccacgcc ggcatgctcc aattgaacag cttgctcgcc aaggctcttt ccgaggtttt     840

cctgctctta gccagaagat gtcacccttt aaacgccaac tatccctacg catcaatgag     900

ttgccttcca ctatgcagag gaagactgat ttccccatta aaaatgcagt gccagaagta     960

gaaggggagg cagagagcat cagctccctg tgctcacaga tcaccaatgc cttcagcaca    1020

cctgaggacc ccttctcatc tgctccgatg accaaaccag tgacagtggt ggcaccacaa    1080
```

```
tctcctacct tccaagggac cgagtggggt caatcttctg gtgctgcctc tccaggtctc   1140

ttccaggccg gtcatagacg tactccctct gaggccgacc gatggttaga agaggtgtct   1200

aagagcgtcc gggctcagca gccccaggcc tcagctgctc ctctgcagcc agttctccag   1260

cctcctccac ccactgccat ctcccagcca gcatcacctt tccaagggaa tgcattcctc   1320

acctctcagc ctgtgccagt gggtgtggtc ccagccctgc aaccagcctt tgtccctgcc   1380

cagtcctatc ctgtggccaa tggaatgccc tatccagccc ctaatgtgcc tgtggtgggc   1440

atcactccct cccagatggt ggccaacgta tttggcactg caggccaccc tcaggctgcc   1500

catccccatc agtcacccag cctggtcagg cagcagacat tccctcacta cgaggcaagc   1560

agtgctacca ccagtccctt ctttaagcct cctgctcagc acctcaacgg ttctgcagct   1620

ttcaatggtg tagatgatgg caggttggcc tcagcagaca ggcatacaga ggttcctaca   1680

ggcacctgcc cagtggatcc ttttgaagcc cagtgggctg cattagaaaa taagtccaag   1740

cagcgtacta atccctcccc taccaaccct ttctccagtg acttacagaa gacgtttgaa   1800

attgaacttt aa                                                       1812
```

<210> SEQ ID NO 14
<211> LENGTH: 603
<212> TYPE: PRT
<213> ORGANISM: Homo sapiens

<400> SEQUENCE: 14

```
Met Asn Lys Leu Arg Gln Ser Phe Arg Arg Lys Lys Asp Val Tyr Val
1               5                   10                  15

Pro Glu Ala Ser Arg Pro His Gln Trp Gln Thr Asp Glu Glu Gly Val
            20                  25                  30

Arg Thr Gly Lys Cys Ser Phe Pro Val Lys Tyr Leu Gly His Val Glu
        35                  40                  45

Val Asp Glu Ser Arg Gly Met His Ile Cys Glu Asp Ala Val Lys Arg
    50                  55                  60

Leu Lys Ala Glu Arg Lys Phe Phe Lys Gly Phe Phe Gly Lys Thr Gly
65                  70                  75                  80

Lys Lys Ala Val Lys Ala Val Leu Trp Val Ser Ala Asp Gly Leu Arg
                85                  90                  95

Val Val Asp Glu Lys Thr Lys Asp Leu Ile Val Asp Gln Thr Ile Glu
            100                 105                 110

Lys Val Ser Phe Cys Ala Pro Asp Arg Asn Phe Asp Arg Ala Phe Ser
        115                 120                 125

Tyr Ile Cys Arg Asp Gly Thr Thr Arg Arg Trp Ile Cys His Cys Phe
    130                 135                 140

Met Ala Val Lys Asp Thr Gly Glu Arg Leu Ser His Ala Val Gly Cys
145                 150                 155                 160

Ala Phe Ala Ala Cys Leu Glu Arg Lys Gln Lys Arg Glu Lys Glu Cys
                165                 170                 175

Gly Val Thr Ala Thr Phe Asp Ala Ser Arg Thr Thr Phe Thr Arg Glu
            180                 185                 190

Gly Ser Phe Arg Val Thr Thr Ala Thr Glu Gln Ala Glu Arg Glu Glu
        195                 200                 205

Ile Met Lys Gln Met Gln Asp Ala Lys Lys Ala Glu Thr Asp Lys Ile
    210                 215                 220

Val Val Gly Ser Ser Val Ala Pro Gly Asn Thr Ala Pro Ser Pro Ser
225                 230                 235                 240
```

```
Ser Pro Thr Ser Pro Thr Ser Asp Ala Thr Thr Ser Leu Glu Met Asn
            245                 250                 255

Asn Pro His Ala Ile Pro Arg Arg His Ala Pro Ile Glu Gln Leu Ala
        260                 265                 270

Arg Gln Gly Ser Phe Arg Gly Phe Pro Ala Leu Ser Gln Lys Met Ser
        275                 280                 285

Pro Phe Lys Arg Gln Leu Ser Leu Arg Ile Asn Glu Leu Pro Ser Thr
    290                 295                 300

Met Gln Arg Lys Thr Asp Phe Pro Ile Lys Asn Ala Val Pro Glu Val
305                 310                 315                 320

Glu Gly Glu Ala Glu Ser Ile Ser Ser Leu Cys Ser Gln Ile Thr Asn
            325                 330                 335

Ala Phe Ser Thr Pro Glu Asp Pro Phe Ser Ser Ala Pro Met Thr Lys
        340                 345                 350

Pro Val Thr Val Val Ala Pro Gln Ser Pro Thr Phe Gln Gly Thr Glu
        355                 360                 365

Trp Gly Gln Ser Ser Gly Ala Ala Ser Pro Gly Leu Phe Gln Ala Gly
    370                 375                 380

His Arg Arg Thr Pro Ser Glu Ala Asp Arg Trp Leu Glu Glu Val Ser
385                 390                 395                 400

Lys Ser Val Arg Ala Gln Gln Pro Gln Ala Ser Ala Ala Pro Leu Gln
            405                 410                 415

Pro Val Leu Gln Pro Pro Pro Pro Thr Ala Ile Ser Gln Pro Ala Ser
        420                 425                 430

Pro Phe Gln Gly Asn Ala Phe Leu Thr Ser Gln Pro Val Pro Val Gly
        435                 440                 445

Val Val Pro Ala Leu Gln Pro Ala Phe Val Pro Ala Gln Ser Tyr Pro
    450                 455                 460

Val Ala Asn Gly Met Pro Tyr Pro Ala Pro Asn Val Pro Val Val Gly
465                 470                 475                 480

Ile Thr Pro Ser Gln Met Val Ala Asn Val Phe Gly Thr Ala Gly His
            485                 490                 495

Pro Gln Ala Ala His Pro His Gln Ser Pro Ser Leu Val Arg Gln Gln
        500                 505                 510

Thr Phe Pro His Tyr Glu Ala Ser Ser Ala Thr Thr Ser Pro Phe Phe
        515                 520                 525

Lys Pro Pro Ala Gln His Leu Asn Gly Ser Ala Ala Phe Asn Gly Val
    530                 535                 540

Asp Asp Gly Arg Leu Ala Ser Ala Asp Arg His Thr Glu Val Pro Thr
545                 550                 555                 560

Gly Thr Cys Pro Val Asp Pro Phe Glu Ala Gln Trp Ala Ala Leu Glu
            565                 570                 575

Asn Lys Ser Lys Gln Arg Thr Asn Pro Ser Pro Thr Asn Pro Phe Ser
        580                 585                 590

Ser Asp Leu Gln Lys Thr Phe Glu Ile Glu Leu
        595                 600

<210> SEQ ID NO 15
<211> LENGTH: 1923
<212> TYPE: DNA
<213> ORGANISM: Homo sapiens

<400> SEQUENCE: 15

atgaacaaat tacggcaaag ttttaggaga aagaaggatg tttatgttcc agaggccagt      60
```

-continued

```
cgtccacatc agtggcagac agatgaagaa ggcgttcgca ccggaaaatg tagcttcccg    120

gttaagtacc ttggccatgt agaagttgat gaatcaagag gaatgcacat ctgtgaagat    180

gctgtaaaaa gattgaaagc tactggaaag aaagcagtta aagcagttct gtgggtctca    240

gcagatggac tcagagttgt ggatgaaaaa actaaggacc tcatagttga ccagacgata    300

gagaaagttt ctttctgtgc ccagacagg aactttgata gagccttttc ttacatatgc    360

cgtgatggca ccactcgtcg ctggatctgt cactgcttca tggctgtcaa ggacacaggt    420

gaaaggttga gccatgcagt aggctgtgct tttgcagcct gtttagagcg caagcagaag    480

cgggagaagg aatgtggagt gactgctact tttgatgcta gtcggaccac ttttacaaga    540

gaaggatcat tccgtgtcac aacagccact gaacaagcag aaagagagga gatcatgaaa    600

caaatgcaag atgccaagaa agctgaaaca gataagatag tcgttggttc atcagttgcc    660

cctggcaaca ctgccccatc cccatcctct cccacctctc ctacttctga tgccacgacc    720

tctctggaga tgaacaatcc tcatgccatc ccacgccggc atgctccaat tgaacagctt    780

gctcgccaag gctctttccg aggttttcct gctcttagcc agaagatgtc accctttaaa    840

cgccaactat ccctacgcat caatgagttg ccttccacta tgcagaggaa gactgatttc    900

cccattaaaa atgcagtgcc agaagtagaa ggggaggcag agagcatcag ctccctgtgc    960

tcacagatca ccaatgcctt cagcacacct gaggacccct tctcatctgc tccgatgacc   1020

aaaccagtga cagtggtggc accacaatct cctaccttcc aagctaatgg cactgactca   1080

gccttccatg tgcttgctaa gccagcccat actgctctag cacccgtagc aatgcctgtg   1140

cgtgaaacca acccttgggc ccatgcccct gatgctgcta acaaggaaat tgcagccaca   1200

tgttcgggga ccgagtgggg tcaatcttct ggtgctgcct ctccaggtct cttccaggcc   1260

ggtcatagac gtactccctc tgaggccgac cgatggttag aagaggtgtc taagagcgtc   1320

cgggctcagc agccccaggc ctcagctgct cctctgcagc cagttctcca gcctcctcca   1380

cccactgcca tctcccagcc agcatcacct ttccaaggga atgcattcct cacctctcag   1440

cctgtgccag tgggtgtggt cccagccctg caaccagcct ttgtccctgc ccagtcctat   1500

cctgtggcca atggaatgcc ctatccagcc cctaatgtgc ctgtggtggg catcactccc   1560

tcccagatgg tggccaacgt atttggcact gcaggccacc ctcaggctgc ccatccccat   1620

cagtcaccca gcctggtcag gcagcagaca ttccctcact acgaggcaag cagtgctacc   1680

accagtccct tctttaagcc tcctgctcag cacctcaacg gttctgcagc tttcaatggt   1740

gtagatgatg gcaggttggc ctcagcagac aggcatacag aggttcctac aggcacctgc   1800

ccagtggatc cttttgaagc ccagtgggct gcattagaaa ataagtccaa gcagcgtact   1860

aatccctccc ctaccaaccc tttctccagt gacttacaga agacgtttga aattgaactt   1920

taa                                                                 1923
```

```
<210> SEQ ID NO 16
<211> LENGTH: 640
<212> TYPE: PRT
<213> ORGANISM: Homo sapiens

<400> SEQUENCE: 16

Met Asn Lys Leu Arg Gln Ser Phe Arg Arg Lys Lys Asp Val Tyr Val
1               5                   10                  15

Pro Glu Ala Ser Arg Pro His Gln Trp Gln Thr Asp Glu Glu Gly Val
            20                  25                  30

Arg Thr Gly Lys Cys Ser Phe Pro Val Lys Tyr Leu Gly His Val Glu
```

```
        35                  40                  45

Val Asp Glu Ser Arg Gly Met His Ile Cys Glu Asp Ala Val Lys Arg
    50                  55                  60

Leu Lys Ala Thr Gly Lys Lys Ala Val Lys Ala Val Leu Trp Val Ser
65                  70                  75                  80

Ala Asp Gly Leu Arg Val Val Asp Glu Lys Thr Lys Asp Leu Ile Val
                85                  90                  95

Asp Gln Thr Ile Glu Lys Val Ser Phe Cys Ala Pro Asp Arg Asn Phe
            100                 105                 110

Asp Arg Ala Phe Ser Tyr Ile Cys Arg Asp Gly Thr Thr Arg Arg Trp
        115                 120                 125

Ile Cys His Cys Phe Met Ala Val Lys Asp Thr Gly Glu Arg Leu Ser
    130                 135                 140

His Ala Val Gly Cys Ala Phe Ala Ala Cys Leu Glu Arg Lys Gln Lys
145                 150                 155                 160

Arg Glu Lys Glu Cys Gly Val Thr Ala Thr Phe Asp Ala Ser Arg Thr
                165                 170                 175

Thr Phe Thr Arg Glu Gly Ser Phe Arg Val Thr Thr Ala Thr Glu Gln
            180                 185                 190

Ala Glu Arg Glu Glu Ile Met Lys Gln Met Gln Asp Ala Lys Lys Ala
        195                 200                 205

Glu Thr Asp Lys Ile Val Val Gly Ser Ser Val Ala Pro Gly Asn Thr
    210                 215                 220

Ala Pro Ser Pro Ser Ser Pro Thr Ser Pro Thr Ser Asp Ala Thr Thr
225                 230                 235                 240

Ser Leu Glu Met Asn Asn Pro His Ala Ile Pro Arg Arg His Ala Pro
                245                 250                 255

Ile Glu Gln Leu Ala Arg Gln Gly Ser Phe Arg Gly Phe Pro Ala Leu
            260                 265                 270

Ser Gln Lys Met Ser Pro Phe Lys Arg Gln Leu Ser Leu Arg Ile Asn
        275                 280                 285

Glu Leu Pro Ser Thr Met Gln Arg Lys Thr Asp Phe Pro Ile Lys Asn
    290                 295                 300

Ala Val Pro Glu Val Glu Gly Glu Ala Glu Ser Ile Ser Ser Leu Cys
305                 310                 315                 320

Ser Gln Ile Thr Asn Ala Phe Ser Thr Pro Glu Asp Pro Phe Ser Ser
                325                 330                 335

Ala Pro Met Thr Lys Pro Val Thr Val Val Ala Pro Gln Ser Pro Thr
            340                 345                 350

Phe Gln Ala Asn Gly Thr Asp Ser Ala Phe His Val Leu Ala Lys Pro
        355                 360                 365

Ala His Thr Ala Leu Ala Pro Val Ala Met Pro Val Arg Glu Thr Asn
    370                 375                 380

Pro Trp Ala His Ala Pro Asp Ala Ala Asn Lys Glu Ile Ala Ala Thr
385                 390                 395                 400

Cys Ser Gly Thr Glu Trp Gly Gln Ser Ser Gly Ala Ala Ser Pro Gly
                405                 410                 415

Leu Phe Gln Ala Gly His Arg Arg Thr Pro Ser Glu Ala Asp Arg Trp
            420                 425                 430

Leu Glu Glu Val Ser Lys Ser Val Arg Ala Gln Gln Pro Gln Ala Ser
        435                 440                 445

Ala Ala Pro Leu Gln Pro Val Leu Gln Pro Pro Pro Pro Thr Ala Ile
    450                 455                 460
```

```
Ser Gln Pro Ala Ser Pro Phe Gln Gly Asn Ala Phe Leu Thr Ser Gln
465                 470                 475                 480

Pro Val Pro Val Gly Val Val Pro Ala Leu Gln Pro Ala Phe Val Pro
                485                 490                 495

Ala Gln Ser Tyr Pro Val Ala Asn Gly Met Pro Tyr Pro Ala Pro Asn
            500                 505                 510

Val Pro Val Val Gly Ile Thr Pro Ser Gln Met Val Ala Asn Val Phe
        515                 520                 525

Gly Thr Ala Gly His Pro Gln Ala Ala His Pro His Gln Ser Pro Ser
    530                 535                 540

Leu Val Arg Gln Gln Thr Phe Pro His Tyr Glu Ala Ser Ser Ala Thr
545                 550                 555                 560

Thr Ser Pro Phe Phe Lys Pro Pro Ala Gln His Leu Asn Gly Ser Ala
                565                 570                 575

Ala Phe Asn Gly Val Asp Asp Gly Arg Leu Ala Ser Ala Asp Arg His
            580                 585                 590

Thr Glu Val Pro Thr Gly Thr Cys Pro Val Asp Pro Phe Glu Ala Gln
        595                 600                 605

Trp Ala Ala Leu Glu Asn Lys Ser Lys Gln Arg Thr Asn Pro Ser Pro
    610                 615                 620

Thr Asn Pro Phe Ser Ser Asp Leu Gln Lys Thr Phe Glu Ile Glu Leu
625                 630                 635                 640


<210> SEQ ID NO 17
<211> LENGTH: 1779
<212> TYPE: DNA
<213> ORGANISM: Homo sapiens

<400> SEQUENCE: 17

atgaacaaat tacggcaaag ttttaggaga aagaaggatg tttatgttcc agaggccagt      60

cgtccacatc agtggcagac agatgaagaa ggcgttcgca ccggaaaatg tagcttcccg     120

gttaagtacc ttggccatgt agaagttgat gaatcaagag gaatgcacat ctgtgaagat     180

gctgtaaaaa gattgaaagc tactggaaag aaagcagtta aagcagttct gtgggtctca     240

gcagatggac tcagagttgt ggatgaaaaa actaaggacc tcatagttga ccagacgata     300

gagaaagttt ctttctgtgc cccagacagg aactttgata gagccttttc ttacatatgc     360

cgtgatggca ccactcgtcg ctggatctgt cactgcttca tggctgtcaa ggacacaggt     420

gaaaggttga gccatgcagt aggctgtgct tttgcagcct gtttagagcg caagcagaag     480

cgggagaagg aatgtggagt gactgctact tttgatgcta gtcggaccac ttttacaaga     540

gaaggatcat tccgtgtcac aacagccact gaacaagcag aaagagagga gatcatgaaa     600

caaatgcaag atgccaagaa agctgaaaca gataagatag tcgttggttc atcagttgcc     660

cctggcaaca ctgccccatc cccatcctct cccacctctc ctacttctga tgccacgacc     720

tctctggaga tgaacaatcc tcatgccatc ccacgccggc atgctccaat tgaacagctt     780

gctcgccaag gctctttccg aggttttcct gctcttagcc agaagatgtc accctttaaa     840

cgccaactat ccctacgcat caatgagttg ccttccacta tgcagaggaa gactgatttc     900

cccattaaaa atgcagtgcc agaagtagaa ggggaggcag agagcatcag ctccctgtgc     960

tcacagatca ccaatgcctt cagcacacct gaggacccct tctcatctgc tccgatgacc    1020

aaaccagtga cagtggtggc accacaatct cctaccttcc aagggaccga gtggggtcaa    1080

tcttctggtg ctgcctctcc aggtctcttc caggccggtc atagacgtac tccctctgag    1140
```

```
gccgaccgat ggttagaaga ggtgtctaag agcgtccggg ctcagcagcc ccaggcctca   1200

gctgctcctc tgcagccagt tctccagcct cctccaccca ctgccatctc ccagccagca   1260

tcacctttcc aagggaatgc attcctcacc tctcagcctg tgccagtggg tgtggtccca   1320

gccctgcaac cagcctttgt ccctgcccag tcctatcctg tggccaatgg aatgccctat   1380

ccagcccccta atgtgcctgt ggtgggcatc actccctccc agatggtggc caacgtattt   1440

ggcactgcag gccaccctca ggctgcccat ccccatcagt cacccagcct ggtcaggcag   1500

cagacattcc ctcactacga ggcaagcagt gctaccacca gtcccttctt taagcctcct   1560

gctcagcacc tcaacggttc tgcagctttc aatggtgtag atgatggcag gttggcctca   1620

gcagacaggc atacagaggt tcctacaggc acctgcccag tggatccttt tgaagcccag   1680

tgggctgcat tagaaaataa gtccaagcag cgtactaatc cctcccctac caaccctttc   1740

tccagtgact tacagaagac gtttgaaatt gaactttaa                         1779


<210> SEQ ID NO 18
<211> LENGTH: 592
<212> TYPE: PRT
<213> ORGANISM: Homo sapiens

<400> SEQUENCE: 18

Met Asn Lys Leu Arg Gln Ser Phe Arg Arg Lys Lys Asp Val Tyr Val
1               5                   10                  15

Pro Glu Ala Ser Arg Pro His Gln Trp Gln Thr Asp Glu Glu Gly Val
            20                  25                  30

Arg Thr Gly Lys Cys Ser Phe Pro Val Lys Tyr Leu Gly His Val Glu
        35                  40                  45

Val Asp Glu Ser Arg Gly Met His Ile Cys Glu Asp Ala Val Lys Arg
    50                  55                  60

Leu Lys Ala Thr Gly Lys Lys Ala Val Lys Ala Val Leu Trp Val Ser
65                  70                  75                  80

Ala Asp Gly Leu Arg Val Val Asp Glu Lys Thr Lys Asp Leu Ile Val
                85                  90                  95

Asp Gln Thr Ile Glu Lys Val Ser Phe Cys Ala Pro Asp Arg Asn Phe
            100                 105                 110

Asp Arg Ala Phe Ser Tyr Ile Cys Arg Asp Gly Thr Thr Arg Arg Trp
        115                 120                 125

Ile Cys His Cys Phe Met Ala Val Lys Asp Thr Gly Glu Arg Leu Ser
    130                 135                 140

His Ala Val Gly Cys Ala Phe Ala Ala Cys Leu Glu Arg Lys Gln Lys
145                 150                 155                 160

Arg Glu Lys Glu Cys Gly Val Thr Ala Thr Phe Asp Ala Ser Arg Thr
                165                 170                 175

Thr Phe Thr Arg Glu Gly Ser Phe Arg Val Thr Thr Ala Thr Glu Gln
            180                 185                 190

Ala Glu Arg Glu Glu Ile Met Lys Gln Met Gln Asp Ala Lys Lys Ala
        195                 200                 205

Glu Thr Asp Lys Ile Val Val Gly Ser Ser Val Ala Pro Gly Asn Thr
    210                 215                 220

Ala Pro Ser Pro Ser Ser Pro Thr Ser Pro Thr Ser Asp Ala Thr Thr
225                 230                 235                 240

Ser Leu Glu Met Asn Asn Pro His Ala Ile Pro Arg Arg His Ala Pro
                245                 250                 255
```

```
Ile Glu Gln Leu Ala Arg Gln Gly Ser Phe Arg Gly Phe Pro Ala Leu
            260                 265                 270

Ser Gln Lys Met Ser Pro Phe Lys Arg Gln Leu Ser Leu Arg Ile Asn
        275                 280                 285

Glu Leu Pro Ser Thr Met Gln Arg Lys Thr Asp Phe Pro Ile Lys Asn
    290                 295                 300

Ala Val Pro Glu Val Glu Gly Glu Ala Glu Ser Ile Ser Ser Leu Cys
305                 310                 315                 320

Ser Gln Ile Thr Asn Ala Phe Ser Thr Pro Glu Asp Pro Phe Ser Ser
                325                 330                 335

Ala Pro Met Thr Lys Pro Val Thr Val Val Ala Pro Gln Ser Pro Thr
            340                 345                 350

Phe Gln Gly Thr Glu Trp Gly Gln Ser Ser Gly Ala Ala Ser Pro Gly
        355                 360                 365

Leu Phe Gln Ala Gly His Arg Arg Thr Pro Ser Glu Ala Asp Arg Trp
    370                 375                 380

Leu Glu Glu Val Ser Lys Ser Val Arg Ala Gln Gln Pro Gln Ala Ser
385                 390                 395                 400

Ala Ala Pro Leu Gln Pro Val Leu Gln Pro Pro Pro Pro Thr Ala Ile
                405                 410                 415

Ser Gln Pro Ala Ser Pro Phe Gln Gly Asn Ala Phe Leu Thr Ser Gln
            420                 425                 430

Pro Val Pro Val Gly Val Val Pro Ala Leu Gln Pro Ala Phe Val Pro
        435                 440                 445

Ala Gln Ser Tyr Pro Val Ala Asn Gly Met Pro Tyr Pro Ala Pro Asn
    450                 455                 460

Val Pro Val Val Gly Ile Thr Pro Ser Gln Met Val Ala Asn Val Phe
465                 470                 475                 480

Gly Thr Ala Gly His Pro Gln Ala Ala His Pro His Gln Ser Pro Ser
                485                 490                 495

Leu Val Arg Gln Gln Thr Phe Pro His Tyr Glu Ala Ser Ser Ala Thr
            500                 505                 510

Thr Ser Pro Phe Phe Lys Pro Pro Ala Gln His Leu Asn Gly Ser Ala
        515                 520                 525

Ala Phe Asn Gly Val Asp Asp Gly Arg Leu Ala Ser Ala Asp Arg His
    530                 535                 540

Thr Glu Val Pro Thr Gly Thr Cys Pro Val Asp Pro Phe Glu Ala Gln
545                 550                 555                 560

Trp Ala Ala Leu Glu Asn Lys Ser Lys Gln Arg Thr Asn Pro Ser Pro
                565                 570                 575

Thr Asn Pro Phe Ser Ser Asp Leu Gln Lys Thr Phe Glu Ile Glu Leu
            580                 585                 590


<210> SEQ ID NO 19
<211> LENGTH: 1779
<212> TYPE: DNA
<213> ORGANISM: Homo sapiens

<400> SEQUENCE: 19

atgaacaaat tacggcaaag ttttaggaga aagaaggatg tttatgttcc agaggccagt      60

cgtccacatc agtggcagac agatgaagaa ggcgttcgca ccggaaaatg tagcttcccg     120

gttaagtacc ttggccatgt agaagttgat gaatcaagag gaatgcacat ctgtgaagat     180

gctgtaaaaa gattgaaagc tactggaaag aaagcagtta aagcagttct gtgggtctca     240
```

```
gcagatggac tcagagttgt ggatgaaaaa actaaggacc tcatagttga ccagacgata    300

gagaaagttt ctttctgtgc cccagacagg aactttgata gagccttttc ttacatatgc    360

cgtgatggca ccactcgtcg ctggatctgt cactgcttca tggctgtcaa ggacacaggt    420

gaaaggttga gccatgcagt aggctgtgct tttgcagcct gtttagagcg caagcagaag    480

cgggagaagg aatgtggagt gactgctact tttgatgcta gtcggaccac ttttacaaga    540

gaaggatcat tccgtgtcac aacagccact gaacaagcag aaagagagga gatcatgaaa    600

caaatgcaag atgccaagaa agctgaaaca gataagatag tcgttggttc atcagttgcc    660

cctggcaaca ctgccccatc cccatcctct cccacctctc ctacttctga tgccacgacc    720

tctctggaga tgaacaatcc tcatgccatc ccacgccggc atgctccaat tgaacagctt    780

gctcgccaag gctctttccg aggttttcct gctcttagcc agaagatgtc accctttaaa    840

cgccaactat ccctacgcat caatgagttg ccttccacta tgcagaggaa gactgatttc    900

cccattaaaa atgcagtgcc agaagtagaa ggggaggcag agagcatcag ctccctgtgc    960

tcacagatca ccaatgcctt cagcacacct gaggacccct tctcatctgc tccgatgacc   1020

aaaccagtga cagtggtggc accacaatct cctaccttcc aagggaccga gtggggtcaa   1080

tcttctggtg ctgcctctcc aggtctcttc caggccggtc atagacgtac tccctctgag   1140

gccgaccgat ggttagaaga ggtgtctaag agcgtccggg ctcagcagcc ccaggcctca   1200

gctgctcctc tgcagccagt tctccagcct cctccaccca ctgccatctc ccagccagca   1260

tcacctttcc aagggaatgc attcctcacc tctcagcctg tgccagtggg tgtggtccca   1320

gccctgcaac cagcctttgt ccctgcccag tcctatcctg tggccaatgg aatgccctat   1380

ccagcccccta atgtgcctgt ggtgggcatc actccctcca agatggtggc caacgtattt   1440

ggcactgcag gccaccctca ggctgcccat ccccatcagt cacccagcct ggtcaggcag   1500

cagacattcc ctcactacga ggcaagcagt gctaccacca gtcccttctt taagcctcct   1560

gctcagcacc tcaacggttc tgcagctttc aatggtgtag atgatggcag gttggcctca   1620

gcagacaggc atacagaggt tcctacaggc acctgcccag tggatccttt tgaagcccag   1680

tgggctgcat tagaaaataa gtccaagcag cgtactaatc cctcccctac caaccctttc   1740

tccagtgact tacagaagac gtttgaaatt gaactttaa                          1779
```

<210> SEQ ID NO 20
<211> LENGTH: 592
<212> TYPE: PRT
<213> ORGANISM: Homo sapiens

<400> SEQUENCE: 20

```
Met Asn Lys Leu Arg Gln Ser Phe Arg Arg Lys Lys Asp Val Tyr Val
1               5                   10                  15

Pro Glu Ala Ser Arg Pro His Gln Trp Gln Thr Asp Glu Glu Gly Val
            20                  25                  30

Arg Thr Gly Lys Cys Ser Phe Pro Val Lys Tyr Leu Gly His Val Glu
        35                  40                  45

Val Asp Glu Ser Arg Gly Met His Ile Cys Glu Asp Ala Val Lys Arg
    50                  55                  60

Leu Lys Ala Thr Gly Lys Lys Ala Val Lys Ala Val Leu Trp Val Ser
65                  70                  75                  80

Ala Asp Gly Leu Arg Val Val Asp Glu Lys Thr Lys Asp Leu Ile Val
                85                  90                  95

Asp Gln Thr Ile Glu Lys Val Ser Phe Cys Ala Pro Asp Arg Asn Phe
```

```
            100                 105                 110

Asp Arg Ala Phe Ser Tyr Ile Cys Arg Asp Gly Thr Thr Arg Arg Trp
        115                 120                 125

Ile Cys His Cys Phe Met Ala Val Lys Asp Thr Gly Glu Arg Leu Ser
    130                 135                 140

His Ala Val Gly Cys Ala Phe Ala Ala Cys Leu Glu Arg Lys Gln Lys
145                 150                 155                 160

Arg Glu Lys Glu Cys Gly Val Thr Ala Thr Phe Asp Ala Ser Arg Thr
                165                 170                 175

Thr Phe Thr Arg Glu Gly Ser Phe Arg Val Thr Thr Ala Thr Glu Gln
            180                 185                 190

Ala Glu Arg Glu Glu Ile Met Lys Gln Met Gln Asp Ala Lys Lys Ala
        195                 200                 205

Glu Thr Asp Lys Ile Val Val Gly Ser Ser Val Ala Pro Gly Asn Thr
    210                 215                 220

Ala Pro Ser Pro Ser Ser Pro Thr Ser Pro Thr Ser Asp Ala Thr Thr
225                 230                 235                 240

Ser Leu Glu Met Asn Asn Pro His Ala Ile Pro Arg Arg His Ala Pro
                245                 250                 255

Ile Glu Gln Leu Ala Arg Gln Gly Ser Phe Arg Gly Phe Pro Ala Leu
            260                 265                 270

Ser Gln Lys Met Ser Pro Phe Lys Arg Gln Leu Ser Leu Arg Ile Asn
        275                 280                 285

Glu Leu Pro Ser Thr Met Gln Arg Lys Thr Asp Phe Pro Ile Lys Asn
    290                 295                 300

Ala Val Pro Glu Val Glu Gly Glu Ala Glu Ser Ile Ser Ser Leu Cys
305                 310                 315                 320

Ser Gln Ile Thr Asn Ala Phe Ser Thr Pro Glu Asp Pro Phe Ser Ser
                325                 330                 335

Ala Pro Met Thr Lys Pro Val Thr Val Val Ala Pro Gln Ser Pro Thr
            340                 345                 350

Phe Gln Gly Thr Glu Trp Gly Gln Ser Ser Gly Ala Ala Ser Pro Gly
        355                 360                 365

Leu Phe Gln Ala Gly His Arg Arg Thr Pro Ser Glu Ala Asp Arg Trp
    370                 375                 380

Leu Glu Glu Val Ser Lys Ser Val Arg Ala Gln Gln Pro Gln Ala Ser
385                 390                 395                 400

Ala Ala Pro Leu Gln Pro Val Leu Gln Pro Pro Pro Pro Thr Ala Ile
                405                 410                 415

Ser Gln Pro Ala Ser Pro Phe Gln Gly Asn Ala Phe Leu Thr Ser Gln
            420                 425                 430

Pro Val Pro Val Gly Val Val Pro Ala Leu Gln Pro Ala Phe Val Pro
        435                 440                 445

Ala Gln Ser Tyr Pro Val Ala Asn Gly Met Pro Tyr Pro Ala Pro Asn
    450                 455                 460

Val Pro Val Val Gly Ile Thr Pro Ser Lys Met Val Ala Asn Val Phe
465                 470                 475                 480

Gly Thr Ala Gly His Pro Gln Ala Ala His Pro His Gln Ser Pro Ser
                485                 490                 495

Leu Val Arg Gln Gln Thr Phe Pro His Tyr Glu Ala Ser Ser Ala Thr
            500                 505                 510

Thr Ser Pro Phe Phe Lys Pro Pro Ala Gln His Leu Asn Gly Ser Ala
        515                 520                 525
```

```
Ala Phe Asn Gly Val Asp Asp Gly Arg Leu Ala Ser Ala Asp Arg His
    530                 535                 540

Thr Glu Val Pro Thr Gly Thr Cys Pro Val Asp Pro Phe Glu Ala Gln
545                 550                 555                 560

Trp Ala Ala Leu Glu Asn Lys Ser Lys Gln Arg Thr Asn Pro Ser Pro
                565                 570                 575

Thr Asn Pro Phe Ser Ser Asp Leu Gln Lys Thr Phe Glu Ile Glu Leu
            580                 585                 590


<210> SEQ ID NO 21
<211> LENGTH: 1962
<212> TYPE: DNA
<213> ORGANISM: Mus musculus

<400> SEQUENCE: 21

atgaacaaac tacggcaaag cttcaggaga aagaaagacg tttatgtccc agaggccagc     60

cgtccacatc agtggcagac agatgaagaa ggagtccgca ctggaaagtg tagcttccca    120

gttaagtacc tcggccacgt agaagttgat gagtcaagag gaatgcacat ctgtgaagat    180

gccgtaaaga gattgaaagc tgaaaggaag ttcttcaaag gcttctttgg aaaaacggga    240

aagaaagcag tgaaggccgt tctgtgggtg tcagcggatg ggctcagagt tgtggacgag    300

aaaactaagg acctcatagt tgaccagaca atagaaaaag tttccttctg tgccccagat    360

aggaactttg acagagcctt ttcttacata tgtcgtgatg gcaccactcg gcgatggatc    420

tgtcattgtt tcatggctgt caaagacacg gggggaaagac tgagccacgc cgtgggctgt    480

gcttttgcag cctgtttaga gcgtaaacag aagcgggaga aggagtgtgg cgtcactgct    540

acttttgatg ccagtagaac cactttcaca agagaaggat cattccgtgt cacaactgcc    600

actgagcaag ccgaaagaga ggagatcatg aaacagttgc aagatgccaa gaaagctgag    660

acagacaaga cagttgttgg tccatcagtg gctcctggca acactgctcc atccccatcc    720

tctcccacct ctcccactcc ggatggcact gcatcttcag agatgaacaa tccccatgct    780

atcccacgcc ggcatgcacc aattgaacag cttgctcgtc aaggctcttt ccggggattt    840

cctgctctta gccagaagat gtcacccttt aaacgccagc tgtccctacg catcaatgag    900

ttgccttcca ctatgcagag gaagaccgat ttcccaataa aaaacacagt gcccgaggtg    960

gaaggagagg ccgagagcat cagctccttg tgttcccaga tcaccagtgc cttcagcacg   1020

ccctctgagg accccttctc ctccgcccca atgaccaaac cagtgacatt ggtggcacca   1080

cagtctcctg tgttacaagc taatggcact gactcagcct cccatgtgct tactgctaag   1140

ccagccaata ctgctctagc acacgtagca atgcctgtcc gtgaaaccaa cccctgggcc   1200

catgtccctg atgctgctaa caaggaaatt gcagccatac atccggggac tgagtggggt   1260

cagtcttctg gtgctgcctc tccaggtctc ttccaggctg gtcacagacg cactccctct   1320

gaagctgacc gctggttaga agaagtgtca aagagtgtgc gggcccagca gcctcaggtc   1380

tcagctgccc ctctgcagcc agttctccag ccgcctccgc ccgccgccat tgcccctcca   1440

gcacctcctt tccaaggaca tgccttcctc acgtcccagc ctgtgcccgt gggtgtggtc   1500

ccaccoctac aaccagcctt tgtccctacc cagtcctacc ctgtggccaa cgggatgccc   1560

tacccagcct ctaatgtgcc tgtagtgggc atcaccccat cccagatggt agccaatgtg   1620

tttggcactg caggccaccc tcagacaact catccacatc agtcgccaag cctggccaag   1680

cagcagacat tccctcaata tgagacaagt agtgctacca ccagtccctt ctttaagcct   1740
```

```
cctgctcagc acctcaatgg ttctgcagct ttcaatggtg tagacaatgg tgggctagcc   1800

tcaggaaaca ggcatgcaga agtccctcca ggcacctgcc cagtggatcc tttcgaagct   1860

cagtgggccg cactagaaag caagtccaag cagcgtacaa atccttctcc taccaaccct   1920

ttctccagtg acttacagaa aacatttgaa atagaacttt ag                      1962


<210> SEQ ID NO 22
<211> LENGTH: 653
<212> TYPE: PRT
<213> ORGANISM: Mus musculus

<400> SEQUENCE: 22

Met Asn Lys Leu Arg Gln Ser Phe Arg Arg Lys Lys Asp Val Tyr Val
1               5                   10                  15

Pro Glu Ala Ser Arg Pro His Gln Trp Gln Thr Asp Glu Glu Gly Val
            20                  25                  30

Arg Thr Gly Lys Cys Ser Phe Pro Val Lys Tyr Leu Gly His Val Glu
        35                  40                  45

Val Asp Glu Ser Arg Gly Met His Ile Cys Glu Asp Ala Val Lys Arg
    50                  55                  60

Leu Lys Ala Glu Arg Lys Phe Phe Lys Gly Phe Phe Gly Lys Thr Gly
65                  70                  75                  80

Lys Lys Ala Val Lys Ala Val Leu Trp Val Ser Ala Asp Gly Leu Arg
                85                  90                  95

Val Val Asp Glu Lys Thr Lys Asp Leu Ile Val Asp Gln Thr Ile Glu
            100                 105                 110

Lys Val Ser Phe Cys Ala Pro Asp Arg Asn Phe Asp Arg Ala Phe Ser
        115                 120                 125

Tyr Ile Cys Arg Asp Gly Thr Thr Arg Arg Trp Ile Cys His Cys Phe
    130                 135                 140

Met Ala Val Lys Asp Thr Gly Glu Arg Leu Ser His Ala Val Gly Cys
145                 150                 155                 160

Ala Phe Ala Ala Cys Leu Glu Arg Lys Gln Lys Arg Glu Lys Glu Cys
                165                 170                 175

Gly Val Thr Ala Thr Phe Asp Ala Ser Arg Thr Thr Phe Thr Arg Glu
            180                 185                 190

Gly Ser Phe Arg Val Thr Thr Ala Thr Glu Gln Ala Glu Arg Glu Glu
        195                 200                 205

Ile Met Lys Gln Leu Gln Asp Ala Lys Lys Ala Glu Thr Asp Lys Thr
    210                 215                 220

Val Val Gly Pro Ser Val Ala Pro Gly Asn Thr Ala Pro Ser Pro Ser
225                 230                 235                 240

Ser Pro Thr Ser Pro Thr Pro Asp Gly Thr Ala Ser Ser Glu Met Asn
                245                 250                 255

Asn Pro His Ala Ile Pro Arg Arg His Ala Pro Ile Glu Gln Leu Ala
            260                 265                 270

Arg Gln Gly Ser Phe Arg Gly Phe Pro Ala Leu Ser Gln Lys Met Ser
        275                 280                 285

Pro Phe Lys Arg Gln Leu Ser Leu Arg Ile Asn Glu Leu Pro Ser Thr
    290                 295                 300

Met Gln Arg Lys Thr Asp Phe Pro Ile Lys Asn Thr Val Pro Glu Val
305                 310                 315                 320

Glu Gly Glu Ala Glu Ser Ile Ser Ser Leu Cys Ser Gln Ile Thr Ser
                325                 330                 335
```

```
Ala Phe Ser Thr Pro Ser Glu Asp Pro Phe Ser Ser Ala Pro Met Thr
            340                 345                 350

Lys Pro Val Thr Leu Val Ala Pro Gln Ser Pro Val Leu Gln Ala Asn
        355                 360                 365

Gly Thr Asp Ser Ala Ser His Val Leu Thr Ala Lys Pro Ala Asn Thr
    370                 375                 380

Ala Leu Ala His Val Ala Met Pro Val Arg Glu Thr Asn Pro Trp Ala
385                 390                 395                 400

His Val Pro Asp Ala Ala Asn Lys Glu Ile Ala Ala Ile His Pro Gly
                405                 410                 415

Thr Glu Trp Gly Gln Ser Ser Gly Ala Ala Ser Pro Gly Leu Phe Gln
            420                 425                 430

Ala Gly His Arg Arg Thr Pro Ser Glu Ala Asp Arg Trp Leu Glu Glu
        435                 440                 445

Val Ser Lys Ser Val Arg Ala Gln Gln Pro Gln Val Ser Ala Ala Pro
    450                 455                 460

Leu Gln Pro Val Leu Gln Pro Pro Pro Pro Ala Ala Ile Ala Pro Pro
465                 470                 475                 480

Ala Pro Pro Phe Gln Gly His Ala Phe Leu Thr Ser Gln Pro Val Pro
                485                 490                 495

Val Gly Val Val Pro Pro Leu Gln Pro Ala Phe Val Pro Thr Gln Ser
            500                 505                 510

Tyr Pro Val Ala Asn Gly Met Pro Tyr Pro Ala Ser Asn Val Pro Val
        515                 520                 525

Val Gly Ile Thr Pro Ser Gln Met Val Ala Asn Val Phe Gly Thr Ala
    530                 535                 540

Gly His Pro Gln Thr Thr His Pro His Gln Ser Pro Ser Leu Ala Lys
545                 550                 555                 560

Gln Gln Thr Phe Pro Gln Tyr Glu Thr Ser Ser Ala Thr Thr Ser Pro
                565                 570                 575

Phe Phe Lys Pro Pro Ala Gln His Leu Asn Gly Ser Ala Ala Phe Asn
            580                 585                 590

Gly Val Asp Asn Gly Gly Leu Ala Ser Gly Asn Arg His Ala Glu Val
        595                 600                 605

Pro Pro Gly Thr Cys Pro Val Asp Pro Phe Glu Ala Gln Trp Ala Ala
    610                 615                 620

Leu Glu Ser Lys Ser Lys Gln Arg Thr Asn Pro Ser Pro Thr Asn Pro
625                 630                 635                 640

Phe Ser Ser Asp Leu Gln Lys Thr Phe Glu Ile Glu Leu
                645                 650


<210> SEQ ID NO 23
<211> LENGTH: 1815
<212> TYPE: DNA
<213> ORGANISM: Mus musculus

<400> SEQUENCE: 23

atgaacaaac tacggcaaag cttcaggaga aagaaagacg tttatgtccc agaggccagc      60

cgtccacatc agtggcagac agatgaagaa ggagtccgca ctggaaagtg tagcttccca     120

gttaagtacc tcggccacgt agaagttgat gagtcaagag gaatgcacat ctgtgaagat     180

gccgtaaaga gattgaaagc tgaaaggaag ttcttcaaag gcttctttgg aaaaacggga     240

aagaaagcag tgaaggccgt tctgtgggtg tcagcggatg ggctcagagt tgtggacgag     300

aaaactaagg acctcatagt tgaccagaca atagaaaaag tttccttctg tgccccagat     360
```

```
aggaactttg acagagcctt ttcttacata tgtcgtgatg gcaccactcg gcgatggatc    420

tgtcattgtt tcatggctgt caaagacacg gggaaagac tgagccacgc cgtgggctgt    480

gcttttgcag cctgtttaga gcgtaaacag aagcgggaga aggagtgtgg cgtcactgct    540

acttttgatg ccagtagaac cactttcaca agagaaggat cattccgtgt cacaactgcc    600

actgagcaag ccgaaagaga ggagatcatg aaacagttgc aagatgccaa gaaagctgag    660

acagacaaga cagttgttgg tccatcagtg gctcctggca acactgctcc atccccatcc    720

tctcccacct ctcccactcc ggatggcact gcatcttcag agatgaacaa tccccatgct    780

atcccacgcc ggcatgcacc aattgaacag cttgctcgtc aaggctcttt ccggggattt    840

cctgctctta gccagaagat gtcacccttt aaacgccagc tgtccctacg catcaatgag    900

ttgccttcca ctatgcagag gaagaccgat ttcccaataa aaaacacagt gcccgaggtg    960

gaaggagagg ccgagagcat cagctccttg tgttcccaga tcaccagtgc cttcagcacg   1020

ccctctgagg accccttctc ctccgcccca atgaccaaac cagtgacatt ggtggcacca   1080

cagtctcctg tgttacaagg gactgagtgg ggtcagtctt ctggtgctgc ctctccaggt   1140

ctcttccagg ctggtcacag acgcactccc tctgaagctg accgctggtt agaagaagtg   1200

tcaaagagtg tgcgggccca gcagcctcag gtctcagctg cccctctgca gccagttctc   1260

cagccgcctc cgcccgccgc cattgcccct ccagcacctc ctttccaagg acatgccttc   1320

ctcacgtccc agcctgtgcc cgtgggtgtg gtcccacccc tacaaccagc ctttgtccct   1380

acccagtcct accctgtggc caacgggatg ccctacccag cctctaatgt gcctgtagtg   1440

ggcatcaccc catcccagat ggtagccaat gtgtttggca ctgcaggcca ccctcagaca   1500

actcatccac atcagtcgcc aagcctggcc aagcagcaga cattccctca atatgagaca   1560

agtagtgcta ccaccagtcc cttctttaag cctcctgctc agcacctcaa tggttctgca   1620

gctttcaatg gtgtagacaa tggtgggcta gcctcaggaa acaggcatgc agaagtccct   1680

ccaggcacct gcccagtgga tcctttcgaa gctcagtggg ccgcactaga aagcaagtcc   1740

aagcagcgta caaatccttc tcctaccaac cctttctcca gtgacttaca gaaaacattt   1800

gaaatagaac tttag                                                    1815
```

```
<210> SEQ ID NO 24
<211> LENGTH: 604
<212> TYPE: PRT
<213> ORGANISM: Mus musculus

<400> SEQUENCE: 24

Met Asn Lys Leu Arg Gln Ser Phe Arg Arg Lys Lys Asp Val Tyr Val
1               5                   10                  15

Pro Glu Ala Ser Arg Pro His Gln Trp Gln Thr Asp Glu Glu Gly Val
            20                  25                  30

Arg Thr Gly Lys Cys Ser Phe Pro Val Lys Tyr Leu Gly His Val Glu
        35                  40                  45

Val Asp Glu Ser Arg Gly Met His Ile Cys Glu Asp Ala Val Lys Arg
    50                  55                  60

Leu Lys Ala Glu Arg Lys Phe Phe Lys Gly Phe Phe Gly Lys Thr Gly
65                  70                  75                  80

Lys Lys Ala Val Lys Ala Val Leu Trp Val Ser Ala Asp Gly Leu Arg
                85                  90                  95

Val Val Asp Glu Lys Thr Lys Asp Leu Ile Val Asp Gln Thr Ile Glu
            100                 105                 110
```

```
Lys Val Ser Phe Cys Ala Pro Asp Arg Asn Phe Asp Arg Ala Phe Ser
        115                 120                 125

Tyr Ile Cys Arg Asp Gly Thr Thr Arg Arg Trp Ile Cys His Cys Phe
    130                 135                 140

Met Ala Val Lys Asp Thr Gly Glu Arg Leu Ser His Ala Val Gly Cys
145                 150                 155                 160

Ala Phe Ala Ala Cys Leu Glu Arg Lys Gln Lys Arg Glu Lys Glu Cys
                165                 170                 175

Gly Val Thr Ala Thr Phe Asp Ala Ser Arg Thr Thr Phe Thr Arg Glu
            180                 185                 190

Gly Ser Phe Arg Val Thr Thr Ala Thr Glu Gln Ala Glu Arg Glu Glu
        195                 200                 205

Ile Met Lys Gln Leu Gln Asp Ala Lys Lys Ala Glu Thr Asp Lys Thr
    210                 215                 220

Val Val Gly Pro Ser Val Ala Pro Gly Asn Thr Ala Pro Ser Pro Ser
225                 230                 235                 240

Ser Pro Thr Ser Pro Thr Pro Asp Gly Thr Ala Ser Ser Glu Met Asn
                245                 250                 255

Asn Pro His Ala Ile Pro Arg Arg His Ala Pro Ile Glu Gln Leu Ala
            260                 265                 270

Arg Gln Gly Ser Phe Arg Gly Phe Pro Ala Leu Ser Gln Lys Met Ser
        275                 280                 285

Pro Phe Lys Arg Gln Leu Ser Leu Arg Ile Asn Glu Leu Pro Ser Thr
    290                 295                 300

Met Gln Arg Lys Thr Asp Phe Pro Ile Lys Asn Thr Val Pro Glu Val
305                 310                 315                 320

Glu Gly Glu Ala Glu Ser Ile Ser Ser Leu Cys Ser Gln Ile Thr Ser
                325                 330                 335

Ala Phe Ser Thr Pro Ser Glu Asp Pro Phe Ser Ser Ala Pro Met Thr
            340                 345                 350

Lys Pro Val Thr Leu Val Ala Pro Gln Ser Pro Val Leu Gln Gly Thr
        355                 360                 365

Glu Trp Gly Gln Ser Ser Gly Ala Ala Ser Pro Gly Leu Phe Gln Ala
    370                 375                 380

Gly His Arg Arg Thr Pro Ser Glu Ala Asp Arg Trp Leu Glu Glu Val
385                 390                 395                 400

Ser Lys Ser Val Arg Ala Gln Gln Pro Gln Val Ser Ala Ala Pro Leu
                405                 410                 415

Gln Pro Val Leu Gln Pro Pro Pro Pro Ala Ala Ile Ala Pro Pro Ala
            420                 425                 430

Pro Pro Phe Gln Gly His Ala Phe Leu Thr Ser Gln Pro Val Pro Val
        435                 440                 445

Gly Val Val Pro Pro Leu Gln Pro Ala Phe Val Pro Thr Gln Ser Tyr
    450                 455                 460

Pro Val Ala Asn Gly Met Pro Tyr Pro Ala Ser Asn Val Pro Val Val
465                 470                 475                 480

Gly Ile Thr Pro Ser Gln Met Val Ala Asn Val Phe Gly Thr Ala Gly
                485                 490                 495

His Pro Gln Thr Thr His Pro His Gln Ser Pro Ser Leu Ala Lys Gln
            500                 505                 510

Gln Thr Phe Pro Gln Tyr Glu Thr Ser Ser Ala Thr Thr Ser Pro Phe
        515                 520                 525
```

```
Phe Lys Pro Pro Ala Gln His Leu Asn Gly Ser Ala Ala Phe Asn Gly
    530                 535                 540

Val Asp Asn Gly Gly Leu Ala Ser Gly Asn Arg His Ala Glu Val Pro
545                 550                 555                 560

Pro Gly Thr Cys Pro Val Asp Pro Phe Glu Ala Gln Trp Ala Ala Leu
                565                 570                 575

Glu Ser Lys Ser Lys Gln Arg Thr Asn Pro Ser Pro Thr Asn Pro Phe
            580                 585                 590

Ser Ser Asp Leu Gln Lys Thr Phe Glu Ile Glu Leu
        595                 600


<210> SEQ ID NO 25
<211> LENGTH: 1089
<212> TYPE: DNA
<213> ORGANISM: Homo sapiens

<400> SEQUENCE: 25

atggagactg acgcgcccca gcccggcctc gcctccccgg actcgccgca cgacccctgc      60

aagatgttca tcgggggact cagttggcag actacgcagg aagggctgcg cgaatacttc     120

ggccagttcg gggaggtgaa ggagtgtctg gtgatgcggg accccctgac caagagatcc     180

aggggtttcg gcttcgtcac tttcatggac caggcggggg tggataaagt gctggcgcaa     240

tcgcggcacg agctcgactc caaaacaatt gaccctaagg tggccttccc tcggcgagca     300

cagcccaaga tggtgactcg aacgaagaag atctttgtgg gggggctgtc ggtgaacacc     360

acggtggagg acgtgaagca atattttgag cagtttggga aggtggacga cgccatgctg     420

atgtttgaca aaaccaccaa ccggcaccga gggttcgggt ttgtcacgtt tgagagtgag     480

gacatcgtgg agaaagtgtg tgaaattcat tttcatgaaa tcaacaacaa aatggtggaa     540

tgtaagaaag ctcagccaaa ggaggtgatg tcgccaacgg gctcagcccg ggggaggtct     600

cgagtcatgc cctacggaat ggacgccttc atgctgggca tcggcatgct gggttaccca     660

ggtttccaag ccacaaccta cgccagccgg agttatacag gcctcgcccc tggctacacc     720

taccagttcc ccgaattccg tgtagagcgg accccctctcc cgagcgcccc agtcctcccc     780

gagcttacag ccattcctct cactgcctac ggaccaatgg cggcggcagc ggcggcagcg     840

gctgtggttc gagggacagg ctctcacccc tggacgatgg ctccccctcc aggttcgact     900

cccagccgca caggggggctt cctggggacc accagccccg gccccatggc cgagctctac     960

ggggcggcca accaggactc gggggtcagc agttacatca gcgccgccag ccctgccccc    1020

agcaccggct tcggccacag tcttgggggc cctttgattg ccacagcctt caccaatggg    1080

taccactga                                                            1089


<210> SEQ ID NO 26
<211> LENGTH: 362
<212> TYPE: PRT
<213> ORGANISM: Homo sapiens

<400> SEQUENCE: 26

Met Glu Thr Asp Ala Pro Gln Pro Gly Leu Ala Ser Pro Asp Ser Pro
1               5                   10                  15

His Asp Pro Cys Lys Met Phe Ile Gly Gly Leu Ser Trp Gln Thr Thr
            20                  25                  30

Gln Glu Gly Leu Arg Glu Tyr Phe Gly Gln Phe Gly Glu Val Lys Glu
        35                  40                  45

Cys Leu Val Met Arg Asp Pro Leu Thr Lys Arg Ser Arg Gly Phe Gly
```

```
    50                  55                  60

Phe Val Thr Phe Met Asp Gln Ala Gly Val Asp Lys Val Leu Ala Gln
65                  70                  75                  80

Ser Arg His Glu Leu Asp Ser Lys Thr Ile Asp Pro Lys Val Ala Phe
                85                  90                  95

Pro Arg Arg Ala Gln Pro Lys Met Val Thr Arg Thr Lys Lys Ile Phe
            100                 105                 110

Val Gly Gly Leu Ser Val Asn Thr Thr Val Glu Asp Val Lys Gln Tyr
        115                 120                 125

Phe Glu Gln Phe Gly Lys Val Asp Asp Ala Met Leu Met Phe Asp Lys
    130                 135                 140

Thr Thr Asn Arg His Arg Gly Phe Gly Phe Val Thr Phe Glu Ser Glu
145                 150                 155                 160

Asp Ile Val Glu Lys Val Cys Glu Ile His Phe His Glu Ile Asn Asn
                165                 170                 175

Lys Met Val Glu Cys Lys Lys Ala Gln Pro Lys Glu Val Met Ser Pro
            180                 185                 190

Thr Gly Ser Ala Arg Gly Arg Ser Arg Val Met Pro Tyr Gly Met Asp
        195                 200                 205

Ala Phe Met Leu Gly Ile Gly Met Leu Gly Tyr Pro Gly Phe Gln Ala
    210                 215                 220

Thr Thr Tyr Ala Ser Arg Ser Tyr Thr Gly Leu Ala Pro Gly Tyr Thr
225                 230                 235                 240

Tyr Gln Phe Pro Glu Phe Arg Val Glu Arg Thr Pro Leu Pro Ser Ala
                245                 250                 255

Pro Val Leu Pro Glu Leu Thr Ala Ile Pro Leu Thr Ala Tyr Gly Pro
            260                 265                 270

Met Ala Ala Ala Ala Ala Ala Ala Ala Val Val Arg Gly Thr Gly Ser
        275                 280                 285

His Pro Trp Thr Met Ala Pro Pro Pro Gly Ser Thr Pro Ser Arg Thr
    290                 295                 300

Gly Gly Phe Leu Gly Thr Thr Ser Pro Gly Pro Met Ala Glu Leu Tyr
305                 310                 315                 320

Gly Ala Ala Asn Gln Asp Ser Gly Val Ser Ser Tyr Ile Ser Ala Ala
                325                 330                 335

Ser Pro Ala Pro Ser Thr Gly Phe Gly His Ser Leu Gly Gly Pro Leu
            340                 345                 350

Ile Ala Thr Ala Phe Thr Asn Gly Tyr His
        355                 360


<210> SEQ ID NO 27
<211> LENGTH: 987
<212> TYPE: DNA
<213> ORGANISM: Homo sapiens

<400> SEQUENCE: 27

atggaggcaa atgggagcca aggcacctcg ggcagcgcca acgactccca gcacgacccc     60

ggtaaaatgt ttatcggtgg actgagctgg cagacctcac cagatagcct tagagactat    120

tttagcaaat ttggagaaat tagagaatgt atggtcatga gagatcccac tacgaaacgc    180

tccagaggct tcggtttcgt cacgttcgca gacccagcaa gtgtagataa agtattaggt    240

cagccccacc atgagttaga ttccaagacg attgacccca aagttgcatt tcctcgtcga    300

gcgcaaccca agatggtcac aagaacaaag aaaatatttg taggcgggtt atctgcgaac    360
```

```
acagtagtgg aagatgtaaa gcaatatttc gagcagtttg gcaaggtgga agatgcaatg    420

ctgatgtttg ataaaactac caacaggcac agagggtttg gctttgtcac ttttgagaat    480

gaagatgttg tggagaaagt ctgtgagatt catttccatg aaatcaataa taaaatggta    540

gaatgtaaga aagctcagcc gaaagaagtc atgttcccac ctgggacaag aggccgggcc    600

cggggactgc cttacaccat ggacgcgttc atgcttggca tggggatgct gggatatccc    660

aacttcgtgg cgacctatgg ccgtggctac cccggatttg ctccaagcta tggctatcag    720

ttcccaggct tcccagcagc ggcttatgga ccagtggcag cagcggcggt ggcggcagca    780

agaggatcag gctccaaccc ggcgcggccc ggaggcttcc cgggggccaa cagcccagga    840

cctgtcgccg atctctacgg ccctgccagc caggactccg gagtggggaa ttacataagt    900

gcggccagcc cacagccggg ctcgggcttc ggccacggca tagctggacc tttgattgca    960

acggccttta caaatggata ccattga                                        987
```

```
<210> SEQ ID NO 28
<211> LENGTH: 328
<212> TYPE: PRT
<213> ORGANISM: Homo sapiens

<400> SEQUENCE: 28

Met Glu Ala Asn Gly Ser Gln Gly Thr Ser Gly Ser Ala Asn Asp Ser
1               5                   10                  15

Gln His Asp Pro Gly Lys Met Phe Ile Gly Gly Leu Ser Trp Gln Thr
            20                  25                  30

Ser Pro Asp Ser Leu Arg Asp Tyr Phe Ser Lys Phe Gly Glu Ile Arg
        35                  40                  45

Glu Cys Met Val Met Arg Asp Pro Thr Thr Lys Arg Ser Arg Gly Phe
    50                  55                  60

Gly Phe Val Thr Phe Ala Asp Pro Ala Ser Val Asp Lys Val Leu Gly
65                  70                  75                  80

Gln Pro His His Glu Leu Asp Ser Lys Thr Ile Asp Pro Lys Val Ala
                85                  90                  95

Phe Pro Arg Arg Ala Gln Pro Lys Met Val Thr Arg Thr Lys Lys Ile
            100                 105                 110

Phe Val Gly Gly Leu Ser Ala Asn Thr Val Val Glu Asp Val Lys Gln
        115                 120                 125

Tyr Phe Glu Gln Phe Gly Lys Val Glu Asp Ala Met Leu Met Phe Asp
    130                 135                 140

Lys Thr Thr Asn Arg His Arg Gly Phe Gly Phe Val Thr Phe Glu Asn
145                 150                 155                 160

Glu Asp Val Val Glu Lys Val Cys Glu Ile His Phe His Glu Ile Asn
                165                 170                 175

Asn Lys Met Val Glu Cys Lys Lys Ala Gln Pro Lys Glu Val Met Phe
            180                 185                 190

Pro Pro Gly Thr Arg Gly Arg Ala Arg Gly Leu Pro Tyr Thr Met Asp
        195                 200                 205

Ala Phe Met Leu Gly Met Gly Met Leu Gly Tyr Pro Asn Phe Val Ala
    210                 215                 220

Thr Tyr Gly Arg Gly Tyr Pro Gly Phe Ala Pro Ser Tyr Gly Tyr Gln
225                 230                 235                 240

Phe Pro Gly Phe Pro Ala Ala Ala Tyr Gly Pro Val Ala Ala Ala Ala
                245                 250                 255

Val Ala Ala Ala Arg Gly Ser Gly Ser Asn Pro Ala Arg Pro Gly Gly
```

```
            260                 265                 270

Phe Pro Gly Ala Asn Ser Pro Gly Pro Val Ala Asp Leu Tyr Gly Pro
        275                 280                 285

Ala Ser Gln Asp Ser Gly Val Gly Asn Tyr Ile Ser Ala Ala Ser Pro
    290                 295                 300

Gln Pro Gly Ser Gly Phe Gly His Gly Ile Ala Gly Pro Leu Ile Ala
305                 310                 315                 320

Thr Ala Phe Thr Asn Gly Tyr His
                325


<210> SEQ ID NO 29
<211> LENGTH: 756
<212> TYPE: DNA
<213> ORGANISM: Homo sapiens

<400> SEQUENCE: 29

atggccgatc tgacatcggt gctcacttct gttatgtttt ctccctctag taaaatgttt      60

atcggtggac tgagctggca gacctcacca gatagcctta gagactattt tagcaaattt     120

ggagaaatta gagaatgtat ggtcatgaga gatcccacta cgaaacgctc cagaggcttc     180

ggtttcgtca cgttcgcaga cccagcaagt gtagataaag tattaggtca gccccaccat     240

gagttagatt ccaagacgat tgaccccaaa gttgcatttc ctcgtcgagc gcaacccaag     300

atggtcacaa gaacaaagaa aatatttgta ggcgggttat ctgcgaacac agtagtggaa     360

gatgtaaagc aatatttcga gcagtttggc aaggtggaag atgcaatgct gatgtttgat     420

aaaactacca acaggcacag agggtttggc tttgtcactt ttgagaatga agatgttgtg     480

gagaaagtct gtgagattca tttccatgaa atcaataata aaatggtaga atgtaagaaa     540

gctcagccga aagaagtcat gttcccacct gggacaagag gccgggcccg gggactgcct     600

tacaccatgg acgcgttcat gcttggcatg ggatgctgg gatatcccaa cttcgtggcg      660

acctatggcc gtggctaccc cggatttgct ccaagctatg gctatcagtt cccagactat     720

ttgccggttt cacaagacat aatttttatc aactag                                756


<210> SEQ ID NO 30
<211> LENGTH: 251
<212> TYPE: PRT
<213> ORGANISM: Homo sapiens

<400> SEQUENCE: 30

Met Ala Asp Leu Thr Ser Val Leu Thr Ser Val Met Phe Ser Pro Ser
1               5                   10                  15

Ser Lys Met Phe Ile Gly Gly Leu Ser Trp Gln Thr Ser Pro Asp Ser
            20                  25                  30

Leu Arg Asp Tyr Phe Ser Lys Phe Gly Glu Ile Arg Glu Cys Met Val
        35                  40                  45

Met Arg Asp Pro Thr Thr Lys Arg Ser Arg Gly Phe Gly Phe Val Thr
    50                  55                  60

Phe Ala Asp Pro Ala Ser Val Asp Lys Val Leu Gly Gln Pro His His
65                  70                  75                  80

Glu Leu Asp Ser Lys Thr Ile Asp Pro Lys Val Ala Phe Pro Arg Arg
                85                  90                  95

Ala Gln Pro Lys Met Val Thr Arg Thr Lys Lys Ile Phe Val Gly Gly
            100                 105                 110

Leu Ser Ala Asn Thr Val Val Glu Asp Val Lys Gln Tyr Phe Glu Gln
        115                 120                 125
```

-continued

```
Phe Gly Lys Val Glu Asp Ala Met Leu Met Phe Asp Lys Thr Thr Asn
    130                 135                 140

Arg His Arg Gly Phe Gly Phe Val Thr Phe Glu Asn Glu Asp Val Val
145                 150                 155                 160

Glu Lys Val Cys Glu Ile His Phe His Glu Ile Asn Asn Lys Met Val
                165                 170                 175

Glu Cys Lys Lys Ala Gln Pro Lys Glu Val Met Phe Pro Pro Gly Thr
            180                 185                 190

Arg Gly Arg Ala Arg Gly Leu Pro Tyr Thr Met Asp Ala Phe Met Leu
        195                 200                 205

Gly Met Gly Met Leu Gly Tyr Pro Asn Phe Val Ala Thr Tyr Gly Arg
    210                 215                 220

Gly Tyr Pro Gly Phe Ala Pro Ser Tyr Gly Tyr Gln Phe Pro Asp Tyr
225                 230                 235                 240

Leu Pro Val Ser Gln Asp Ile Ile Phe Ile Asn
                245                 250
```

DIAGNOSTIC AND TREATMENT FOR CHRONIC AND ACUTE PHASE MYELOID LEUKEMIA

This application is a national stage filing under 35 U.S.C. 371 of International Patent Application No. PCT/US2010/035039, filed May 14, 2010, which claims the benefit of U.S. Provisional Patent Application No. 61/178,370, filed May 14, 2009, and U.S. Provisional Patent Application No. 61/332,943, filed May 10, 2010. The contents of all of these applications are incorporated by reference herein in their entireties.

STATEMENT REGARDING FEDERALLY SPONSORED RESEARCH

This invention was made with government support under grant nos. CA18029, CA140371, CA122206, DK63031, DK072234, AI067798, HL097767, and DP1OD006430 awarded by the United States Institutes of Health. The government has certain rights in the invention.

SEQUENCE LISTING

The sequence listing is filed with the application in electronic format only and is incorporated by reference herein. The sequence listing text file "ASFILED-SequenceListingWO00.txt" was created on Jun. 16, 2010, and is 69,478 bytes in size.

BACKGROUND

The National Cancer Institute estimates that in the United States one in three people will be afflicted with cancer. Moreover, approximately 50% to 60% of people with cancer will eventually die from the disease. Early intervention and targeted therapeutic treatment are needed to increase cancer survival. The present invention relates to methods for cancer diagnosis and treatment.

In particular, myeloid leukemia may present as a slow-growing chronic phase with cells able to undergo differentiation (Chronic Myeloid Leukemia, CML) or as a more aggressive and fast-growing acute phase with cells that are unable to differentiate (Acute Myeloid Leukemia, AML). There is a need in the art for methods of distinguishing the various stages of myeloid leukemia and predicting responsiveness of leukemias to types of chemotherapeutics. In addition, there is a need for methods of screening cancer for chemotherapeutic sensitivity and for developing novel therapeutics.

SUMMARY

In one embodiment, methods of predicting responsiveness of a cancer cell to a tyrosine kinase inhibitor are provided. The methods include evaluating the level of Numb expression in the cancer cell and then using the level of expression to predict responsiveness to the inhibitor.

In another aspect, methods of predicting the risk of progression of a cancer cell to a more aggressive form are provided. These methods include evaluating the level of Numb expression in the cancer cell and using the level of expression to predict the risk of progression to a more aggressive form of the cancer.

In yet another aspect, methods of reducing proliferation or promoting differentiation of a cancer cell having reduced expression of Numb relative to a control are provided. These methods include contacting the cell with an agent capable of increasing the level of Numb in the cell. The increased level of Numb reduces proliferation and promotes differentiation of the cells.

In still another aspect, methods of treating a mammalian subject having a cancer that has a reduced level of Numb are provided. The methods include administering an agent capable of increasing the level of Numb to an amount effective to treat the cancer.

In a further aspect, methods of assessing an agent for chemotherapeutic potential are provided. The methods include contacting a cell with the agent and evaluating the level of Numb in the contacted cell. The level of Numb in the contacted cell is indicative of the chemotherapeutic potential of the agent.

In still a further aspect, methods of reducing proliferation or promoting differentiation of a cancer cell having increased expression of Msi are provided. The methods include contacting the cell with an agent capable of decreasing the level of Msi in the cell to reduce proliferation or increase differentiation.

In yet another aspect, methods of treating a mammalian subject having a cancer that has an increased level of Msi expression relative to a control are provided. The methods include administering an agent capable of decreasing the level of Msi to the subject in an amount effective to treat the cancer.

In a further aspect, methods of assessing an agent for chemotherapeutic potential are provided. The methods include contacting a cell with the agent and evaluating the level of Msi in the contacted cell. The level of Msi in the contacted cell is indicative of the chemotherapeutic potential of the agent.

In yet another aspect, methods of predicting the risk of progression of a cancer cell to a more aggressive form are provided. These methods include evaluating the level of Msi expression in the cancer cell and using the level of expression to predict the risk of progression to a more aggressive form of the cancer.

Other aspects of the invention will become apparent by consideration of the detailed description and accompanying drawings.

BRIEF DESCRIPTION OF THE DRAWINGS

FIG. 1B is a graph of the relative gene expression of Msi2 in AML sorted into Lin− or Lin+ fractions based on the expression of lineage markers.

DETAILED DESCRIPTION

Figure 1:
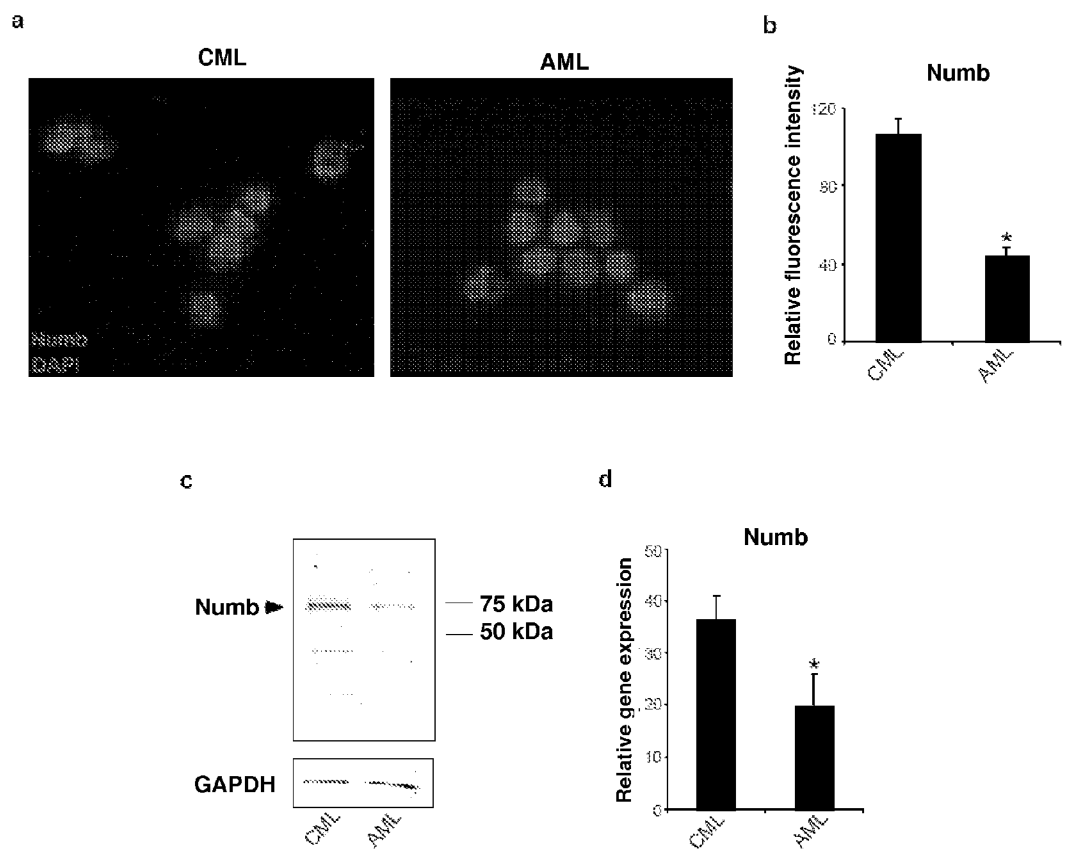
FIG. 1A are images of AML and CML cells stained with anti-Numb antibody (red) and DAPI (green).
FIG. 1B is a graph of fluorescence intensity of Numb staining for AML and CML cells.
FIG. 1C is an image of a Western Blot showing detection of Numb expression in CML and AML cells.
FIG. 1D is a graph of relative gene expression of Numb as analyzed by realtime PCR for AML and CML cells.

As described in the Examples, it was discovered that CML cells in general expressed significantly higher levels of Numb as compared to AML cells. As used herein, the aggressive from of CML is referred to either as blast crisis CML (bc-CML) or acute phase leukemia (AML). Interestingly, a subpopulation of CML cells expressing lower levels of Numb was identified. Surprisingly, the CML cells expressing lower levels of Numb correspond to CML cells unresponsive to treatment with imatinib, a tyrosine kinase inhibitor. Thus it was discovered that the level of Numb expression in a cancer cell can be used to predict responsiveness of CML cells to chemotherapeutics. Further, it is appreciated that therapeutics directed at increasing Numb expression within the cancer cells may decrease the aggressiveness of the cancer and increase responsiveness to other chemotherapeutics.

In addition, it was also discovered that Musashi, namely Msi2, expression downregulates Numb expression. Thus, Musashi expression may also be predictive of chemotherapeutic responsiveness. Additionally, it was discovered that reducing expression of Musashi in the cancer cells results in increased Numb expression, reduces the aggressiveness of the cancer and increases the responsiveness of the cancer to chemotherapeutics.

Methods of predicting responsiveness of a cancer cell to a tyrosine kinase inhibitor are provided herein. The method includes evaluating the level of Numb expression in the cancer cell and then using the level of Numb expression in the cancer cell to predict the responsiveness of the cancer cell to the tyrosine kinase inhibitor. As shown in Example 6, CML cells that do not respond to treatment with the tyrosine kinase inhibitor imatinib were found to have reduced expression of Numb. Accordingly, reduced Numb expression relative to a control is predictive of non-responsiveness to tyrosine kinase inhibitors, including imatinib.

The level of Numb expression in the cancer cell may be evaluated by a variety of techniques, as will be appreciated by those of skill in the art. For example, the level of Numb expression may be evaluated at either the protein or mRNA level using techniques including, but not limited to, Western blot, ELISA, Northern blot, real time PCR, immunofluorescence, or FACS analysis. In Example 2, the expression level of Numb was evaluated by immunofluorescence by visualizing cells stained with a fluorescently-labeled Numb-specific antibody, Western blot analysis of Numb protein expression, and RT-PCR of Numb transcripts.

As stated above, the expression level of Numb may be compared to a control. A control may include comparison to the level of Numb expression in a control cell, such as a noncancerous cell or a cancer cell with known responsiveness to a therapeutic. Alternatively a control may include an average range of the level of Numb expression from a population of chemotherapeutic responsive CML cells, non-cancer cells, chemotherapeutic non-responsive cells, or a combination thereof. Alternatively, a standard value developed by analyzing the results of a population of cells with known responsivities to tyrosine kinase inhibitors may be used. Those skilled in the art will appreciate that a variety of controls may be used.

Predicting may include using the information found in the Examples or generated by another entity to generate predictions. Predictions may be based on a comparison internal to a single assay or by comparison to a standard. For example the level of expression of Numb may be used to predict a cancer's responsiveness to a therapeutic. Predictions may be generated in relation to a standard or control as discussed above. This does not mean that the predicted event will occur with 100% certainty. Predicting and prediction also includes, but is not limited to, generating a statistically based indication of whether a particular event will occur, e.g. whether the cancer will be responsive to treatment with tyrosine kinase inhibitors.

The cancer cells for use in the methods include, but are not limited to, cancers cells characterized by a lack of differentiation of the cell. Examples of this type of cancer cell may include, but are not limited to, a leukemia cell, a breast cancer cell, a glioblastoma cell, or a lymphoma cell. The leukemia cell may be myeloproliferative disorder including but not limited to preleukemia. The leukemia cell may be a medullablastoma cell. The leukemia cell may be a myeloid or a lymphoid leukemia cell. Suitably, the cancer cell may be a myelogenous leukemia cell. Suitably, the cancer cell may be a CML or AML cell.

Tyrosine kinase inhibitors encompass agents that inhibit the activity of one or more tyrosine kinases. For example, a tyrosine kinase inhibitor may indirectly or directly bind and inhibit the activity of the tyrosine kinase, including binding activity or catalytic activity. A tyrosine kinase inhibitor may prevent expression of the tyrosine kinase, or inhibit the ability of the tyrosine kinase to mediate phosphorylation of its target. Examples of tyrosine kinase inhibitors include, but are not limited to, imatinib mesylate, axitinib, bosutinib, cediranib, dasatinib, erlotinib, gefitinib, lapatinib, lestaurtinib, nilotinib, semaxanib, sunitinib, vandetanib, and vatalanib.

Figure 7:
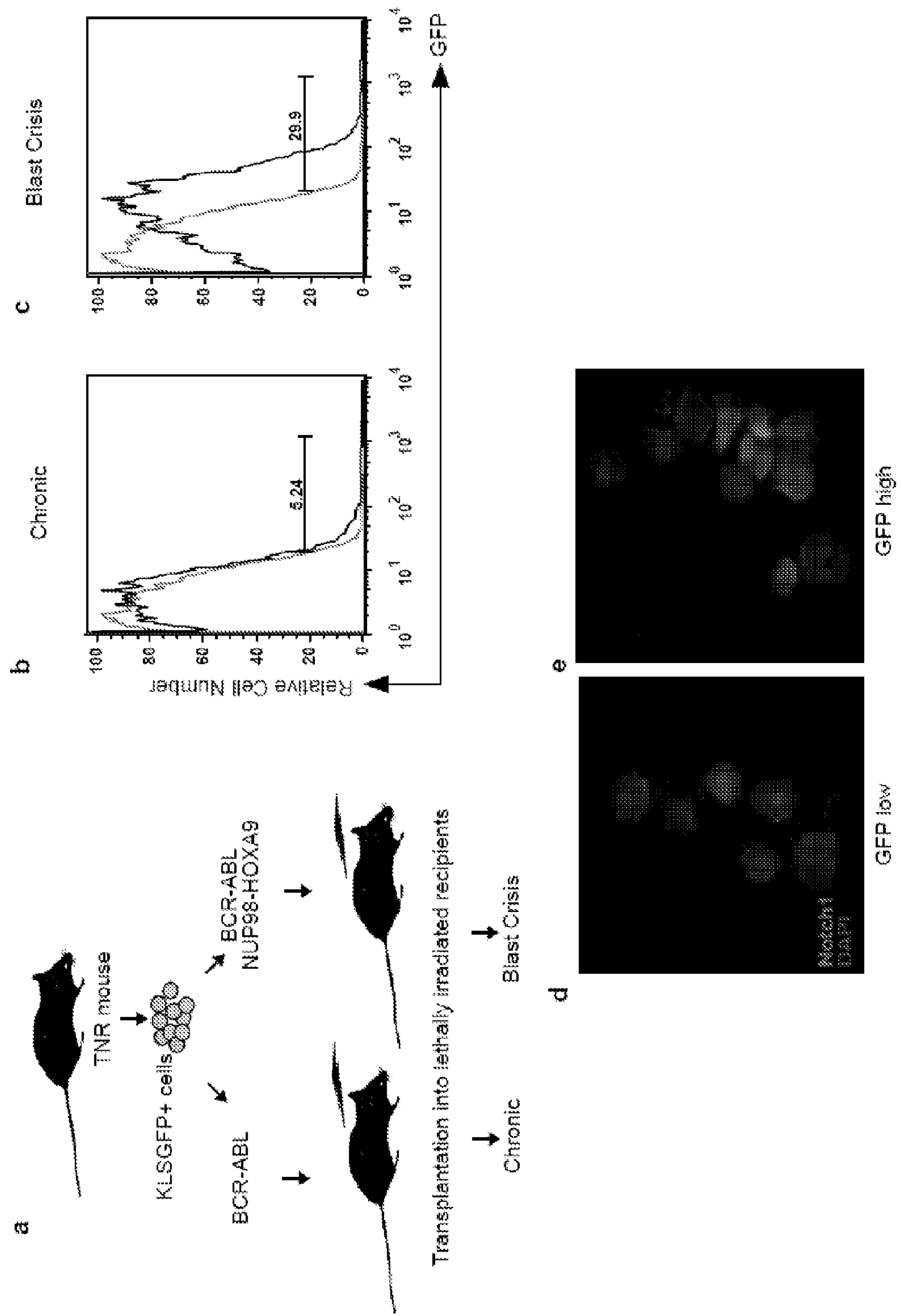
FIG. 7A is a schematic of the strategy to detect Notch signaling in chronic and blast crisis CML.
FIG. 7B shows GFP expression in donor derived cells from chronic CML as analyzed by FACS for TNR reporter activity.
FIG. 7C shows GFP expression in donor derived cells from blast crisis CML as analyzed by FACS for TNR reporter activity.
FIGS. 7D and 7E show blast crisis CML cells from TNR mice that were cytospun and immunostained with anti-cleaved Notch1 antibody and DAPI.

The level of Numb protein correlates to the resistance or sensitivity of a cancer cell to treatment with a tyrosine kinase inhibitor. For example, reduced expression of Numb relative to a control cell that is responsive to a tyrosine kinase inhibitor is indicative of non-responsiveness. Increased expression of Numb relative to an AML cell is indicative of responsiveness of the cell to tyrosine kinase inhibitors. In FIG. 7, non-responsive CML cells expressed Numb at a level 20% of that of responsive CML cells. Cells expressing less than about 50%, about 40%, about 30%, about 20%, about 10%, about 5%, or about 1% as much Numb as control cells responsive to treatment are predicted to be non-responsive to treatment with tyrosine kinase inhibitors. Conversely, cells expressing more than about 50%, 60%, 70%, 80%, 90%, or 100% as much Numb as control cells responsive to treatment are predicted to be responsive to treatment with tyrosine kinase inhibitors. It is envisioned that cells having more than 2, 3, 4, 5, 6, 8, or 10 fold higher Numb expression than control cells non-responsive to treatment may be responsive to treatment with tyrosine kinase inhibitors, and cells expressing less than 125%, 100%, or 90% as much Numb as control cells non-responsive to treatment are predicted to be non-responsive to treatment with tyrosine kinase inhibitors.

In another embodiment, methods of predicting the risk of progression of a cancer cell to a more aggressive form are provided. The methods include evaluating the level of Numb expression in a cancer cell and using the level of expression to predict the risk of progression to a more aggressive form. Suitably, a reduced level of Numb expression relative to a control CML cell is indicative of an increased risk of progression to a more aggressive form. Similarly, increased expression of Numb correlates with less aggressive cancers. As shown in Examples 2-6, CML cells expressed significantly higher levels of Numb compared to AML cells, and Numb expression appears to be reduced with progression from chronic disease to acute disease. For example, reduced expression of Numb relative to a control CML cell is indicative of an increased risk of progression of the cancer cell to a more aggressive form. Increased expression of Numb relative to a control CML cell is indicative of a decreased risk of progression of the cancer cell to a more aggressive form. Thus the risk of progression of the cancer may be evaluated using methods similar to those described above for predicting responsiveness to a therapeutic.

In another embodiment, methods of reducing proliferation or promoting differentiation of a cancer cell having reduced expression of Numb protein relative to a control are provided. The cancer cells are contacted with an agent capable of increasing the level of Numb protein in a cell. In this embodiment, a control includes a control cell, such as a non-cancer cell of the same type as the cancer cell or a standard based on such a control cell.

Agents capable of increasing the level of Numb protein include any agent capable of increasing Numb protein or Numb mRNA levels. In one embodiment, the agent may comprise the Numb protein itself. For example, the agent may include exogenously expressed and isolated Numb protein capable of being delivered to the cells. The Numb protein may be delivered to cells by a variety of methods, including fusion to Tat or VP16 or via a delivery vehicle, such as a liposome, all of which allow delivery of protein based agents across the cellular membrane. Those of skill in the art will appreciate that other delivery mechanisms for proteins may be used. Alternatively, Numb mRNA expression may be enhanced relative to control cells by contact with the agent. For example, the agent capable of increasing the level of natively expressed Numb protein may include a gene expression activator or de-repressor. The agent capable of increasing the level of Numb protein may also include agents that bind to Numb directly or indirectly and increase the effective level of Numb, for example, by enhancing the binding or other activity of Numb.

Figure 4:
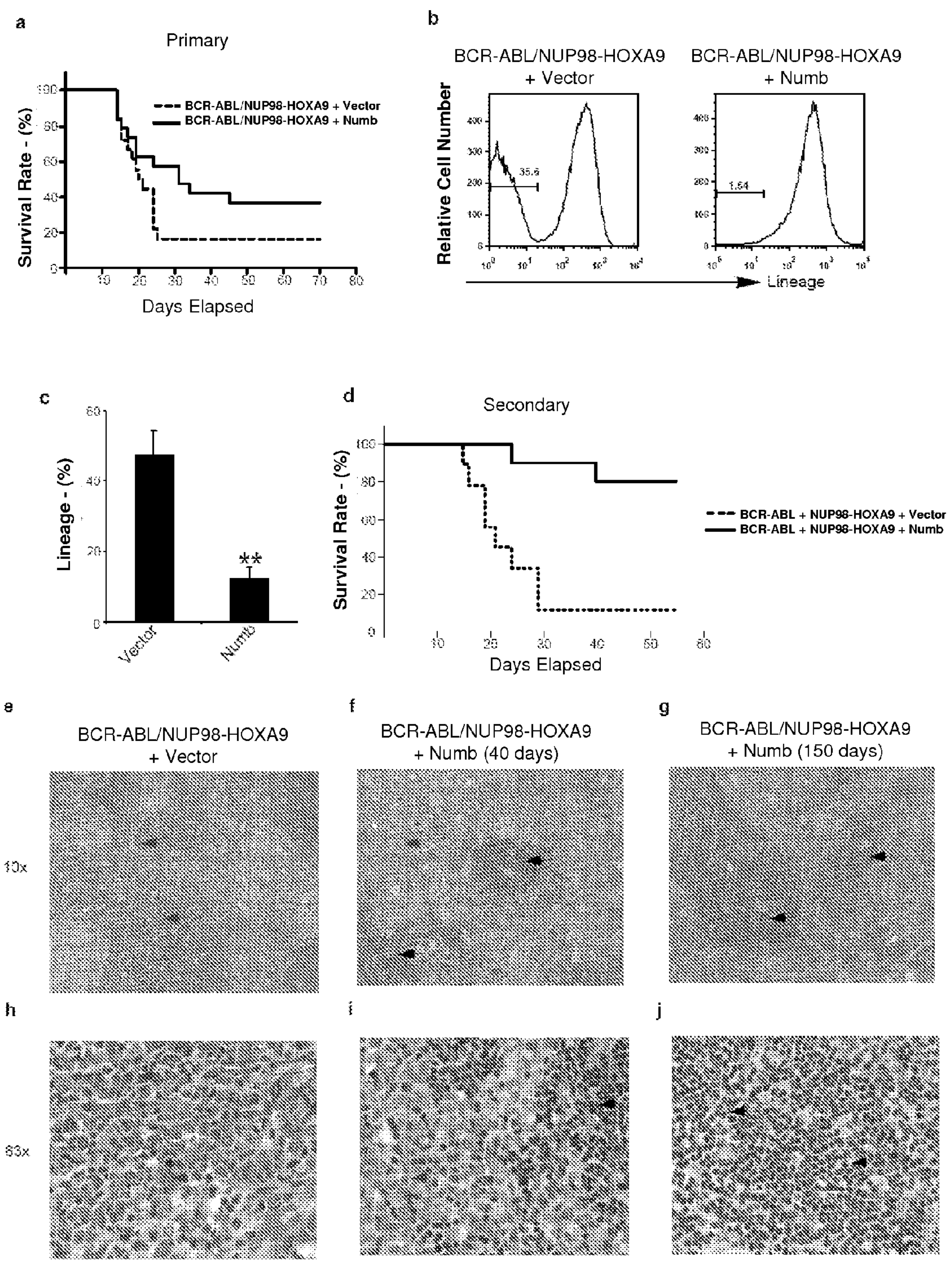
FIG. 4A is a graph of the survival rate of mice transplanted with bone marrow cells infected with BCR-ABL+NUP98-HOXA9 and either Vector or NUMB.
FIG. 4B is a graph of a FACS analysis showing the percentage of differentiated leukemic cells from mice transplanted with BCR-ABL/NUP98-HOXA9/Vector or BCR-ABL/NUP98-HOXA9/Numb infected cells.
FIG. 4C is a graph of FACS analysis showing the average percentage of lineage negative cells from control or Numb expressing leukemias.
FIG. 4D is a graph of the survival rate of mice transplanted with cells from primary transplanted mice.
FIG. 4E-J are images of spleen sections from leukemic Vector infected transplants (E, H), leukemic Numb infected transplants (F, I), and healthy Numb infected transplants (G, J).

In another embodiment, the agent capable of increasing the level of Numb protein may comprise a polynucleotide encoding the Numb protein or a polypeptide having at least 95% amino acid identity to Numb and having Numb activity. There are several isoforms of the Numb protein, including, for example, SEQ ID NOs: 12, 14, 16, 18, 20, 22, and 24, each of which may be encoded by more than one polynucleotide sequence, including, for example, SEQ ID NOs: 11, 13, 15, 17, 19, 21, and 23 (see polynucleotide and amino acid sequences appended to this application in a sequence listing, which is incorporated herein by reference in its entirety). Envisioned are polynucleotide sequences encoding Numb, a polypeptide sequence encoding Numb, or a polypeptide having at least 95% amino acid identity to Numb and having Numb activity. Those skilled in the art will appreciate that a Numb polynucleotide may be delivered to cells in a variety of ways, including, but not limited to, transfection, transduction, transformation, via a vector such as a viral vector or expression vector, or via a liposome. Suitably the polynucleotide encoding the Numb protein is operably connected to a promoter such that the Numb protein is expressed in the cancer cells. As shown in Example 4, expressing Numb from a vector in AML cells may increase the level of Numb and promote differentiation (FIG. 4B). It is further shown in the Examples that leukemias developed in the presence of Numb may be significantly more differentiated and less aggressive. Suitably, the agent has a direct effect on Numb protein or mRNA expression. In another embodiment, the agent capable of increasing the level of Numb protein may comprise an agent capable of decreasing Msi, as described further below.

In another embodiment, methods of treating a mammalian subject having a cancer with a reduced level of Numb protein as compared to a control are provided. The method may comprise administering to the subject an agent, such as those described above, capable of increasing the level of Numb protein in an amount effective to treat cancer. As will be appreciated by those of skill in the art, an agent may be administered by various methods including sublingually, orally, enterally, parenterally, topically, systemically or injected intravascularly or intraarterially, cutaneously, or peritoneally. Treating cancer includes, but is not limited to, reducing the number of cancer cells in the subject, reducing progression of a cancer cell from a chronic to a more aggressive form, reducing proliferation of cancer cells, killing of cancer cells, or reducing metastasis of cancer cells.

Figure 10:
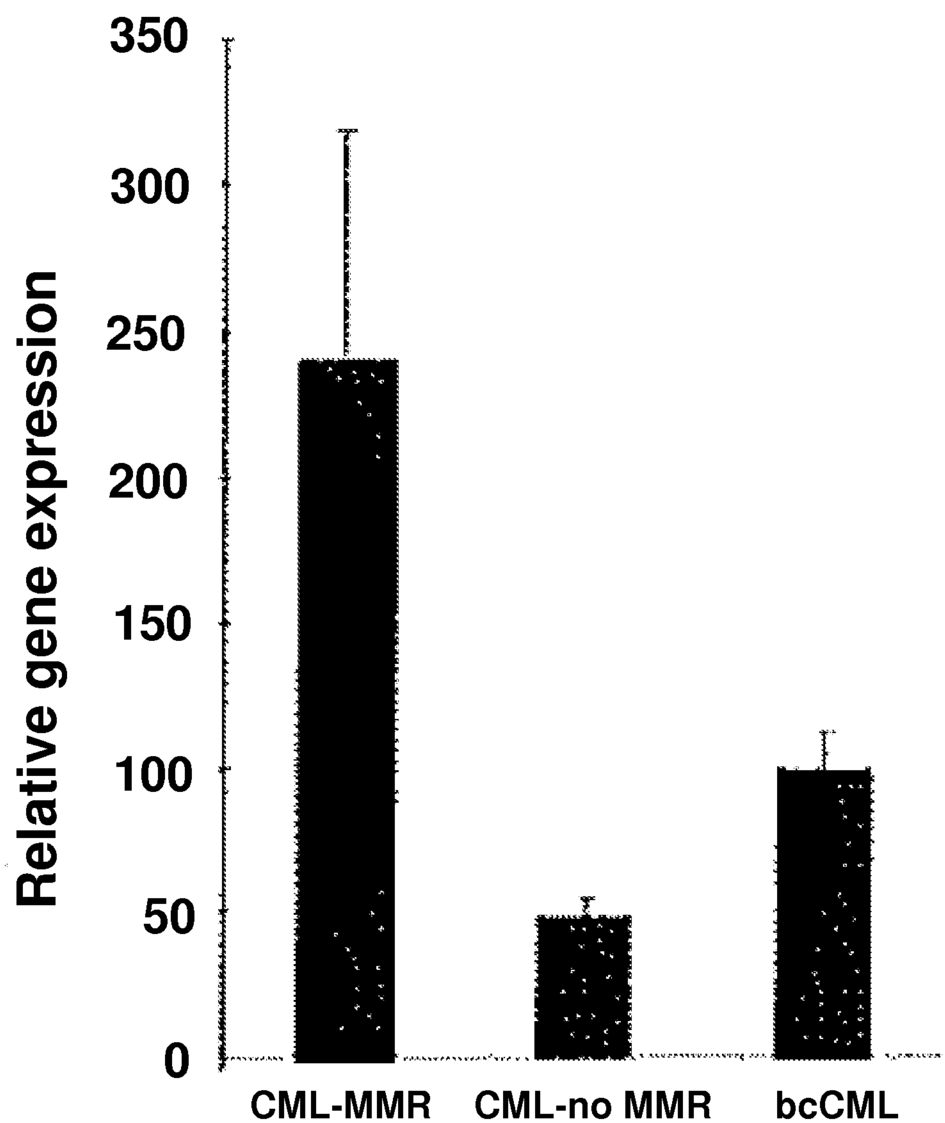
FIG. 10 is a graph of relative gene expression of Numb from human CML-MMR, CML-no MMR, and bcCML patients.

In another embodiment, methods of assessing the chemotherapeutic potential of an agent are provided. The methods may include contacting a cell with the agent and then evaluating the level of Numb in the contacted cell. As demonstrated in the Examples, the level of Numb in the contacted cell is indicative of the therapeutic potential of the agent. Specifically, increased expression of Numb in cells contacted with the agent is indicative of an agent with therapeutic potential. Conversely, a lack of any change or a reduction in Numb expression after contact with the agent as compared to the level of Numb expression prior to contact with the agent is indicative of a lack of therapeutic potential of the agent. In FIG. 10, CML cells responsive to imatinib were shown to express relatively high levels of Numb protein while those resistant to imatinib were shown to express relatively low levels of Numb.

Chemotherapeutic potential of an agent is the assessment of the agent's capability to act as a chemotherapeutic. Chemotherapeutic potential may include a prediction of the agent's capability to kill at least one cancer cell, to reduce the growth rate or proliferation rate of a cancer cell, to reduce the number of cancer cells in an individual, or to reduce progression of a cancer cells from a chronic to a more aggressive form.

Cells may be contacted with the agent directly or indirectly in vivo, in vitro, or ex vivo. Contacting encompasses administration to a cell, tissue, mammal, patient, or human. Further, contacting a cell includes adding an agent to a cell culture. Other suitable methods may include introducing or administering an agent to a cell, tissue, mammal, or patient using appropriate procedures and routes of administration as defined above.

In another embodiment, methods of reducing proliferation or promoting differentiation of a cancer cell having increased Msi expression are provided. The methods include contacting the cell with an agent capable of decreasing Msi to reduce proliferation or increase differentiation of cells. Decreasing Msi includes reducing the level of Msi expression at the mRNA or protein level or decreasing the activity of Msi. As used herein, Msi includes Msi1, Msi2, MSI1, MSI2, or combinations thereof. Also included are homologs and orthologs of Msi such as human MSI2. As shown in Example 8, the human ortholog MSI2 has the same pattern of expression in leukemic cells from chronic and blast-crisis CML as the expression pattern in a mouse model.

Levels of Msi correlate to aggressiveness of cancer. Thus, methods of predicting the risk of progression of a cancer cell to a more aggressive form are provided. These methods include evaluating the level of Msi expression in the cancer cell and using the level of expression to predict the risk of progression to a more aggressive form of the cancer.

Figure 16:
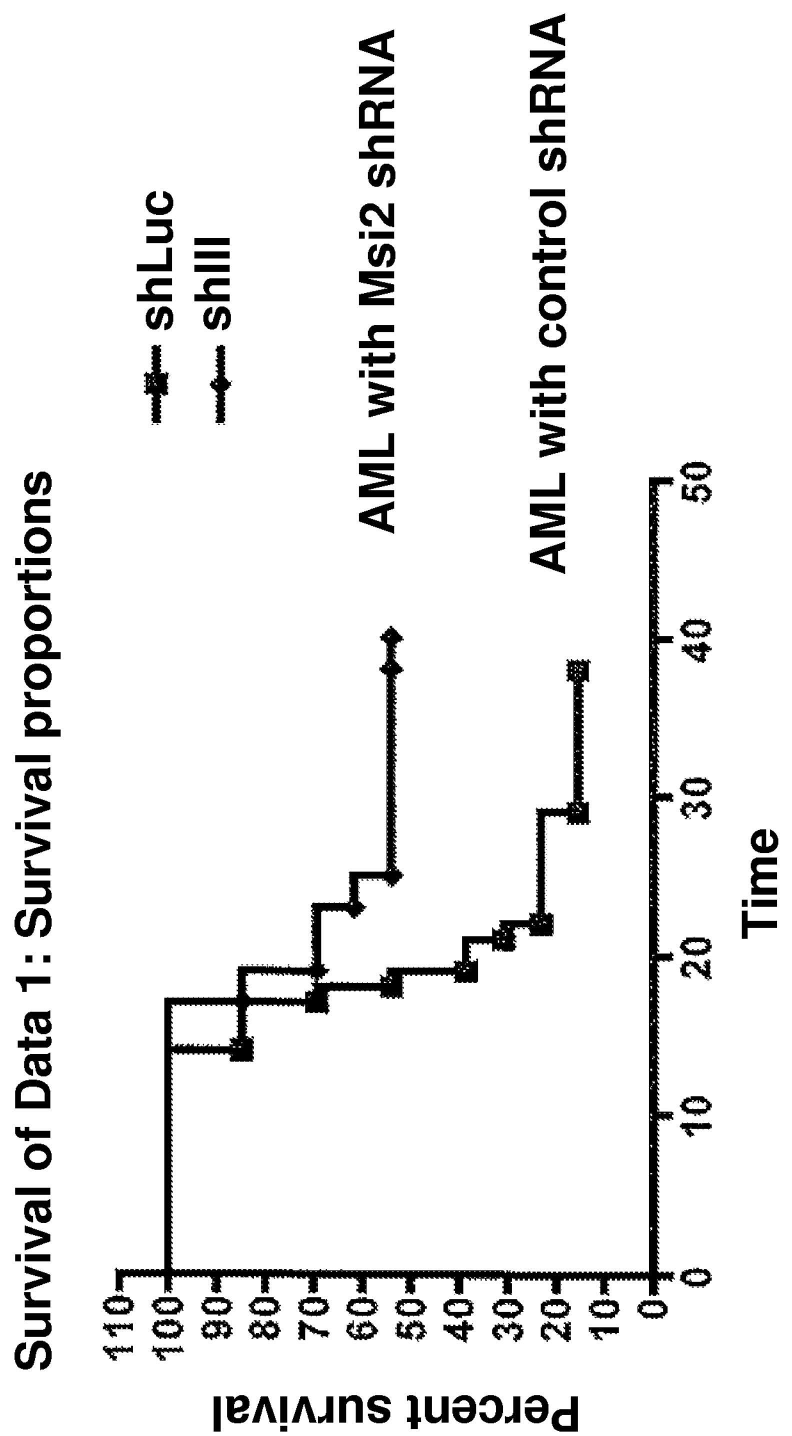
FIG. 16 is a graph of survival of mice transplanted with AML cells transduced with Msi2 shRNA or with a control shRNA.

As shown in Example 7, Msi2 contributes to the establishment and maintenance of AML from CML. Further shown in Example 7 is that AML cells require Msi2 during disease maintenance and propagation. FIG. 16 shows that decreasing the levels of Msi in a cell reduce cancer cell survival. Reducing the level of Msi in a cancer cell may reduce cancer cell survival by at least about 5%, at least about 10%, at least about 20%, at least about 30%, at least about 40%, at least about 50%, at least about 60%, or at least about 70%. A reduction in cancer cell survival may be achieved by reducing Msi expression or activity by at least about 50%, 40%, 30%, 20%, 10%, 5% or less as compared to the Msi expression or activity prior to treatment with the agent.

Figure 11:
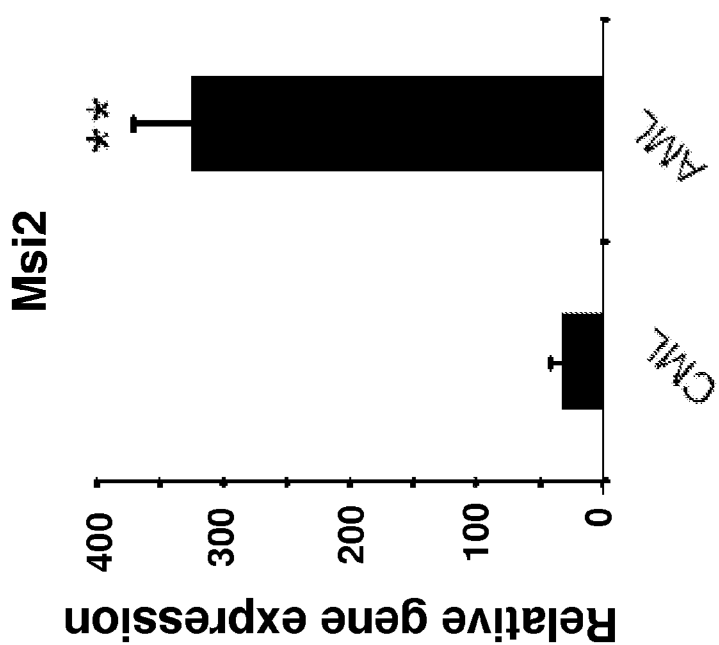
FIG. 11A is a graph of the relative gene expression of Msi2 in AML and CML cells.
Figure 11:
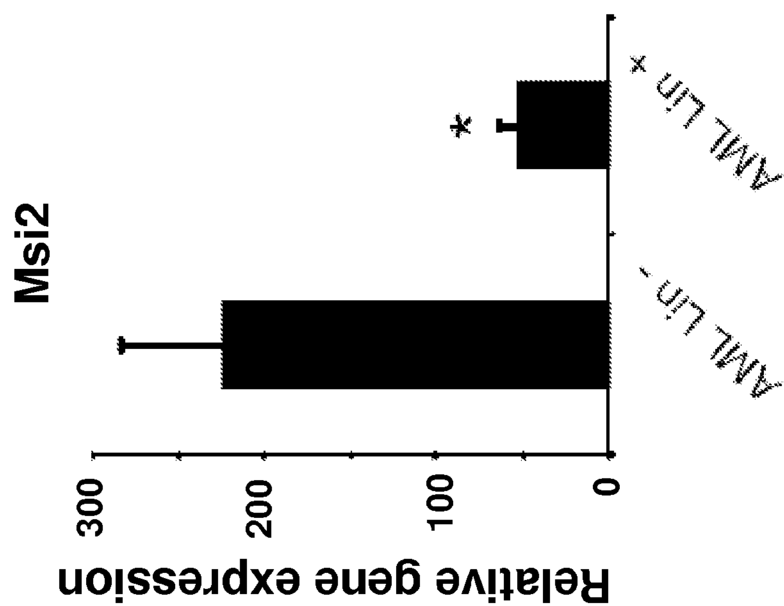

An agent capable of decreasing Msi includes a variety of agents and molecules capable of decreasing Msi mRNA transcripts or protein levels in the contacted cell. In one embodiment, the agent capable of decreasing Msi may comprise an inhibitory RNA. Suitably, the inhibitory RNA may comprise a shRNA such as SEQ ID NO: 9 as used in Example 7. An inhibitory RNA may comprise a sequence complementary to a portion of an RNA sequence encoding Msi. There are several isoforms of the Msi protein, including, for example, SEQ ID NOs: 26, 28, and 30, each of which may be encoded by more than one polynucleotide sequence, including, for example, SEQ ID NOs: 25, 27, and 29 (see polynucleotide and amino acid sequences appended to this application in a sequence listing, which is incorporated herein by reference in its entirety). Envisioned are polynucleotide sequences encoding Msi, a polypeptide sequence encoding Msi, or a polypeptide having at least 95% amino acid identity to Msi and having Msi activity. In some embodiments, the agent capable of decreasing Msi may include a gene expression repressor. In some embodiments, the agent capable of decreasing Msi may include a small molecule inhibitor. The agent capable of decreasing Msi may also include agents that bind to Msi directly or indirectly and decrease the effective level or activity of Msi, for example, by inhibiting the binding or other activity of Msi. The agent capable of decreasing Msi may also include agents that decrease Msi1, Msi2, or both. As shown in Examples 7 and 8, Msi2 expression was found to be greater in AML than in CML cells and Msi2 expression may be associated with immature leukemic cells (FIG. 11). Further, Msi2 knockdown with shRNA resulted in the longer latency of AML development in the mouse model of AML (FIG. 16).

In another embodiment, methods of treating a mammalian subject having a cancer with increased Msi expression relative to a control are provided. The methods include administering to the subject an effective amount of an agent capable of decreasing the level of Msi. Modes of administering an agent are discussed above. Agents suitable for the methods are similar to those described above that are capable of decreasing Msi expression or activity.

In another embodiment, methods of assessing an agent for chemotherapeutic potential are provided. The methods include contacting a cell with the agent and evaluating the level of Msi expression or activity in the contacted cell. The level of Msi expression or activity may be evaluated using methods similar to those described above. The level of Msi may be compared to a control, such as cells prior to contact with the agent, as described above. The level of Msi expression in the contacted cell may be indicative of the chemotherapeutic potential of the agent. As shown in Example 7, Msi2 may reduce the level of Numb protein and, at least in part, may activate a cascade that leads to inhibition of differentiation and a less aggressive form of cancer. Msi2 may downregulate Numb and contribute to the establishment and maintenance of acute myeloid leukemia. As detailed above, Numb expression may be used as part of a method to assess an agent for chemotherapeutic potential. Decreased Msi expression in a cancer cell may increase the level of Numb in the cancer cell and lead to reduced differentiation and a less aggressive form of cancer. As one example, reduced expression of Msi relative to an AML cancer cell control upon administration of an agent is indicative of an agent that is an effective chemotherapeutic agent.

EXAMPLES

Example 1

Materials and Methods

Mice

Mouse models of CML were generated by transducing bone marrow stem and progenitor cells with retroviruses carrying BCR-ABL (chronic phase), or BCR-ABL and NUP98-HOXA9 (blast crisis phase) and transplanted into irradiated recipient mice. The development of CML was confirmed by flow cytometry and histopathology. Transgenic Notch reporter (TNR), Rag1−/−, and C57BL6/J were used as transplant donors, and C57B16/J CD45.1 and CD1 mice were used as transplant recipients. All mice were 8-12 weeks of age. Mice were bred and maintained on acidified water after transplantation in the animal care facility at Duke University Medical Center. All live animal experiments were performed according to protocols approved by the Duke University Institutional Animal Care and Use Committee. For Msi2 knockdown experiments, lineage negative blast crisis CML cells were infected with Msi2 or control Luciferase shRNA retroviral constructs and leukemia incidence monitored.

Cell Isolation and FACS Analysis

HSCs (hematopoietic stem cells) were sorted from mouse bone marrow as described (Zhao, C. et al. *Cancer Cell* 2007, 12, 528-41, incorporated by reference herein in its entirety).

c-Kit+ cells were enriched by staining whole bone marrow with anti-c-Kit (CD117) microbeads (Miltenyi Biotec) and isolating positively labeled cells with autoMACS cell separation (Miltenyi Biotec). For lineage analysis peripheral blood cells were obtained by tail vein bleeds and diluted in 0.5 mL of 10 mM EDTA in PBS. 1 mL of 2% dextran was then added to each sample, and red blood cells depleted by sedimentation for 45 minutes at 37° C. Red blood cells were lysed using 1× RBC Lysis Buffer (eBiosciences) before staining for lineage markers. The following antibodies were used to define the lineage positive cells in leukemic samples: 145-2C11 (anti-CD3e), GK1.5 (anti-CD4), 53-6.7 (anti-CD8), RB6-8C5 Ly-6G (anti-Gr-1), M1/70 (anti-CD11b, Mac-1), Ter119 (anti-erythrocyte specific antigen), and 6B2 (anti-B220). Other antibodies used for HSC sorts included 53-7.3 (anti-CD5) as part of the lineage cocktail, 2B8 (anti-CD117, c-Kit) and D7 (anti-Ly-6A/E, Sca-1). All antibodies were purchased from Pharmingen or eBiosciences. Analysis and cell sorting were carried out on a FACSVantage SE (Becton Dickinson), FACSTAR (Becton Dickinson), or FACsDiva (Becton Dickinson) at the Duke Cancer Center FACS facility.

Viral Production and Infection

The BCR-ABL polynucleotide was a gift from Warren Pear and Ann Marie Pendergast and was cloned into a MSCV-IRES-YFP or a MSCV-IRES-CFP retroviral vector. HOXA9-NUP98-IRES-YFP was a gift from Gary Gilliland and Craig Jordan and was also cloned into the MSCV-IRES-NGFR vector. Numb cDNA (p65 isoform, Accession number BC033459, NCBI) was cloned into the MSCV-IRES-GFP (and hCD2) vectors. ICN1 was cloned into the MSCV-IRES-CFP or YFP retroviral expression vectors. Virus was produced by triple transfection of 293T cells with MSCV constructs along with gag-pol and VSVG constructs. Viral supernatant was collected for three days and concentrated 100-fold by ultracentrifugation at 50,000×g. For viral infection, c-Kit+ enriched or KLS cells were cultured overnight in the presence of X-Vivo15 (BioWhittaker), 50 μM 2-mercaptoethanol, 10% fetal bovine serum, SCF (100 ng/mL), and Tpo (20 ng/mL). After 12-18 h, concentrated retroviral supernatant was added to the cells. Cells were then incubated at 32° C. for 12 h and 37° C. for 36 h. Infected cells were then sorted based on their GFP, YFP, CFP, NGFR, or hCD2 expression as appropriate. All cytokines were purchased from R&D systems.

In Vitro Methylcellulose Assays

Lineage negative, NUP98-HOXA9-YFP positive cells from AML were sorted and infected retrovirally with either Vector-IRES-GFP or Numb-IRES-GFP. After 48 hours of infection, cells were sorted and serially plated on complete methylcellulose medium (Methocult GF M3434 from StemCell Technologies).

In Vivo Leukemia Models

Bone marrow c-Kit+ or KLS cells from C57BL6/J or TNR mice were enriched and cultured overnight in X-vivo 15 with 10% FBS, 50 μM 2-mercaptoethanol, 100 ng/mL SCF, and 20 ng/mL TPO in a 96 well U-bottom plate or 6 well plate. Subsequently, cells were infected with MSCV-BCR-ABL-IRES-YFP (or CFP) to generate CML, or MSCV-BCR-ABL-IRES-YFP (or CFP) and MSCV-NUP98-HOXA9-IRES-YFP (or NGFR) to generate AML. Cells were harvested 48 hours after infection and transplanted retro-orbitally into groups of 4-7 recipient mice. Recipients were lethally irradiated (10 Gy) for CML, and sublethally irradiated (7 Gy) for AML. For Numb overexpression, cells were infected with either MSCV-Numb-IRES-GFP (or hCD2) or MSCV-IRES-GFP (or hCD2) along with MSCV-BCR-ABL-IRES-YFP (or CFP) and MSCV-NUP98-HOXA9-IRES-NGFR (or YFP) and 20,000 to 100,000 sorted infected cells were transplanted per mouse. For secondary transplantation, cells from primary transplanted mice were sorted for either MSCV-Numb-IRES-GFP and MSCV-NUP98-HOXA9-YFP or MSCV-IRES-GFP and MSCV-NUP98-HOXA9-YFP, and 7,000 to 8,000 cells were transplanted per mouse. For ICN experiments, cells were infected with MSCV-ICN-IRES-CFP and MSCV-BCR-ABL-GFP, MSCV-ICN-IRES-CFP and MSCV-IRES-GFP, or MSCV-BCR-ABL-IRES-GFP and MSCV-IRES-CFP, and 10,000 to 20,000 KLS-derived or 200,000 to 500,000 c-kit+-derived sorted cells were transplanted per mouse. For the TNR mouse model, cells were infected with MSCV-BCR-ABL-IRES-YFP (or CFP) to generate CML or MSCV-BCR-ABL-IRES-YFP (or CFP) and MSCV-NUP98-HOXA9-IRES-NGFR to generate AML. 10,000 to 80,000 unsorted cells were transplanted per mouse. After transplantation, recipient mice were subsequently maintained on antibiotic water (sulfamethoxazole and trimethoprim) and evaluated daily for signs of morbidity, weight loss, failure to thrive, and splenomegaly. Premorbid animals were sacrificed by $CO_2$ asphyxiation followed by cervical dislocation. Subsequently relevant tissues were harvested and analyzed by flow cytometry and histopathology.

Immunofluorescence Staining

For immunofluorescence relevant cell populations were sorted, cytospun, and fixed in 4% paraformaldehyde for 5 minutes. Samples were then blocked using 20% normal donkey serum in PBS with 0.1% Tween 20, and stained at 4° C. overnight with an antibody to Numb (1:200) (ab4147, Abcam) followed by anti-goat Alexa 594 (Molecular probe) and DAPI. Slides were mounted using fluorescent mounting media (Fluoromount-G SouthernBiotech) and viewed by confocal microscopy.

Real Time PCR and RT PCR Analysis

RNA was isolated using RNAqueous-Micro (Ambion), levels were equalized, and RNA was converted to cDNA using Superscript II reverse transcriptase (Invitrogen). Quantitative real time PCRs were performed using an iCycler (BioRad) by mixing cDNAs, iQ SYBR Green Supermix (BioRad) and gene specific primers. Results were normalized to the level of beta-2-microglobulin (B2m). Primer sequences are as follows: Numb-F, ATGAGTTGCCTTCCACTATGCAG (SEQ ID NO: 1); Numb-R, TGCTGAAGGCACTGGTGATCTGG (SEQ ID NO: 2); Msi1-F, ATGGATGCCTTCATGCTGGGT (SEQ ID NO: 3); Msi1-R, CTCCGCTCTACACGGAATTCG (SEQ ID NO: 4); Msi2-F, TGCCATACACCATGGATGCGT (SEQ ID NO: 5); Msi2-R, GTAGCCTCTGCCATAGGTTGC (SEQ ID NO: 6); B2m-F, ACCGGCCTGTATGCTATCCAGAA (SEQ ID NO: 7); B2m-R, AATGTGAGGCGGGTGGAACTGT (SEQ ID NO: 8).

Statistical Analysis

Student's or Welch's t-test and logrank test were utilized to determine statistical significance.

Viral Constructs

Viral constructs used included MSCV-Numb-IRES-GFP, MSCV-Numb-IRES-hCD2, MSCV-NUP98-HOXA9-IRES-YFP, MSCV-NUP98-HOXA9-IRES-NGFR, MSCV-ICN1-IRES-CFP, MSCV-ICN1-IRES-YFP, MSCV-IRES-GFP, MSCV-BCR-ABL-IRES-YFP, MSCV-BCR-ABL-IRES-CFP, MSCV-BCR-ABL-IRES-GFP, MSCV-IRES-hCD2, MSCV-IRES-NGFR.

Chromatin Immunoprecipitation (ChIP) Assays

ChIP assays were performed using the myeloid leukemia cell line M1. DNA was crosslinked and immunoprecipitated with control or anti-HOXA9 antibodies and analyzed by PCR for regions of interest.

Human Samples

CML patient samples were obtained from the Korean Leukemia Bank (Korea), the Hammersmith MRD Lab Sample Archive (United Kingdom), the Fred Hutchinson Cancer Research Center (United States) and the Singapore General Hospital (Singapore). Gene expression in human chronic and blast crisis CML was analyzed by PCR or by DNA microarrays.

Example 2

Expression of Numb in CML and AML

The expression of Numb in mouse models of CML and AML was examined. CML was generated by introducing retroviral BCR-ABL into hematopoietic stem cell enriched populations (c-Kit+Lin−Sca-1+ or KLS), and transplanting these cells into irradiated recipients (Daley, G. Q., Van Etten, R. A. & Baltimore, D. *Science* 1990, 247, 824-30; Pear, W. S. et al. *Blood* 1998, 92, 3780-92; both incorporated herein by reference in their entireties). AML was induced by infecting KLS cells with both BCR-ABL and NUP98-HOXA9, and transplanting them into irradiated recipients (Dash, A. B. et al. *Proc Natl Acad Sci USA* 2002, 99, 7622-7; Neering, S. J. et al. *Blood* 2007, 110, 2578-85; both incorporated herein by reference in their entireties).

Cells from AML and CML were sorted, cytospun, and immunostained with anti-Numb antibody. Analysis of cells from fully developed AML and CML revealed that CML cells expressed significantly higher levels of Numb compared to AML cells (FIG. 1A, 1B). Data in FIG. 1A is representative of three independent experiments, and data shown in FIG. 1B is the average intensity from a representative experiment ($p<0.05$). This pattern of expression was also confirmed by western blotting with Numb protein band shown at approximately 65-70 kDa (FIG. 1C, data is representative of four independent experiments). As shown in FIG. 1C, the expression of Numb protein is 2.6 fold higher in CML cells relative to AML cells.

This pattern of expression was also confirmed by real time PCR (FIG. 1D). Briefly, AML and CML cells were sorted and RNA was isolated. The level of Numb was analyzed by real-time PCR (n=7 for CML; n=9 for AML; $p<0.05$), and results were normalized to beta-2-microglobulin expression levels.

Example 3

Numb Versus Notch Signaling in CML and AML

Figure 2:
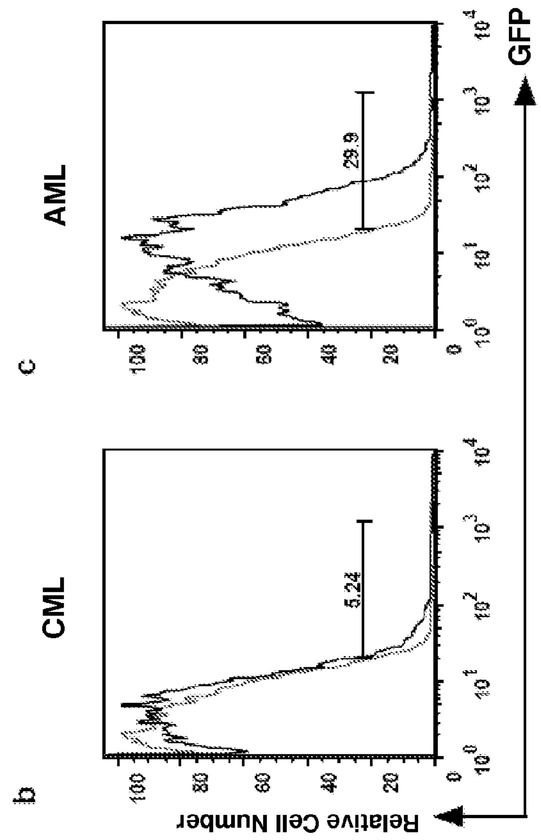
FIG. 2A is a schematic diagram of the strategy used to detect Notch signaling in AML and CML cells.
FIG. 2B is a graph of GFP reporter expression (black line; GFP expression reflects Notch signalling) in CML cells.
FIG. 2C is a graph of GFP reporter expression in AML cells, with expression in wild type cells (gray line) used as a control.
Figure 2:
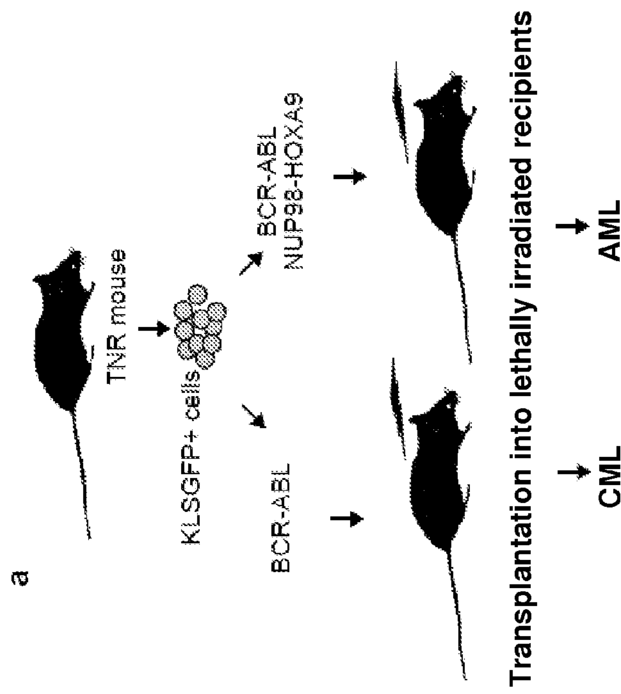

It was tested whether the activation of Numb corresponded to a decrease in Notch signaling in CML and AML. The Transgenic Notch Reporter (TNR) for mice was used, in which GFP expression reflects the status of Notch signaling (Wu, M. et al. *Cell Stem Cell* 2007, 1, 541-54; Duncan, A. W. et al. *Nat Immunol* 2005, 6, 314-22; Estrach, S., Ambler, C. A., Lo Celso, C., Hozumi, K. & Watt, F. M. *Development* 2006, 133, 4427-38; Lai, A. Y. & Kondo, M. *Proc Natl Acad Sci USA* 2007, 104, 6311-6; Hellstrom, M. et al. *Nature* 2007, 445, 776-80; all incorporated herein by reference in their entireties). GFP+KLS cells from TNR mice were sorted and infected with either BCR-ABL (to generate CML) or BCR-ABL and NUP98-HOXA9 (to generate AML), and infected cells were transplanted into irradiated recipients (FIG. 2A). Following transplantation and leukemia development, leukemia cells were isolated from bone marrow and analyzed for GFP fluorescence reporter activity using FACS analysis. While about 5% of CML cells were positive for GFP, 30% of AML cells were positive for GFP (FIG. 2B, 2C). Leukemia cells from wild type mice were used as negative control for GFP expression (n=3 for CML; n=4 for AML). This suggested that the low levels of Numb detected in AML correspond with increased Notch signaling.

The pattern of Numb and Notch signaling in AML essentially corresponded to the rise in the frequency of undifferentiated cells and suggested that the Numb-Notch pathway may play a functional role in inhibiting differentiation during AML establishment. To test whether upregulation of Notch signaling could drive the conversion of chronic leukemia to a more undifferentiated state, the constitutively active intracellular domain of Notch1 (ICN) was used (Carlesso, N., Aster, J. C., Sklar, J. & Scadden, D. T. *Blood* 1999, 93, 838-48, incorporated herein by reference in its entirety). Not only wild type mice were used but also Rag1 deficient (Rag1−/−) mice in which lymphoid development is blocked (Mombaerts, P. et al. *Cell* 1992, 68, 869-77, incorporated herein by reference in its entirety). c-kit+ or KLS cells were infected with BCR-ABL (n=18), ICN/Vector (n=11), or BCR-ABL/ICN (n=16), and transplanted into irradiated recipient mice. Analysis of survival over a period of 90 days revealed that activation of Notch signaling decreased the latency of leukemia driven by BCR-ABL (FIG. 3A). Data shown in FIG. 3A is a combination of 4 independent experiments (BCR-ABL/ICN versus ICN/Vector, $p<0.0001$; BCR-ABL/ICN versus BCR-ABL/Vector, $p=0.0194$).

Figure 3:
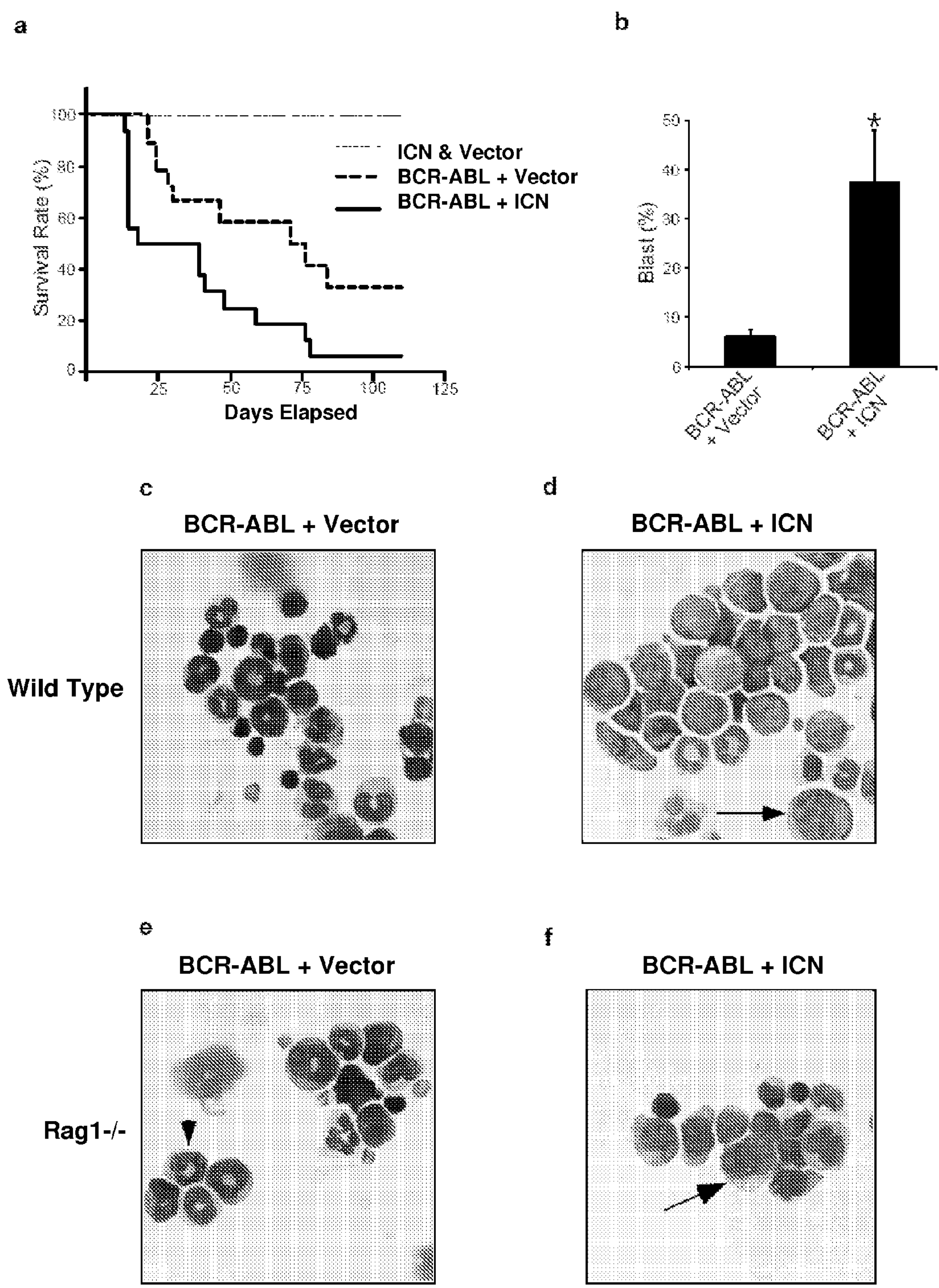
FIG. 3A is a graph of the survival rate of wild type or Rag1−/− mice that were transplanted cells transduced with BCR-ABL/Vector, ICN/Vector, or BCR-ABL/ICN.
FIG. 3B is a graph of the average percentage of blasts in leukemias transduced with BCR-ABL/ICN or BCR-ABL/Vector.
FIG. 3C is an image of wright stained cells derived from wild type BCR-ABL/Vector driven leukemia.
FIG. 3D is an image of wright stained cells derived from wild type BCR-ABL/ICN driven leukemia.
FIG. 3E is an image of wright stained cells derived from Rag1−/− BCR-ABL/Vector driven leukemia.
FIG. 3F is an image of wright stained cells derived from Rag1−/− BCR-ABL/ICN driven leukemia.

The average percentage of blasts in leukemias from BCR-ABL/ICN versus BCR-ABL/Vector was also compared. As shown in FIG. 3B, a significantly higher percentage of blasts were found in leukemias from BCR-ABL+ ICN ($p=0.044$; error bars show s.e.m.). The analysis included data from all mice that could be analyzed before succumbing to disease (for BCR-ABL/ICN n=6 wild type, and n=6 Rag 1−/− out of a total of 16 transplanted; for BCR-ABL/vector n=3 wild type and n=4 Rag-1−/− out of a total of 18 transplanted). As shown in FIG. 3B, the cooperative effect of BCR-ABL and ICN led to more undifferentiated leukemias, with control leukemias containing on average 6% myeloid blasts and BCR-ABL/ICN leukemias containing on average 35% myeloid blasts. Cells derived from wild type BCR-ABL/Vector driven leukemias (FIG. 3C), BCR-ABL/ICN driven leukemias (FIG. 3D), Rag1−/− BCR-ABL/Vector driven leukemias (FIG. 3E), BCR-ABL/ICN driven leukemias (FIG. 3F) were also compared, based on morphological analysis after wright staining splenocytes. Differentiated myeloid cells are indicated by arrowheads, and myeloblasts are indicated by arrows in FIG. 3 (magnification 100×). Although a majority of BCR-ABL/ICN leukemias derived from wild type cells were of the myeloid lineage (66%, 4/6, FIG. 3C, 3D), two displayed elements of lymphocytic leukemia (33%, 2/6, data not shown). In contrast, all BCR-ABL/ICN leukemias derived from Rag1−/− mice were of the myeloid lineage (100%, 6/6, FIG. 3E, 3F), allowing a clearer assessment of ICN contribution to myeloid leukemia progression. Cumulatively the data from both wild type and Rag1−/− mice suggested that activation of Notch signaling can inhibit differentiation and thereby drive the conversion of chronic myelogenous leukemias to a more undifferentiated state and a more aggressive form of cancer.

Example 4

Numb Induces Differentiation of Undifferentiated Leukemias

It was tested whether Numb had the ability to convert undifferentiated leukemias to a more differentiated state, and thus slow disease progression. Bone marrow c-kit+ cells were infected with BCR-ABL and NUP98-HOXA9 together with either control vector or Numb. The cells were transplanted, and survival and leukemia progression was monitored. 83% of BCR-ABL/NUP98-HOXA9/Vector (control) mice and 63% of those transplanted with BCR-ABL/NUP98-HOXA9/Numb developed leukemia (FIG. 4A; data shown is from four independent experiments; n=18 for Vector and n=19 for Numb). Cells were also analyzed via FACS for frequency of lineage negative cells to determine and compare the level of differentiation in the BCR-ABL+NUP98-HOXA9/Numb and BCR-ABL+NUP98-HOXA9/Vector cells. Results indicated that the relative survival increase in cells expressing Numb was consistent with leukemias developed in the presence of Numb that displayed increased differentiation (FIG. 4B; cells were analyzed for frequency of lineage negative cells). Specifically, while the frequency of lineage negative immature cells was on average 47% in control leukemias, it was reduced to 12.3% in Numb expressing leukemias (FIG. 4C; p<0.001; error bars shown s.e.m.). This showed that re-expression of Numb depleted the most immature fraction of AML and converted it to a more differentiated disease.

Secondary transplants were carried out to test the ability of control and Numb expressing AML cells to propagate disease in secondary recipients. Cells from primary transplanted mice were sorted and transplanted, and the mice were monitored for secondary disease. As shown in FIG. 4D (data shown is from two independent experiments; n=14 for Vector; n=15 for Numb; **p<0.001), control AML cells were able to propagate disease in nearly all of the mice (8/9, 89%), but Numb expressing AML cells were significantly impaired in their ability to propagate the disease and lead to a significant decrease in AML incidence (2/10, 20%). Importantly, the few leukemias that did develop in the presence of Numb were less aggressive than control leukemias.

Hematoxylin and Eosin staining of Spleen sections from leukemic Vector infected transplants (FIGS. 4E and 4H), leukemic Numb infected transplants (FIGS. 4F and 4I; disease at 40 days), and healthy Numb infected transplants (FIG. 4G, 4J; sacrificed at 150 days) were prepared to analyze the morphology of the cells. In FIG. 4E-4J, cells were stained with Hematoxylin and Eosin, and magnification is 10× (E-G) or 63× (H-J), with red arrows indicating areas of immature myeloid cells and black arrows indicating lymphoid follicles. Error bars in all bar graphs are s.e.m. Data shown is representative of three to four independent experiments. While spleen sections from control leukemias displayed extensive myeloid cell infiltration (FIGS. 4E and 4H red arrows), and few remaining areas of normal lymphoid follicles, spleen sections from leukemias expressing Numb showed greater preservation of lymphoid follicles (FIGS. 4F and 4I, black arrows). In addition, surviving mice transplanted with Numb AML cells that were sacrificed and analyzed at 150 days displayed normal splenic architecture and had no indication of leukemogenesis (FIGS. 4G and 4J). These data indicate that when expressed during disease initiation, Numb can impair both the incidence and progression of acute myeloid leukemia by inducing differentiation.

The ability of Numb to influence AML progression after disease had been established was also tested. Fully developed AML cells were infected with either vector or Numb, and colony-formation was assessed in vitro using a serial replating assay (Zhao, C. et al. *Cancer Cell* 2007, 12, 528-41; Huntly, B. J. et al. *Cancer Cell* 2004, 6, 587-96; both incorporated herein by reference in their entireties). AML cells were infected with either control Vector-GFP (MSCV-IRES-GFP) or Numb-GFP (MSCV-Numb-IRES-GFP), plated on methylcellulose, and colony numbers were counted. For secondary plating, cells from primary plating were harvested, replated, and colonies counted (n=3, p<0.05). While Numb expression did not alter AML colony formation in the primary plating (FIG. 5A) it led to 3-fold fewer colonies compared to control by the secondary plating (FIG. 5B). Error bars in FIGS. 5A and 5B indicate s.e.m.

To test the influence of Numb on the growth of established AML in vivo, AML cells were isolated, infected with either vector or Numb, and transplanted into irradiated mice. Survival was monitored over time and compared. The incidence and latency of the disease in both groups were similar in the primary transplant (FIG. 5C). However, when cells were analyzed via FACS for frequency of lineage negative cells to determine and compare the level of differentiation in the AML cells with and without Numb, the leukemias differed in their cellular composition, with Numb expressing leukemias showing a significant decrease in undifferentiated lineage negative cells compared to control (36% vs. 63% FIG. 5D, 5E; p=0.0496; error bars show s.e.m.). FIG. 5E shows the average percentage of Lin− cells from primary transplanted mice. FIG. 5F shows representative examples of cancer stem cells frequency (Lin−Sca1+Flk2+CD150−) in primary leukemias. FIG. 5G shows the average cancer stem cell frequency in primary leukemias (control vector, n=3 and Numb, n=4; one statistical outlier from the Numb cohort was excluded based on Grubb's test, p=0.045).

Figure 5:
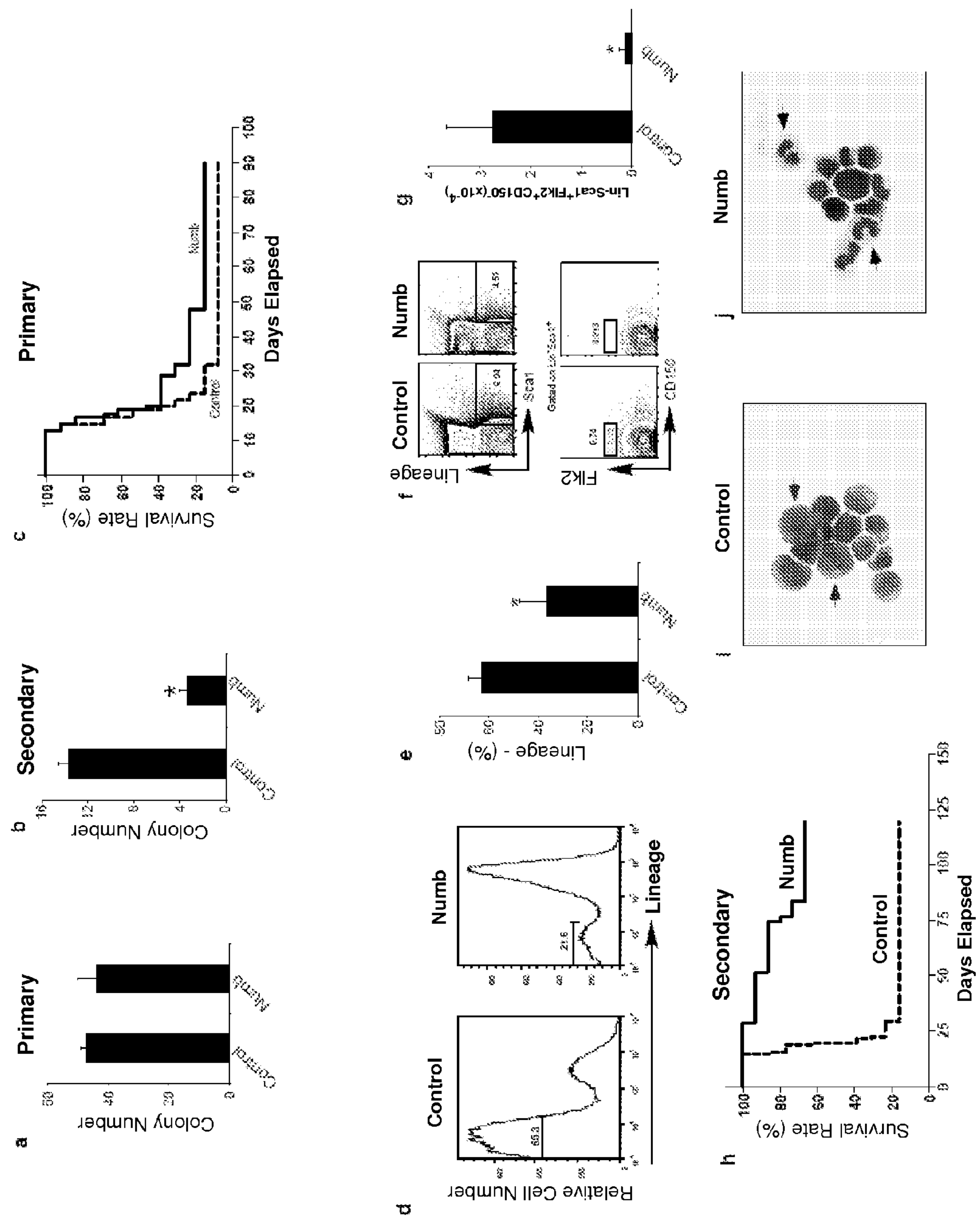
FIG. 5A is a graph of primary colony number for AML cells infected with either control Vector-GFP or Numb-GFP.
FIG. 5B is a graph of secondary colony number for AML cells infected with either control Vector-GFP or Numb-GFP.
FIG. 5C is a graph of the survival of mice transplanted with AML cells infected with either vector or Numb.
FIG. 5D is a graph of a representative example of lineage analysis for leukemic spleen cells from primary transplanted mice, wherein AML cells were analyzed for frequency of lineage negative population.
FIG. 5E is a graph of the average percentage of lineage negative population from primary transplanted mice.
FIG. 5F is the cancer stem cell frequency in primary leukemias.
FIG. 5G is a graph of the average stem cell frequency in primary leukemias.
FIG. 5H is a graph of the survival rate of mice transplanted with cells from primary transplanted mice that were sorted for donor derived cells.
FIG. 5I is an image of leukemic spleen cells from secondary transplanted mice infected with control Vector-GFP, with representative myeloblasts indicated by arrows.
FIG. 5J is an image of leukemic spleen cells from secondary transplanted mice infected with Numb-GFP, with representative differentiated myeloid cells indicated by arrows.
Figure 6:
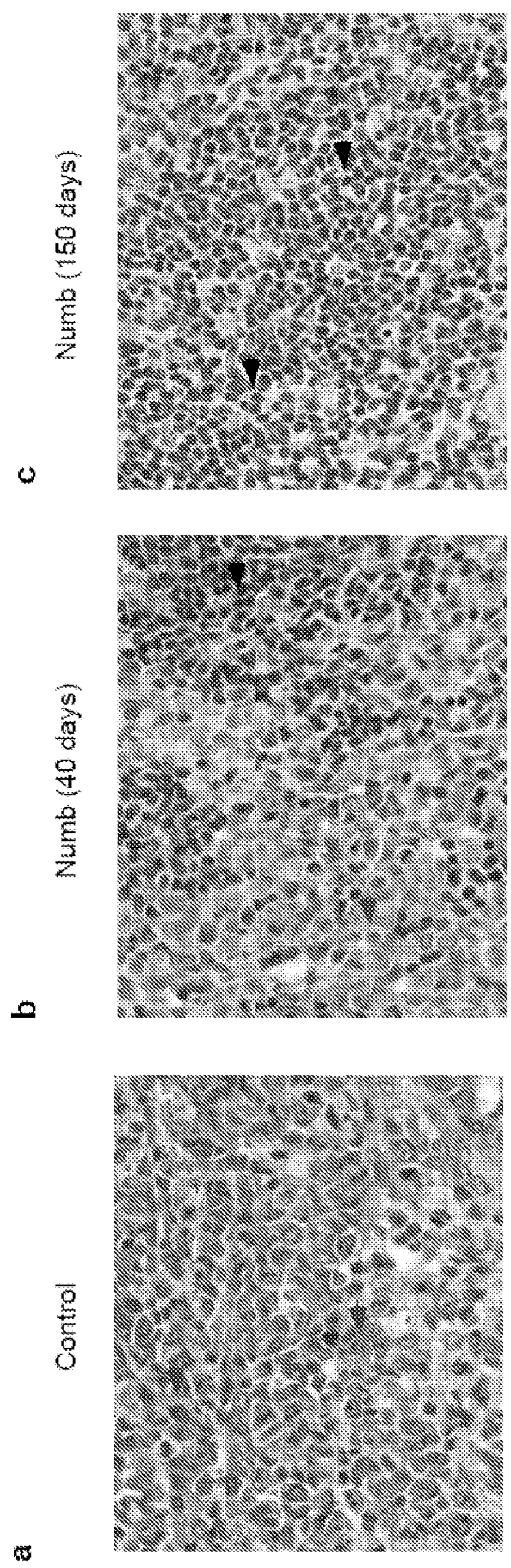
FIG. 6 are hematoxylin and eosin stained spleen sections from mice transplanted with (6A) leukemic vector infected transplants, (6B) leukemic Numb infected transplants, and (6C) healthy Numb infected transplants.

In addition, cells from primary transplanted mice were sorted for donor derived cells, transplanted into irradiated recipients, and the survival of these mice was monitored. As shown in FIG. 5H (data shown is from three independent experiments; n=13 for Vector; n=15 for Numb; p=0.0002), Numb had a significant impact on disease progression in secondary transplants. While 78% (7/9) of mice transplanted with control cells succumbed to leukemia, only 30% (3/10) of mice transplanted with Numb expressing AML cells developed disease. Leukemic spleen cells from secondary transplanted mice with AML/Vector (FIG. 5I) or AML/Numb (FIG. 5J) were cytospun and Wright stained, and it was observed from the morphology that the leukemias that did develop in the presence of Numb were significantly more differentiated (arrows indicate myeloblasts in FIG. 5I and differentiated myeloid cells in FIG. 5J; magnification is 100×). These data indicated that continual Numb repression may be important to AML establishment as well as maintenance even after the disease is fully established. Importantly, leukemias that developed in the presence of Numb were more differentiated (FIG. 4B, 4C), and unable to propagate disease efficiently (93% versus 20%, FIG. 1*g*) or infiltrate secondary organs (FIG. 4E, 4F, FIG. 6); no signs of leukemia were detected in mice that survived (FIG. 4G, FIG. 6). Numb also impaired propagation of fully established leukemias and dramatically reduced the frequency of cancer stem cells (FIG. 5). Shown in FIG. 6 are leukemic cells from mice transplanted with control- or Numb-expressing blast crisis CML that were sorted, transplanted, and spleen sections obtained and analyzed. Shown are hematoxylin and eosin staining of spleen sections from a, leukemic vector infected transplants (FIG. 6A), leukemic Numb infected transplants (disease at 40 days, FIG. 6B), and healthy Numb infected transplants (sacrificed at 150 days, FIG. 6C). Original magnification was at 63×, red arrows indicate areas of immature myeloid cells, and black arrows indicate lymphoid follicles. These data show that continual repression of Numb is essential for maintenance of blast crisis CML, and that increasing the levels of Numb can inhibit disease.

Example 5

Relationship of Numb and Notch in CML

It was tested whether Numb and Notch had a reciprocal relationship in CML. Notch signaling was elevated in blast crisis CML (FIG. 7). Notch signaling was differentially active in chronic and blast crisis CML. FIG. 7A shows a schematic of the strategy to detect Notch signaling in chronic and blast crisis CML. KLS GFP+ cells from transgenic Notch reporter mice (TNR) were sorted and infected with either BCR-ABL to generate chronic phase disease or BCR-ABL and NUP98-HOXA9 to generate blast crisis CML. Infected cells were transplanted into irradiated recipients (chronic phase, n=3 and blast crisis, n=4). Following leukemia development, cells were isolated from the bone marrow and analyzed by FACS for TNR reporter activity as assessed by GFP expression. FIGS. 7B and 7C show GFP expression (black line) in donor derived cells from (B) chronic and (C) blast crisis CML. Leukemia cells from wild type mice were used as negative control for GFP (gray line). FIGS. 7D and 7E show blast crisis CML cells from TNR mice were sorted for GFP low and GFP high, cytospun and immunostained with anti-cleaved Notch1 antibody (red) and DAPI (blue). Presence of ICN was higher in GFP high cells confirming Notch reporter activity correlated with cleaved ICN.

Figure 8:
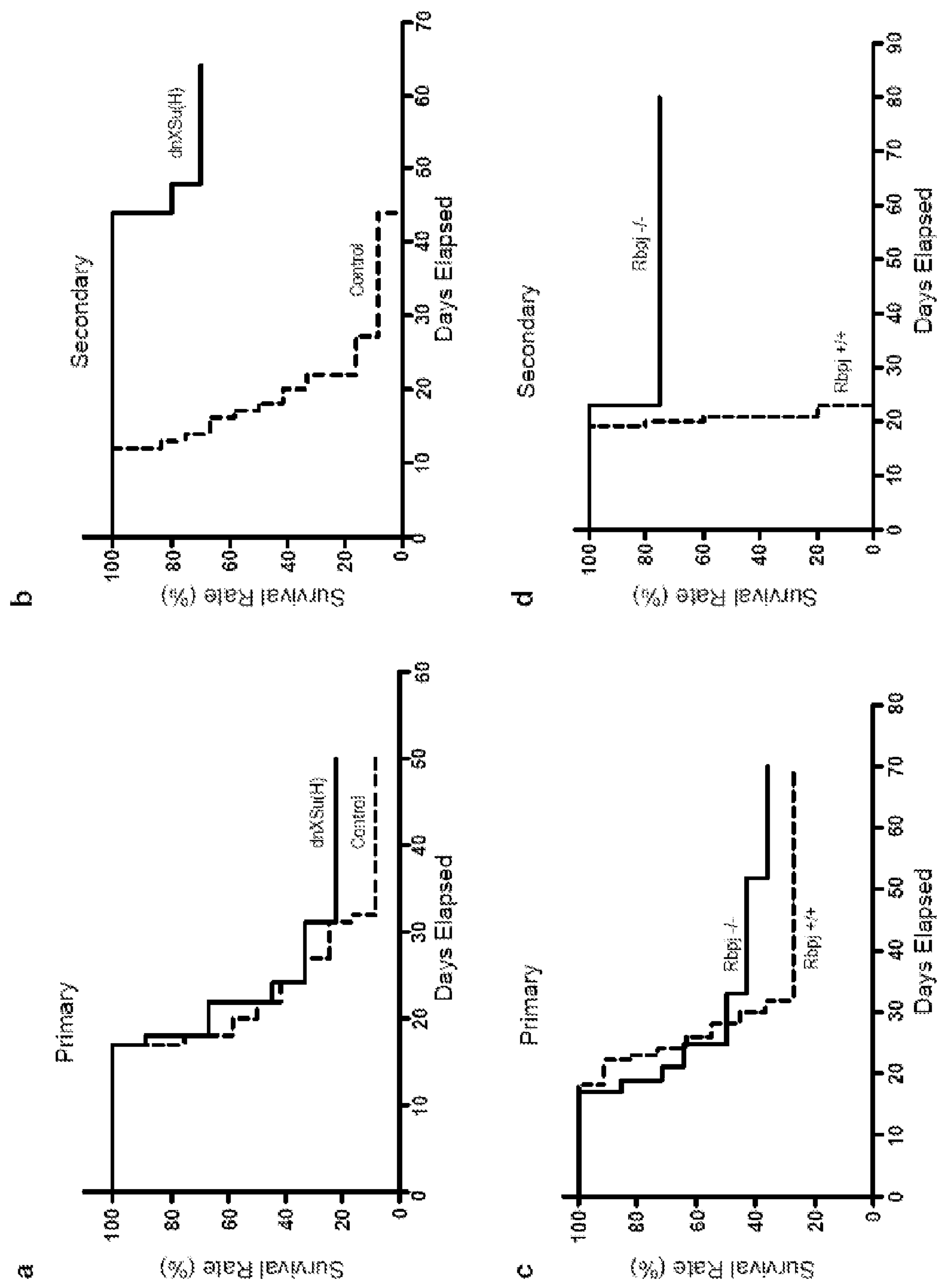
FIG. 8A shows survival for blast crisis CML cells that were infected with either vector control or dominant negative Xenopus Suppressor of Hairless (dnXSu(H)), sorted, and transplanted into irradiated recipients.
FIG. 8B shows survival for cells from primary transplanted mice that were sorted for donor-derived cells and serially transplanted into irradiated recipients.
FIG. 8C shows survival for bone marrow progenitors from control (+/+) mice or conditional Rbpj knockout (Rbpj−/−) mice that were infected with NUP98-HOXA9 and BCR-ABL and transplanted into irradiated recipients.
FIG. 8D shows survival for cells from primary transplanted mice that were sorted for donor-derived cells and serially transplanted into irradiated recipients.

Notch signaling inhibition via dnXSu(H) delivery or through conditional deletion of Rbpj paralleled the effects of Numb and led to reduced incidence and propagation of blast crisis CML (FIG. 8) Inhibition of Notch signaling lead to impaired development and propagation of blast crisis CML. FIG. 8A shows data for blast crisis CML cells that were infected with either vector control or dominant negative Xenopus Suppressor of Hairless (dnXSu(H)), sorted, transplanted into irradiated recipients, and survival monitored. Data shown is from two independent experiments (Vector, n=10 and dnXSu(H), n=9, p=0.66). FIG. 8B shows data for cells from primary transplanted mice that were sorted for donor-derived cells, serially transplanted into irradiated recipients, and survival monitored. Data shown is from two independent experiments (n=10, p<0.0001). FIG. 8C shows data for bone marrow progenitors from control (+/+) mice or conditional Rbpj knockout (Rbpj−/−) mice that were infected with NUP98-HOXA9 and BCR-ABL, transplanted into irradiated recipients, and survival monitored. Data shown is from three independent experiments (wild type, n=11 and Rbpj−/−, n=14, p=0.809). FIG. 8**D shows data for cells from primary transplanted mice that were sorted for donor-derived cells, serially transplanted into irradiated recipients, and survival monitored (Vector, n=5 and Rbpj−/−, n=4, *p=0.012).

Figure 9:
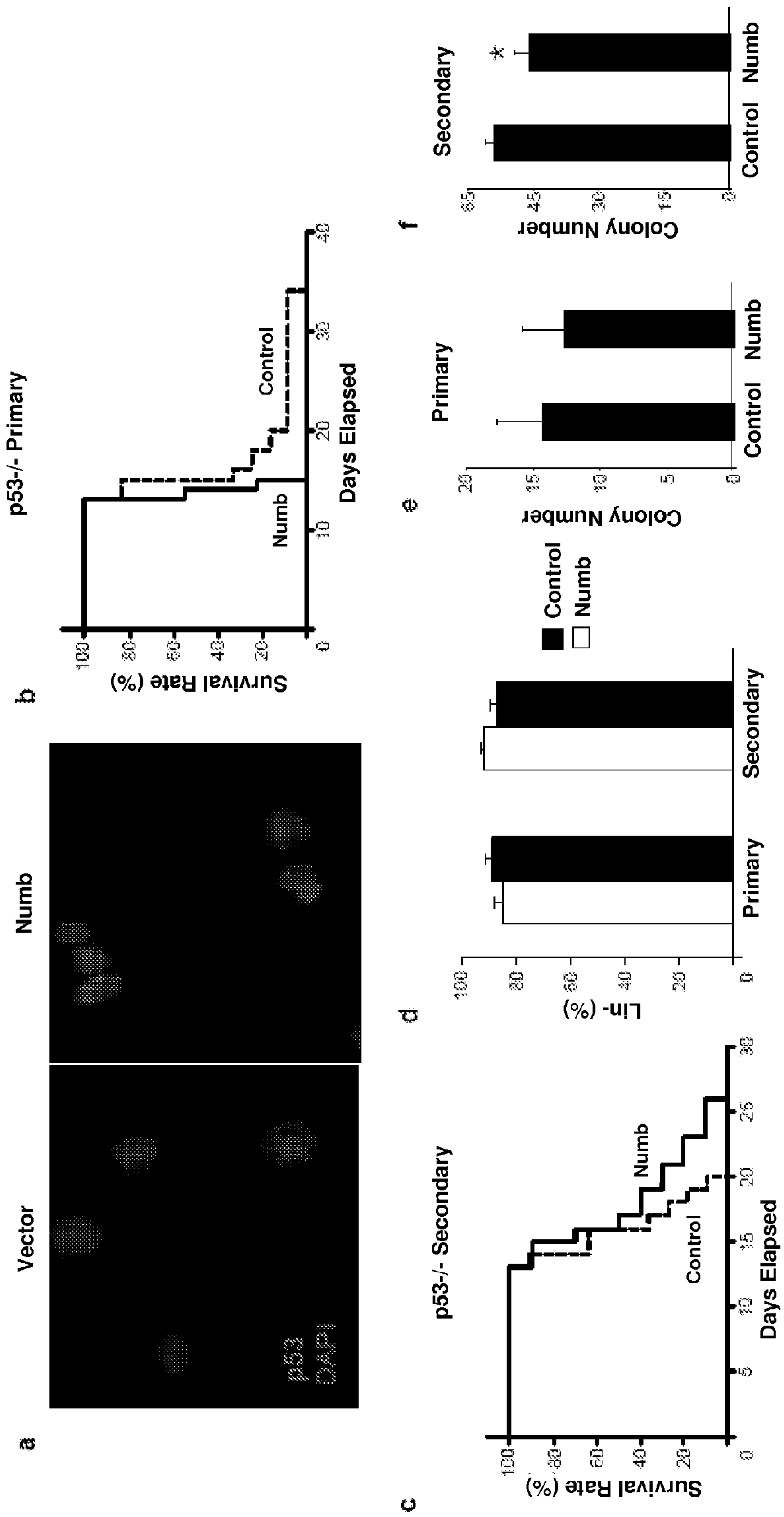
FIG. 9A shows Lin− cells from Vector- or Numb-expressing NUP98-HOXA9/BCR-ABL-induced leukemia that were sorted, cytospun, and immunostained with anti-p53 and DAPI.
FIG. 9B shows survival for bone marrow cells from p53 null mice (p53−/−) that were infected with BCR-ABL and NUP98-HOXA9 together with either Vector or Numb and transplanted into irradiated recipients.
FIG. 9C shows survival for donor-derived cells from primary transplants that were re-transplanted and monitored for secondary disease.
FIG. 9D shows the frequency of the Lin− population from primary and secondary leukemia.
FIG. 9E shows the number of colonies from cells from primary transplants that were sorted and plated in methylcellulose media.
FIG. 9F shows the number of colonies from cells from primary plating that were harvested and replated for secondary colonies.

In addition, levels of p53, another Numb target, were higher in Numb-expressing blast crisis CML (FIG. 9A). In the absence of p53, Numb was unable to impact leukemic cell growth in vivo or in vitro (FIG. 9B-F), indicating that Numb's effects are in part dependent on p53. Loss of p53 impaired Numb's ability to inhibit blast crisis CML propagation. FIG. 9A shows Lin− cells from Vector- or Numb-expressing NUP98-HOXA9/BCR-ABL-induced leukemia that were sorted, cytospun, and immunostained with anti-p53 (red) and DAPI (blue). FIG. 9B shows data for bone marrow cells from p53 null mice (p53−/−) that were infected with BCR-ABL and NUP98-HOXA9 together with either Vector or Numb, transplanted into irradiated recipients, and survival monitored. Data shown are from three independent experiments (Vector, n=10 and Numb, n=9, p=0.0149). FIG. 9C shows data for donor-derived cells from primary transplants that were re-transplanted and survival monitored for secondary disease. Data shown are from two independent experiments (Vector, n=9 and Numb, n=10, p=0.0918). FIG. 9D shows the frequency of the Lin− population from primary and secondary leukemia. Error bars show s.e.m. For primary: Vector, n=7 and Numb, n=5; secondary: Vector, n=7 and Numb, n=9. For FIG. 9E, cells from primary transplants were sorted, plated in methylcellulose media, and colony numbers counted. Error bars show s.e.m. (n=2). For FIG. 9F, cells from primary plating were harvested and replated for secondary colonies (*p=0.029). Data is representative of two independent experiments. Error bars show s.e.m.

Example 6

Numb Expression is Diagnostic for Imatinib Non-Responsiveness

It was next tested whether Numb is differentially expressed in human CML, imatinib resistant CML, and blast crisis CML (bcCML) cells in human disease. CML cells were subdivided into two groups: CML with major or complete molecular response (MMR or CMR), which can be easily cured with Imatinib Mesylate (IM), and CML with no MMR, which may relapse after Imatinib Mesylate (IM) treatment. The average BCR-ABL transcript of CML with MMR or CMR was 0.033% on the International Scale (IS), whereas that of CML with no MMR was 2.055% IS 12 months after IM treatment. To analyze Numb expression in these samples, CML cells from bone marrow cells were collected from human CML and bcCML patients before IM treatment. The bone marrow were purified, RNA was isolated, and the level of Numb expression was analyzed by realtime PCR with results normalized to actin expression levels (n=5 for CML with MMR or CMR; p=0.07 and n=4 for CML with no MMR; p=0.03 and n=0.03 for bcCML). Numb expression levels in CML with MMR or CMR was higher compared to CML with no MMR and bcCML (FIG. 10). These data suggest that Numb expression is downregulated as disease becomes more aggressive, and Numb could be used as a prognostic marker for imatinib non-responsiveness within CML patients.

Example 7

Musashi as a Therapeutic for Acute and Blast Crisis Myeloid Leukemia

The expression levels of the two paralogous mammalian Musashi genes, Msi1 and Msi2, were examined using real time PCR. KLS cells were sorted, and RNA was extracted and reverse transcribed. Following equalization of template cDNA, Msi1 and Msi2 transcript expression was analyzed by realtime PCR. It was found that Msi2 was dominant in normal and transformed hematopoietic cells, while Msi1 was barely detectable in these tissues.

Subsequent studies focused on Msi2. CML and AML cells were sorted from spleen, RNA was extracted and reverse transcribed, and Msi2 expression levels were determined by realtime PCR with results normalized to beta-2-microglobulin. Msi2 expression was 10-fold higher in AML than in CML (FIG. 11A; CML, n=6; AML, n=9; error bars represent s.e.m. p<0.001). AML cells were sorted into $Lin^-$ or $Lin^+$ fractions based on the expression of lineage markers, and Msi2 levels were analyzed. As shown in FIG. 11B (n=5 for each group; p=0.039; error bars represent s.e.m.), the expression of Msi2 was further enriched in the lineage negative fraction within AML. These data indicated that Msi2 expression is associated with the most immature leukemic cells.

Figure 12:
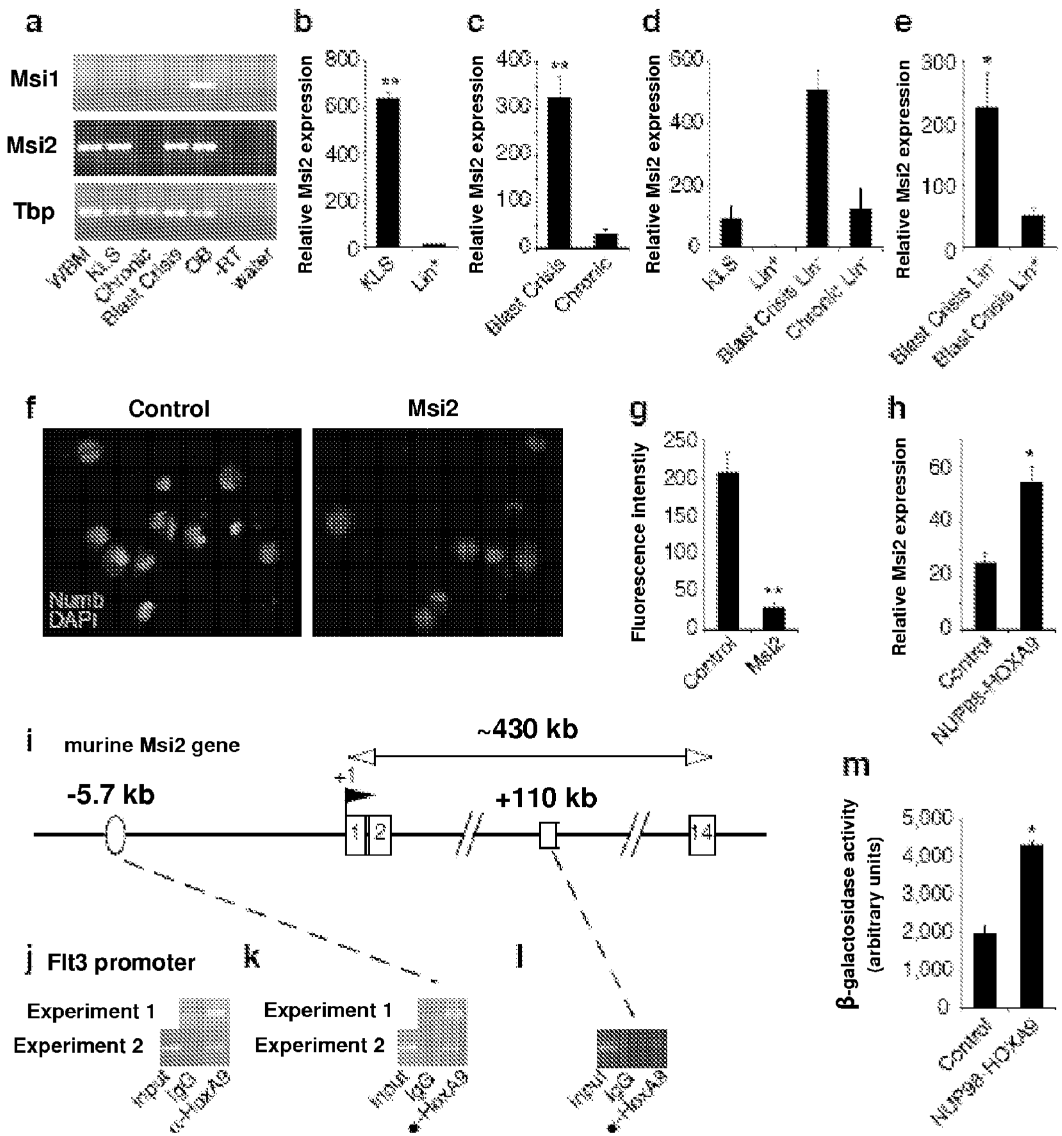
FIG. 12A shows Musashi (Msi) expression in whole bone marrow (WBM), KLS cells, chronic and blast crisis CML, olfactory bulb (OB), −reverse transcriptase (−RT in OB), and water.
FIG. 12B is a graph of Msi2 expression as determined by Realtime PCR in KLS cells and $Lin^+$ cells.
FIG. 12C is a graph of Msi2 expression as determined by Realtime PCR in blast crisis phase and chronic phase cells.
FIG. 12D is a graph of Msi2 expression as determined by Realtime PCR in $lin^-$ chronic and blast crisis phase cells relative to normal KLS and $lin^+$ cells.
FIG. 12E is a graph of Msi2 expression as determined by Realtime PCR in $lin^-$ or $lin^+$ blast crisis CML cells.
FIG. 12F are control vector- or Msi2-expressing CML cells that were stained with anti-Numb antibody and DAPI.
FIG. 12G is a graph of fluorescence intensity quantified for the cells in 12F.
FIG. 12H is a graph of Msi2 expression in KLS cells transduced with either control vector or NUP98-HOXA9 retrovirus along with BCR-ABL.
FIG. 12I is a schematic diagram of the murine Msi2 gene structure.
FIG. 12J shows ChIP performed either with IgG control or anti-HoxA9 antibody for Flt3.
FIG. 12K shows ChIP performed either with IgG control or anti-HoxA9 antibody for Msi2 −5.7 kb region.
FIG. 12L shows ChIP performed either with IgG control or anti-HoxA9 antibody for Msi2 +110 kb region.
FIG. 12M shows β-galactosidase reporter activity for KLS cells from Msi2 genetrap reporter mice that were transduced with BCR-ABL with either control vector or NUP98-HOXA9.

In the hematopoietic system it was found that Msi2 was expressed at much higher levels than Msi1 (FIG. 12A), and was particularly elevated in stem cells (FIG. 12B). FIG. 12A shows Musashi (Msi) expression in whole bone marrow (WBM), KLS cells, chronic, and blast crisis CML, olfactory bulb (OB), −reverse transcriptase (−RT in OB), and water (Tbp stands for TATA binding protein). FIG. 12B shows results for Realtime RT-PCR analysis of Msi2 expression in KLS cells (n=3) and Lin+ cells (n=2) (p<0.001). Paralleling this, Msi2 expression was 10-fold higher in the more immature blast crisis CML (FIG. 12C). FIG. 12C shows results for Realtime RT-PCR analysis of Msi2 expression in blast crisis phase (n=9) and chronic phase (n=6) (p<0.001). This pattern held true even in matched lineage negative fractions (FIG. 2D) suggesting that Msi2 upregulation in advanced phase is not simply a consequence of altered cellular composition. FIG. 12D shows results for Realtime RT-PCR analysis of Msi2 expression in lin− chronic and blast crisis phase cells relative to normal KLS and lin+ cells (lin+, n=2 and others, n=3). Finally, expression of Msi2 was most enriched in the lineage negative fraction of blast crisis CML (FIG. 12E). FIG. 12E shows results for Realtime RT-PCR analysis of lin− (n=5) or lin+ (n=5) blast crisis CML cells (*p=0.039). Error bars represent s.e.m. These data indicate that Msi2 expression associates predominantly with normal hematopoietic stem cells and the most immature fraction of leukemic cells.

Since Msi2 and Numb were expressed in a reciprocal pattern, it was examined whether Msi2 could downregulate Numb during leukemogenesis. Isolated CML cells were infected with Msi2-expressing or empty vector. Infected cells were sorted and stained with an anti-Numb antibody, and nuclei were visualized by DAPI staining (pseudo-colored in green in FIG. 12F), to analyze expression of Numb by immunofluorescence (p<0.001). Fluorescence intensity of Numb staining was quantified by Metamorph software, more than thirty cells from each cohort were analyzed, background fluorescence intensity was subtracted from individual fluorescence intensity, and averaged values are shown in FIGS. 12G and 12H (p<0.001). Msi2 significantly decreased the levels of Numb (FIG. 12F right panel and 12G) compared to empty vector control (FIG. 12F left panel and 12**G).

To determine whether the NUP98-HOXA9 oncoprotein itself plays a role in how Msi2 expression is initially upregulated in AML, it was tested if NUP98-HOXA9 can induce Msi2 expression. KLS cells were isolated and transduced with BCR-ABL and vector, or BCR-ABL and NUP98-HOXA9. Analysis of Msi2 expression with realtime PCR revealed that the presence of NUP98-HOXA9 led to significantly higher levels of Msi2 (FIG. 12H); data shown are from three independent experiments, *p=0.017), showing that NUP98-HOXA9 could also activate this cascade by increasing expression of Msi2. These data cumulatively suggest that Msi2 is upregulated following NUP98-HOXA9 expression, and that Msi2, through its ability to downregulate Numb, contributed to the establishment and maintenance of acute myeloid leukemia and, at least in part, Msi2 has the ability to activate a cascade that leads to inhibition of differentiation.

Since NUP98-HOXA9 initiates transformation through HoxA9 mediated DNA binding and transcription, it was tested whether HoxA9 could bind the Msi2 promoter and activate its expression directly. As shown in FIG. 12I-L, HoxA9 bound to the Msi2 promoter. Shown in FIG. 12I is the murine Msi2 gene structure: exons (numbered boxes), transcription start site (TSS; +1) and the direction of transcription (flag), putative HOX binding element 5.7 kb upstream of TSS (oval), and +110 kb site with no HoxA9 binding sequence (open rectangle). Chromatin immunoprecipitation (ChIP) was performed either with IgG control or anti-HoxA9 antibody, wherein Flt3, a known HoxA9 target gene, was used as a positive control (FIG. 12J). Msi2 −5.7 kb region (FIG. 12K) or Msi2 +110 kb region (FIG. 12L) were also used as a positive control. The ChIP revealed that HoxA9 was in fact associated with the putative HoxA9 binding element that was identified at −5.7 kb.

As shown in FIG. 12M, KLS cells from Msi2 genetrap reporter mice were transduced with BCR-ABL with either control vector or NUP98-HOXA9 and (β-galactosidase reporter activity quantified (n=2 each, *p=0.011). This indicated that NUP98-HOXA9 expression was also able to induce Msi2 reporter activity in KLS cells. These data show that Msi2 can be upregulated by NUP98-HOXA9 and subsequently contribute to blast crisis CML by repressing Numb.

Figure 13:
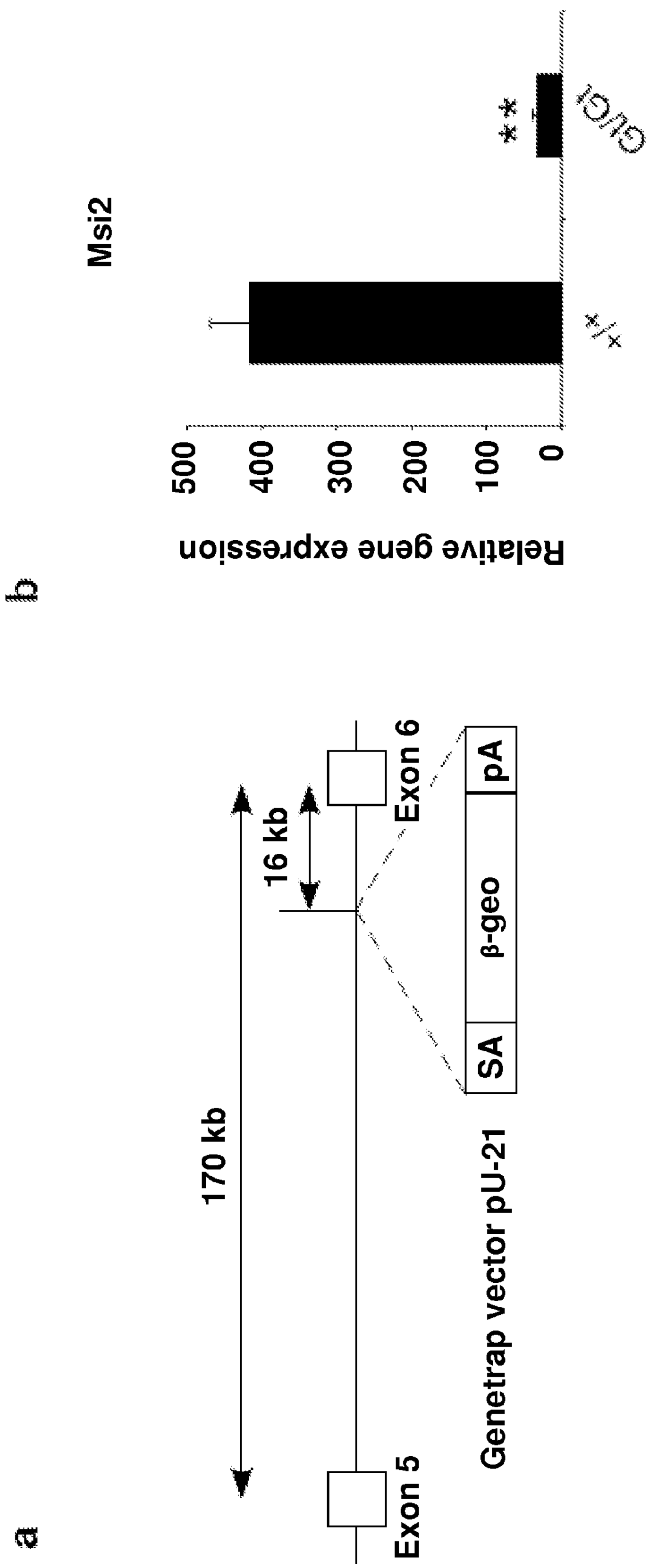
FIG. 13A is a schematic illustration of a Msi2 mutant allele generated by an insertion of a genetrap vector pU-21.
FIG. 13B is a graph of Msi2 expression in whole bone marrow cells from control (+/+) and homozygotes for the genetrap allele (Gt/Gt) as analyzed by Realtime RT-PCR.

To test if Msi2 is required for the development of blast crisis CML, a mouse in which the Msi2 gene was disrupted by a genetrap (Gt) vector was utilized (Taniwaki, T. et al. *Dev Growth Differ* 2005, 47, 163-172, incorporated herein by reference in its entirety). FIG. 13A shows a schematic illustration of a Msi2 mutant allele generated by an insertion of a genetrap vector pU-21. Inverse PCR strategy allowed identification of the location of the genetrap event in intron 5 of Msi2 gene. As genetrap vector pU-21 harbors splice acceptor sequence (SA) and transcription termination/polyadenylation signal (pA) downstream of $^2$-geo sequence, Msi2 gene transcription would be terminated at this site. Shown in FIG. 13B are results from Realtime RT-PCR analysis of Msi2 expression in whole bone marrow cells from control (+/+) and homozygotes for the genetrap allele (Gt/Gt) (n=6 each, **p<0.001). Results shown were normalized to beta-2-microglobulin levels. Error bars represent s.e.m.

Figure 14:
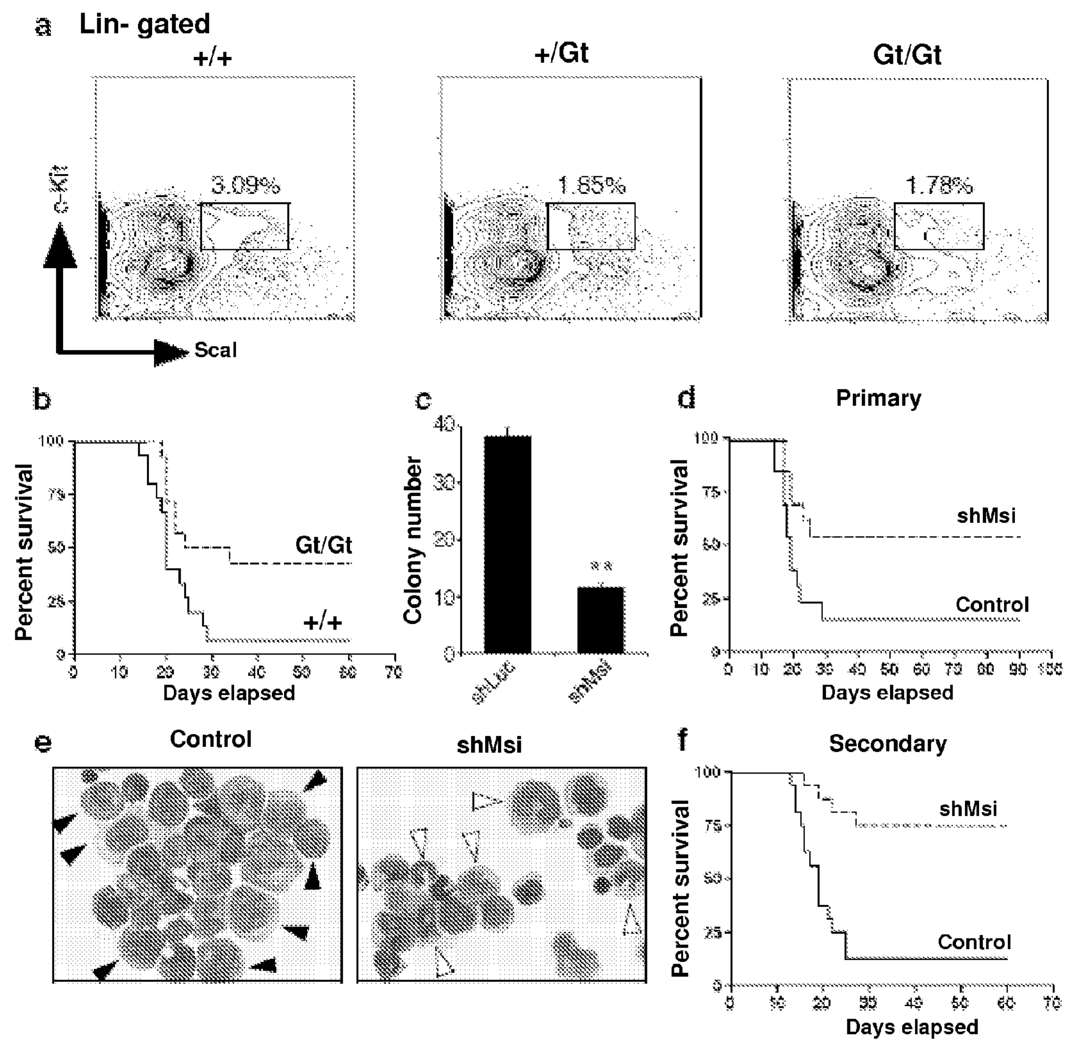
FIG. 14A is the frequency of KLS cells in mice of indicated genotypes (+/+, +/Gt, Gt/Gt).
FIG. 14B shows is a survival curve of mice transplanted with BCR-ABL and NUP98-HOXA9 infected +/+ or Gt/Gt KLS cells.
FIG. 14C is a graph of colony numbers for blast crisis CML cells transduced with control shRNA (shLuc) or Msi2 shRNA (shMsi).
FIG. 14D is a survival curve of mice transplanted with established blast crisis CML cells infected with control shLuc or shMsi.
FIG. 14E are Wright's stain of leukemic cells from mice transplanted with control shLuc or shMsi infected blast crisis CML.
FIG. 14F is a survival curve of mice transplanted with $Lin^-$ cells from primary shRNA expressing leukemias.

Shown in FIG. 14B, is the frequency of KLS cells in mice of indicated genotypes (+/+, n=4, +/Gt, n=3 and Gt/Gt, n=4). Shown in FIG. 14B is the survival curve of mice transplanted with BCR-ABL and NUP98-HOXA9 infected +/+ or Gt/Gt KLS cells (+/+, n=15 and Gt/Gt, n=14, *p=0.0159). Msi2 mutant mice were viable, albeit smaller and less frequent than predicted (+/+:+/Gt:Gt/Gt=38:66:19, p=0.038), and showed a two-three fold reduction in the frequency (FIG. 14A) and absolute numbers (data not shown) of KLS cells. Additionally, the loss of Msi2 led to significantly impaired leukemia growth in vivo (FIG. 14B, 93% for control versus 57% for Gt/Gt).

Figure 15:
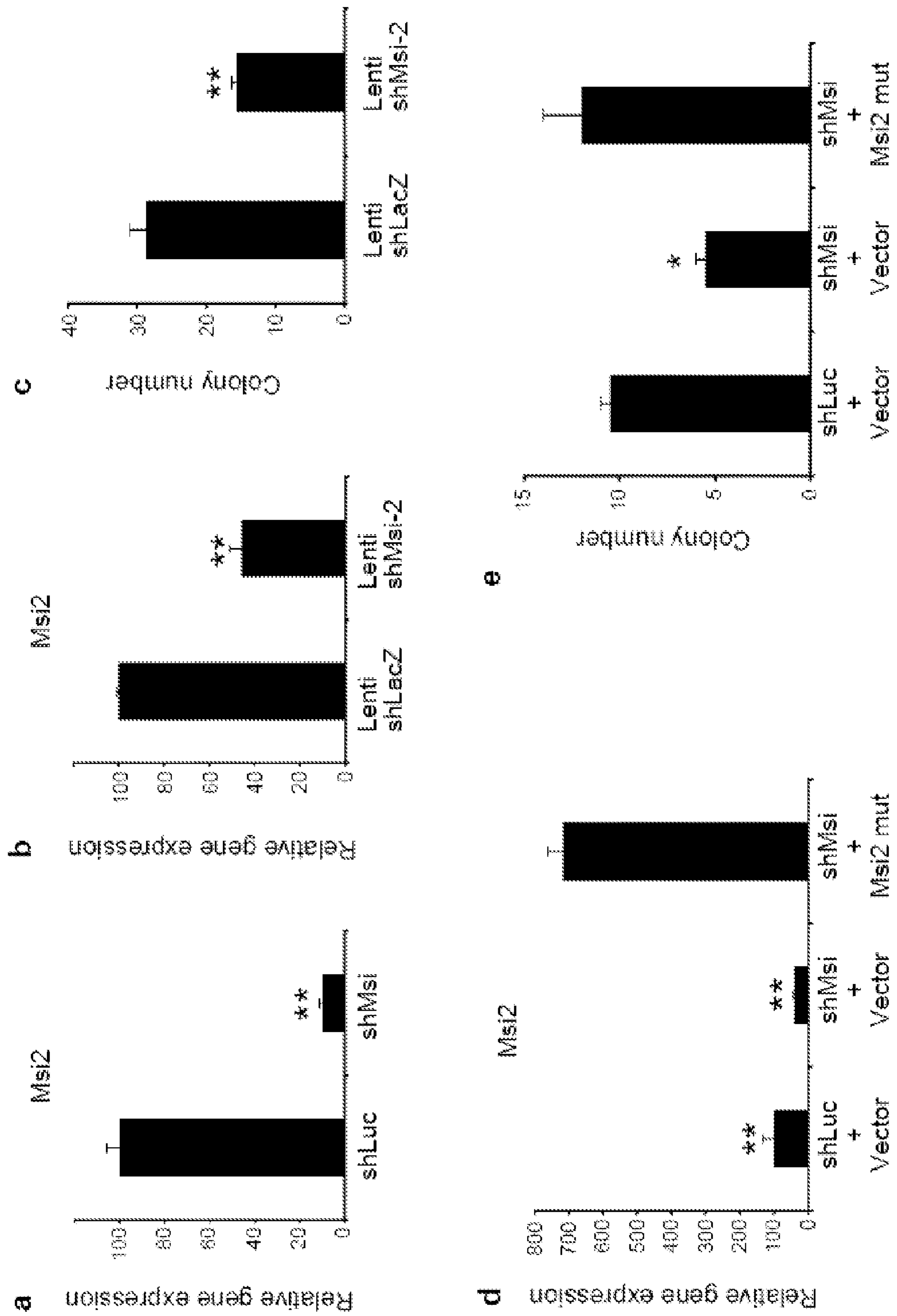
FIG. 15A is a graph of Msi2 expression in Lin− cells from NUP98-HOXA9/BCR-ABL-induced blast crisis leukemias that were infected with either shLuc or shMsi.
FIG. 15B is a graph of Msi2 expression after Msi2 knockdown by an independent lentiviral shRNA construct, shMsi-2.
FIG. 15C is a graph of the number of colonies formed with an independent shRNA construct, shMsi-2.
FIG. 15D is a graph of Msi2 expression in samples expressing the indicated constructs.
FIG. 15E is a graph of the colony-forming ability of the samples in 15D.

To determine if inhibiting Msi2 could impact the growth of established CML, and to rule out the possibility that the reduced incidence of leukemia in Gt mutants was due to developmental defects and examine if Msi2 knockdown affects AML maintenance, Msi expression was targeted using an alternate shRNA approach. A lineage-negative population was sorted from full blown AML cells, which contains AML stem cells. Lin− cells from NUP98-HOXA9/BCR-ABL-induced blast crisis leukemias were infected with either an shRNA retrovirus targeting Msi2 (shMsi; SEQ ID NO: 9) or firefly luciferase (shLuc; SEQ ID NO: 10) as a negative control and resorted, and Msi2 expression was analyzed by real-time RT-PCR. Expression levels were normalized to the level of beta-2 microglobulin and displayed relative to the control arbitrarily set at 100. Error bars represent s.e.m. of triplicate PCRs (p<0.01). Results are shown in FIG. 15**A. Knockdown of Msi2 resulted in 75-90% reduction in Msi2 transcript levels compared with the shLuc control. A colony forming assay was done using methylcellulose media, and it was found that Msi2 knockdown led to 50-70% reduction in the number of colonies formed, suggesting that Msi2 reduction impaired colony forming ability of the AML cells.

Delivery of Msi2 shRNAs (shMsi) into established blast crisis CML cells reduced colony growth in vitro (FIG. 14C and FIG. 15B-E) As shown in FIG. 14C, colony-forming ability of blast crisis CML cells transduced with control shRNA (shLuc) or Msi2 shRNA (shMsi) (p<0.001). FIG. 15B shows Msi2 knockdown by an independent lentiviral shRNA construct, shMsi-2. As a control, shRNA against LacZ was used. Error bars represent s.e.m. of triplicate PCRs (p<0.01). FIG. 15C shows the reduction of colony formation by an independent shRNA construct, shMsi-2. Error bars represent s.e.m. of triplicate assay wells (p<0.01). FIG. 15D shows Msi2 expression levels in samples expressing the indicated constructs (Msi2 mut: shMsi-resistant Msi2 mutant cDNA). Error bars represent s.e.m. of triplicate PCRs (p<0.01). FIG. 15E shows rescue of shMsi2-mediated reduction of colony-forming ability with expression of shMsi-resistant Msi2 mutant cDNA, wherein Lin− cells from blast crisis phase leukemia were transduced retrovirally with either vector control or Msi2 mutant together with the indicated shRNA constructs, sorted and plated in methylcellulose media for colony formation (*p=0.019).

Delivery of Msi2 shRNAs (shMsi) into established blast crisis CML cells also reduced disease incidence in vivo, as shown in the survival curve of mice transplanted with established blast crisis CML cells infected with control shLuc or shMsi (FIG. 14D, n=13 each, *p=0.0267).

Further, the majority of leukemias that occurred in the presence of shMsi were more differentiated (FIG. 14E), and impaired in their ability to propagate disease (FIG. 14F, 87% control versus 25% shMsi). FIG. 14E shows Wright's stain of leukemic cells from mice transplanted with control shLuc or shMsi infected blast crisis CML, with immature myeloblasts (closed arrowheads) and differentiating myelocytes and mature band cells (open arrowheads) indicated (magnification: 100×). FIG. 14F shows the survival curve of mice transplanted with $Lin^-$ cells from primary shRNA expressing leukemias (control, n=15 and shMsi, n=16, **p<0.001). Data shown is representative of two to three independent experiments. These data show that Msi2 is important for establishment and continued propagation of blast crisis CML.

The impact of Msi2 loss in AML propagation in vivo was also tested. Lin− negative cells from full blown AML were transduced either with an Msi2 shRNA retrovirus or luciferase shRNA virus, and the cells were transplanted into sublethally-irradiated mice. 11 of 13 mice transplanted with control knockdown AML became sick by 1 month post transplant. In contrast, more than half of the mice transplanted with Msi2 knockdown AML survived beyond 1 month (FIG. 16). The surviving mice had no detectable levels of transplanted leukemic cells in their peripheral blood, indicating loss of the leukemic cells.

Serial transplants were also done to test the presence of leukemia-initiating ability of control and Msi2 knockdown AML cells from the mice who suffered from leukemia. While control knockdown AML cells were able to propagate disease in 2 out of 3 mice (transplanted with 3000 cells) or all of the mice (4 out of 4 at 10,000 cells transplanted), Msi2-knockdown AML cells were significantly impaired in their ability to initiate AML leading to a loss in AML incidence at either of the cell doses used. These data suggested that AML required Msi2 to be highly expressed during disease maintenance and propagation.

Example 8

Msi2 in Human Leukemia Progression

Figure 17:
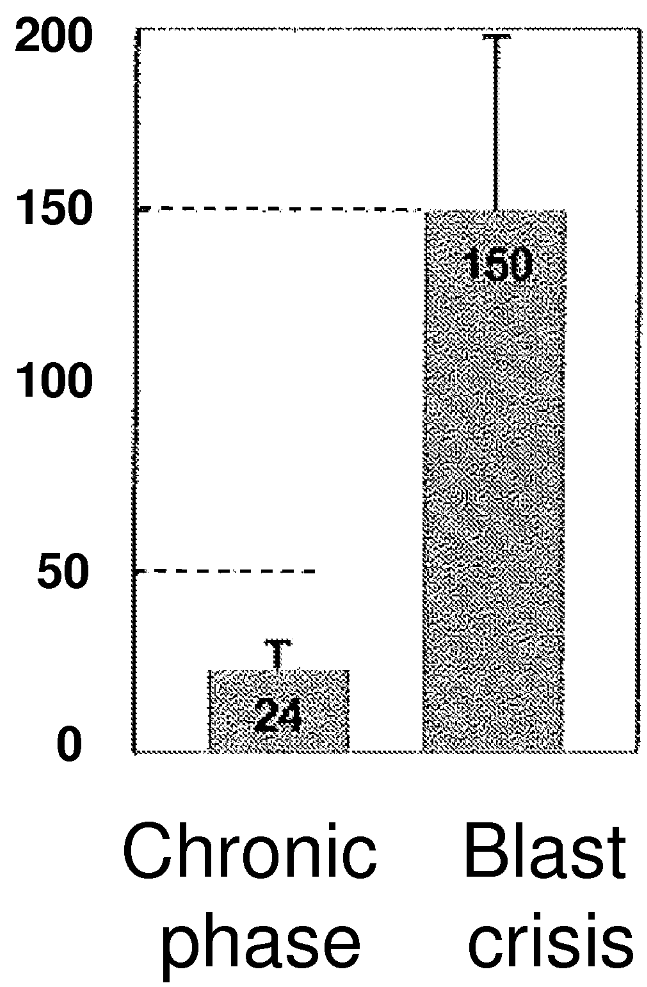
FIG. 17 is a graph of MSI2 expression levels in human chronic phase leukemia and blast crisis leukemia.

To determine if human myeloid leukemias have similar disease progression, the expression levels of Musashi (MSI2) were analyzed in human patient specimens from chronic phase and blast crisis CML patients. 9 specimens were obtained for each of chronic phase (CP) and blast crisis (BC) CML, and cDNA were prepared from the total RNA from these specimens. By using realtime RT-PCR analyses, it was found that the human ortholog MSI2 transcript levels were 6-fold higher in BC CML than in CP CML (FIG. 17) suggesting that a similar mechanism upregulating Musashi operates in both mice and humans to drive blast crisis CML.

Finally, it was examined if MSI2 was aberrantly upregulated during human leukemia progression. MSI2 was tracked in 30 patient samples from banks in Korea and the United Kingdom, and found to be expressed at significantly higher levels in blast crisis CML (FIG. 18A, 18B). FIG. 18A shows data from PCR analysis of MSI2 expression in chronic and blast crisis CML patient samples from the Korean Leukemia Bank (n=9 per cohort, Mann-Whitney U test p<0.001) and FIG. 18B shows data from the Hammersmith MRD Lab Sample Archive in the United Kingdom (n=6 per cohort, Mann-Whitney U test, p<0.001).

Figure 18:
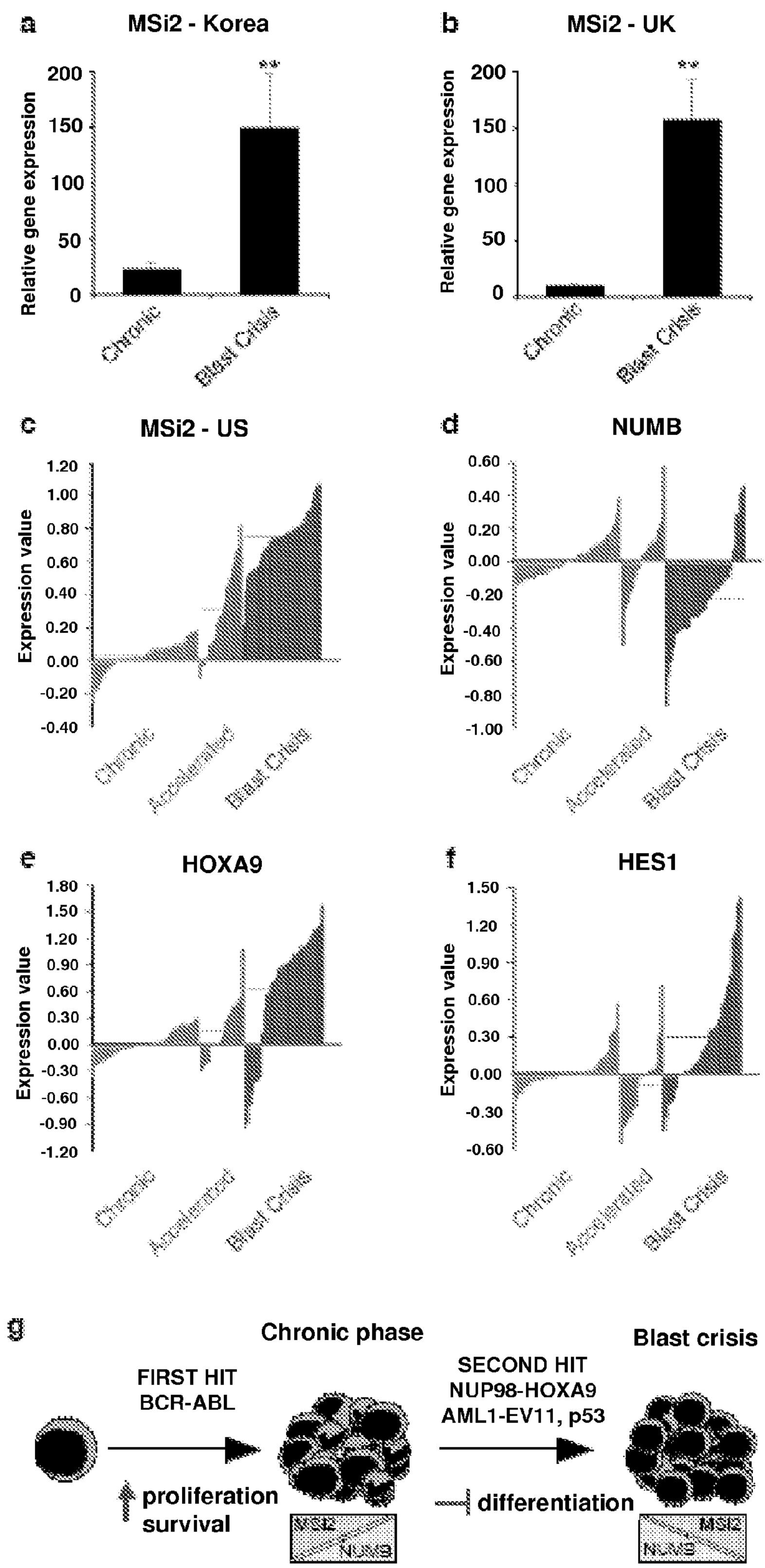
FIG. 18A is a graph of MSI2 expression in chronic and blast crisis CML patient samples from the Korean Leukemia Bank.
FIG. 18B is a graph of MSI2 expression in chronic and blast crisis CML patient samples from the Hammersmith MRD Lab Sample Archive.
FIG. 18C is a microarray analysis of expression of MSI2 in bone marrow and peripheral blood samples.
FIG. 18D is a microarray analysis of expression of NUMB in bone marrow and peripheral blood samples.
FIG. 18E is a microarray analysis of expression of HOXA9 in bone marrow and peripheral blood samples.
FIG. 18F is a microarray analysis of expression of HES1 in bone marrow and peripheral blood samples.
FIG. 18G is a schematic diagram of a proposed model for the role of Musashi and Numb in CML progression.
Figure 19:
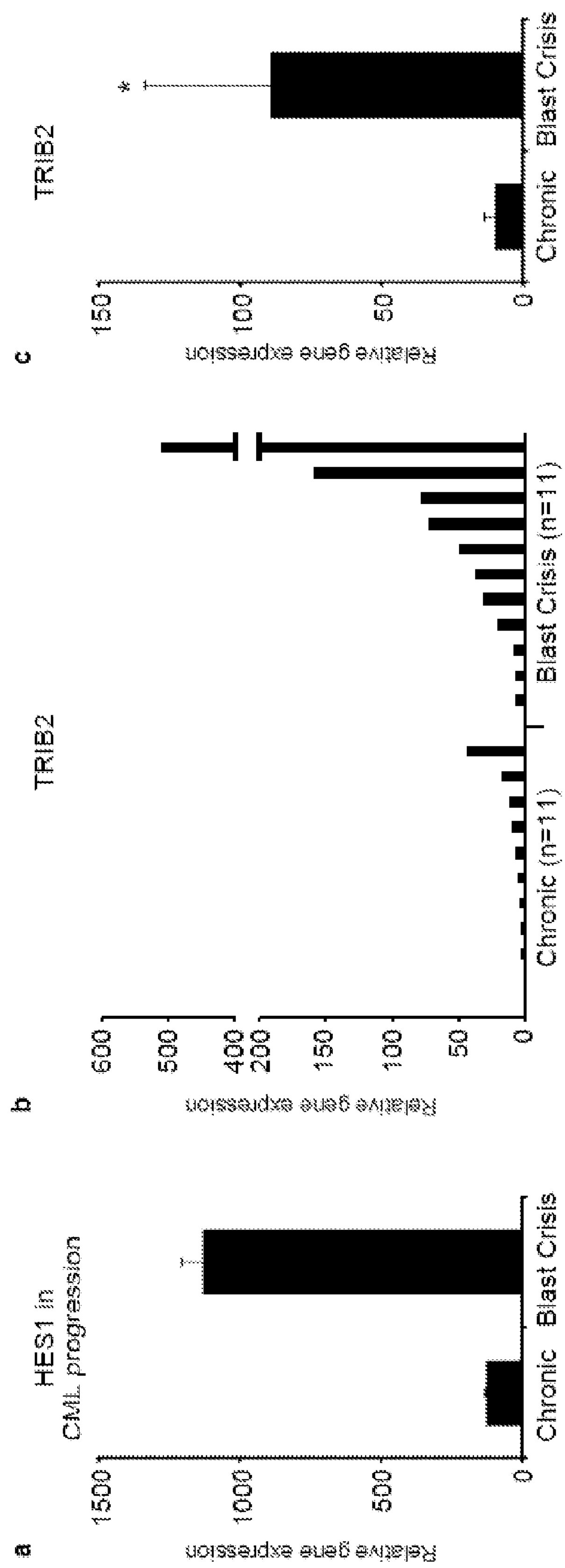
FIG. 19A is a graph of HES1 expression during CML progression within a single patient.
FIG. 19B is a graph of TRIB2 expression in chronic and blast crisis phase cells from CML patient samples in individual samples.
FIG. 19C is a graph of average TRIB2 expression levels in chronic and blast crisis phase cells from CML patient samples.

To determine if this reflected a general pattern in human CML progression, the expression of MSI2 and associated genes were examined in 90 patient samples from banks in the United States (Radich, J. P. et al. *Proc Natl Acad Sci USA* 2006, 103, 2794-2799, incorporated herein by reference in its entirety). FIG. 18 shows data from microarray analysis of expression of MSI2 (FIG. 18C, p<0.001), NUMB (FIG. 18D, p<0.001), HOXA9 (FIG. 18E, p<0.001), and HES1 (FIG. 18F, p=0.68) in bone marrow and peripheral blood samples from 42 chronic (red), 17 accelerated (green), and 31 blast crisis phase (blue) patients in the United States. Microarray analysis revealed a dramatic upregulation of MSI2 in every patient during CML progression (FIG. 18C). In addition, NUMB was downregulated in a majority of blast crisis patients (FIG. 18D). Notably, our mouse model was driven by NUP98-HOXA9 as a second hit, whereas human blast crisis CMLs harbor a variety of secondary mutations. Msi2 could be regulated by HoxA9 expression in the mouse model of CML, and it was examined if HOXA9 was upregulated in blast crisis CML samples. The observation that a majority of patient samples had elevated levels of HOXA9 (FIG. 18E) may explain how MSI2 becomes upregulated in advanced stage disease regardless of the nature of the second hit. Notch signaling targets HES1 and TRIB2 were also elevated in a number of blast crisis patient samples (FIG. 18F, FIG. 19). Notch signaling-associated genes HES1 and TRIB2 are elevated in blast crisis patient samples. FIG. 19A shows HES 1 expression during CML progression within a single patient, determined via PCR analysis of HES1 in sorted CD34+ chronic phase and blast crisis phase cells from the same individual (Singapore General Hospital). Error bars represent s.e.m. of triplicate PCRs. FIGS. 19B and 19C show results for chronic and blast crisis phase cells from CML patient samples (United Kingdom and Korean banks) that were isolated, RNA prepared, and TRIB2 expression analyzed by realtime RTPCR (FIG. 19B, expression levels in individual samples; FIG. 19C, average expression levels n=11 for each leukemia, Mann-Whitney U test, *p=0.0031).

Because the highest MSI2 expression was observed in blast crisis patients, where treatment outcomes are extremely poor, and because a range of expression was observed in both chronic and accelerated phase CML, it was tested whether MSI2 expression correlated with outcomes after allogeneic transplantation. Patients were divided into two groups based on median expression of MSI2. Among 37 chronic phase patients with available outcomes (9 relapses) increased MSI2 expression was associated with a higher risk of relapse (hazard ratio=4.35; 95% CI, 0.90-21.06, p=0.07). Additionally, among 13 accelerated phase patients with available outcomes (6 deaths and 3 relapses), increased MSI2 expression was not only associated with higher risk of relapse (all relapses occurred in the increased MSI2 group, p=0.06), but also with higher risk of death (hazard ratio=6.76; 95% CI, 0.78-58.57, p=0.08). The association of MSI2 with poorer outcomes suggests that Msi2 may be an early marker of advanced CML disease.

Our work identifies the Musashi-Numb axis as an important regulator of myeloid leukemia and indicates that maintenance of the immature state is dependent on reversal of classic differentiation cues. Specifically, it was found that Msi2 is upregulated and Numb downregulated as chronic phase CML progresses to blast crisis, and that modulation of this pathway can inhibit disease. Without being limited as to theory, a proposed model for the role of Musashi and Numb in CML progression is shown in FIG. 18G. The Musashi and Numb pathway is required for hematologic malignancy.

Numb, which drives commitment and differentiation, can impair blast crisis CML establishment and propagation. Just as Numb's influence may be mediated through p53 and/or Notch signaling, Musashi may act through Numb as well as other targets such as p21WAF1. Specific differentiation cues associated with the Musashi-Numb cascade may unlock the differentiation potential of blast crisis CML and impair its growth. Musashi may be an early marker of advanced CML. Musashi expression may serve as a prognostic tool, and targeting it may be used in therapy.

Various features and advantages of the invention are set forth in the following claims.

What is claimed is:

1. A method of reducing proliferation of a leukemia cell, the method comprising:

determining a level of Numb expression in the leukemia cell, wherein determining comprises a method selected from the group consisting of PCR, Western blot analysis, Northern blot analysis, ELISA, FACS analysis, and immunofluorescence;

comparing the expression level to a control value; and administering to the leukemia cell a therapy alternative to a tyrosine kinase inhibitor when the level of Numb expression is decreased relative to the control wherein the alternative therapy comprises an agent capable of increasing the level of Numb protein selected from the group consisting of a polynucleotide encoding a polypeptide having an amino acid sequence consisting of at least one of SEQ ID NOs: 12, 14, 16, 18, 20, 22, and 24; polypeptide having an amino acid sequence consisting of at least one of SEQ ID NOs: 12, 14, 16, 18, 20, 22, and 24; a gene expression activator or de-repressor of Numb; and an agent that binds to Numb directly or indirectly and increases the effective level of Numb; or any combination thereof.

2. The method of claim 1, wherein the leukemia cell is a lymphoma cell, a lymphoid leukemia cell, a myeloid leukemia cell, a glioblastoma cell, or a breast cancer cell.

3. The method of claim 1, wherein the tyrosine kinase inhibitor is selected from the group consisting of imatinib, mesylate, nilotinib, and dasatinib.

4. The method of claim 1, wherein the alternative therapy further comprises a therapy selected from the group consisting of radiation therapy, a surgical procedure, anti-cancer drugs, or any combination thereof.

5. The method of claim 1, wherein determining comprises PCR with an array of primers, each primer having a polynucleotide sequence selected from the group consisting of SEQ ID NOs: 1-8.

* * * * *